US010328133B2

(12) United States Patent
Mooney et al.

(10) Patent No.: US 10,328,133 B2
(45) Date of Patent: Jun. 25, 2019

(54) CONTINUOUS CELL PROGRAMMING DEVICES

(75) Inventors: David J. Mooney, Sudbury, MA (US); Omar Ali, Cambridge, MA (US); Glenn Dranoff, Lexington, MA (US)

(73) Assignees: President and Fellows of Harvard College, Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 723 days.

(21) Appl. No.: 12/867,426

(22) PCT Filed: Feb. 13, 2009

(86) PCT No.: PCT/US2009/000914
§ 371 (c)(1),
(2), (4) Date: Jan. 13, 2012

(87) PCT Pub. No.: WO2009/102465
PCT Pub. Date: Aug. 20, 2009

(65) Prior Publication Data
US 2012/0100182 A1    Apr. 26, 2012

Related U.S. Application Data

(60) Provisional application No. 61/143,630, filed on Jan. 9, 2009, provisional application No. 61/065,672, filed on Feb. 13, 2008.

(51) Int. Cl.
| A61K 45/06 | (2006.01) |
| A61K 38/19 | (2006.01) |
| A61K 39/39 | (2006.01) |
| A61K 39/00 | (2006.01) |
| A61K 31/7088 | (2006.01) |
| A61K 39/385 | (2006.01) |
| A61K 31/4745 | (2006.01) |
| A61K 31/708 | (2006.01) |

(52) U.S. Cl.
CPC ...... *A61K 39/0011* (2013.01); *A61K 31/4745* (2013.01); *A61K 31/708* (2013.01); *A61K 31/7088* (2013.01); *A61K 38/193* (2013.01); *A61K 39/39* (2013.01); *A61K 45/06* (2013.01); *A61K 2039/54* (2013.01); *A61K 2039/55516* (2013.01); *A61K 2039/55522* (2013.01); *A61K 2039/55561* (2013.01); *A61K 2039/55588* (2013.01); *A61K 2039/6093* (2013.01)

(58) Field of Classification Search
None
See application file for complete search history.

(56) References Cited

U.S. PATENT DOCUMENTS

| 3,773,919 A | 11/1973 | Boswell et al. |
| 4,522,811 A | 6/1985 | Eppstein et al. |
| 4,946,778 A | 8/1990 | Ladner et al. |
| 5,073,627 A | 12/1991 | Curtis et al. |
| 5,091,513 A | 2/1992 | Huston et al. |
| 5,132,405 A | 7/1992 | Huston et al. |
| 5,885,829 A | 3/1999 | Mooney et al. |
| 5,888,987 A | 3/1999 | Haynes et al. |
| 5,906,826 A | 5/1999 | Emery et al. |
| 6,129,716 A | 10/2000 | Steer |
| 6,193,970 B1 | 2/2001 | Pardoll et al. |
| 6,251,396 B1 | 6/2001 | Gaur et al. |
| 6,281,256 B1 | 8/2001 | Harris et al. |
| 6,334,968 B1 | 1/2002 | Shapiro et al. |
| 6,403,374 B1 | 6/2002 | Tsien et al. |
| 6,429,199 B1 | 8/2002 | Krieg et al. |
| 6,511,650 B1 | 1/2003 | Eiselt et al. |
| 6,541,022 B1 | 4/2003 | Murphy et al. |
| 6,642,363 B1 | 11/2003 | Mooney et al. |
| 6,685,963 B1 | 2/2004 | Taupin et al. |
| 6,748,954 B2 | 6/2004 | Lee et al. |
| 6,767,928 B1 | 7/2004 | Murphy et al. |
| 6,783,712 B2 | 8/2004 | Slivka et al. |
| 6,790,840 B1 | 9/2004 | Lee et al. |
| 6,797,738 B2 | 9/2004 | Harris et al. |
| 6,800,733 B2 | 10/2004 | Tsien et al. |
| 6,974,698 B1 * | 12/2005 | Miller ............ A61K 48/0008 435/375 |
| 7,157,566 B2 | 1/2007 | Tsien et al. |
| 7,186,413 B2 | 3/2007 | Bouhadir et al. |
| 7,192,693 B2 | 3/2007 | Bryant et al. |
| 7,244,714 B1 | 7/2007 | Gonda et al. |
| 7,427,602 B1 | 9/2008 | Shea et al. |

(Continued)

FOREIGN PATENT DOCUMENTS

| EP | 0562862 A1 | 9/1993 |
| EP | 1452191 A2 | 9/2004 |

(Continued)

OTHER PUBLICATIONS

Sarkar et al., Nucleic Acids Research, 33(1):143-151, 2005.*
Sonawane et al., Journal of Biological Chemistry, 278(45):44826-44831, 2003.*
Latz et al., Nature Immunology, 3(2):190-198, 2004.*
Goddard et al., Porgress in Polymer Science, 32(7):698-725.*
Goddard et al., Progress in Polymer Science, 32(7):698-725, 2007.*
Ali et al. "Controlled Local Delivery of GM-CSF From Polymer-Based Vaccines Enhances Anti-Tumor Immune Responses by Priming Host Dendritic Cells." *2007 AACR Annual Meeting.* 48(2007):652. (Abstract #2736).
All et al. "Sustained GM-CSF and PEI Condensed pDNA Presentation Increases the Level and Duration of Gene Expression in Dendritic Cells." *J. Control. Release.* 132.3(2008):273-278.

(Continued)

*Primary Examiner* — Marianne P Allen
(74) *Attorney, Agent, or Firm* — McCarter & English, LLP; Maria Laccotripe Zacharakis; Maneesh Gulati

(57) ABSTRACT

The present invention comprises compositions, methods and devices for creating an infection-mimicking environment within a polymer scaffold to stimulate antigen-specific dendritic cell activation. Devices of the present invention are used to provide protective immunity to subjects against infection and cancer.

8 Claims, 26 Drawing Sheets

(56) References Cited

U.S. PATENT DOCUMENTS

| | | | |
|---|---|---|---|
| 7,575,759 B2 | 8/2009 | Murphy et al. | |
| 7,687,241 B2 | 3/2010 | Chen | |
| 7,790,699 B2 | 9/2010 | Melvik et al. | |
| 8,067,237 B2 | 11/2011 | Mooney et al. | |
| 8,188,058 B2 * | 5/2012 | Hackam et al. | 514/44 R |
| 8,273,373 B2 | 9/2012 | Alsberg et al. | |
| 8,709,464 B2 | 4/2014 | Ma et al. | |
| 8,728,456 B2 | 5/2014 | Sands et al. | |
| 8,932,583 B2 | 1/2015 | Mooney et al. | |
| 9,012,399 B2 | 4/2015 | Cao et al. | |
| 9,132,210 B2 | 9/2015 | Mooney et al. | |
| 9,370,558 B2 | 6/2016 | Ali et al. | |
| 9,446,107 B2 | 9/2016 | Mooney et al. | |
| 9,486,512 B2 | 11/2016 | Kim et al. | |
| 9,675,561 B2 | 6/2017 | Bencherif et al. | |
| 9,821,045 B2 | 11/2017 | Ali et al. | |
| 2002/0131853 A1 | 9/2002 | Nagasawa | |
| 2002/0150604 A1 | 10/2002 | Yi et al. | |
| 2003/0075822 A1 | 4/2003 | Slivka et al. | |
| 2003/0082806 A1 | 5/2003 | Berenson et al. | |
| 2003/0095994 A1 | 5/2003 | Geistlich et al. | |
| 2003/0100527 A1 | 5/2003 | Krieg et al. | |
| 2003/0194397 A1 | 10/2003 | Mishra | |
| 2003/0232895 A1 | 12/2003 | Omidian et al. | |
| 2004/0058883 A1 | 3/2004 | Phillips et al. | |
| 2004/0063206 A1 | 4/2004 | Rowley et al. | |
| 2004/0136968 A1 | 7/2004 | Zheng et al. | |
| 2004/0151764 A1 | 8/2004 | Zamora | |
| 2004/0220111 A1 | 11/2004 | Kleinman et al. | |
| 2004/0242469 A1 | 12/2004 | Lee et al. | |
| 2004/0242482 A1 | 12/2004 | Gehring et al. | |
| 2005/0002915 A1 | 1/2005 | Atala et al. | |
| 2005/0037330 A1 | 2/2005 | Fischer et al. | |
| 2005/0053667 A1 | 3/2005 | Irvine et al. | |
| 2005/0079159 A1 | 4/2005 | Shastri et al. | |
| 2005/0090008 A1 * | 4/2005 | Segura et al. | 435/459 |
| 2005/0106211 A1 | 5/2005 | Nelson et al. | |
| 2005/0154376 A1 | 7/2005 | Riviere et al. | |
| 2005/0177249 A1 | 8/2005 | Kladakis et al. | |
| 2005/0202394 A1 | 9/2005 | Dobson | |
| 2006/0083712 A1 | 4/2006 | Anversa | |
| 2006/0141018 A1 | 6/2006 | Cochrum et al. | |
| 2006/0264380 A1 | 11/2006 | Hellstrom et al. | |
| 2006/0292134 A1 | 12/2006 | Stohs | |
| 2007/0003595 A1 | 1/2007 | Wang et al. | |
| 2007/0020232 A1 | 1/2007 | Rossignol et al. | |
| 2007/0026518 A1 | 2/2007 | Healy et al. | |
| 2007/0081972 A1 * | 4/2007 | Sandler | A61K 9/0024 424/85.1 |
| 2007/0116680 A1 | 5/2007 | Stegemann et al. | |
| 2007/0178159 A1 | 8/2007 | Chen et al. | |
| 2007/0190646 A1 | 8/2007 | Engler et al. | |
| 2008/0044900 A1 | 2/2008 | Mooney et al. | |
| 2008/0044990 A1 | 2/2008 | Lee | |
| 2008/0051490 A1 | 2/2008 | Williams et al. | |
| 2008/0138416 A1 | 6/2008 | Rauh et al. | |
| 2008/0152624 A1 | 6/2008 | Paludan et al. | |
| 2008/0206308 A1 | 8/2008 | Jabbari et al. | |
| 2008/0268052 A1 | 10/2008 | Voytik-Harbin et al. | |
| 2009/0017096 A1 | 1/2009 | Lowman et al. | |
| 2009/0192079 A1 | 7/2009 | Santos et al. | |
| 2009/0238853 A1 | 9/2009 | Liu et al. | |
| 2009/0297579 A1 | 12/2009 | Semino et al. | |
| 2009/0305983 A1 | 12/2009 | Ying et al. | |
| 2010/0015709 A1 | 1/2010 | Rehfeldt et al. | |
| 2010/0055186 A1 | 3/2010 | Dadsetan et al. | |
| 2010/0080816 A1 | 4/2010 | Hadeiba et al. | |
| 2010/0129422 A1 | 5/2010 | Han et al. | |
| 2010/0159008 A1 | 6/2010 | Barron et al. | |
| 2010/0189760 A1 | 7/2010 | Schaffer et al. | |
| 2010/0190741 A1 | 7/2010 | Cohen et al. | |
| 2010/0272771 A1 | 10/2010 | Harlow et al. | |
| 2011/0020216 A1 | 1/2011 | Mooney et al. | |
| 2011/0117170 A1 | 5/2011 | Cao et al. | |
| 2011/0223255 A1 | 9/2011 | Thiesen et al. | |
| 2012/0121539 A1 | 5/2012 | Sands et al. | |
| 2012/0122218 A1 | 5/2012 | Huebsch et al. | |
| 2012/0134967 A1 | 5/2012 | Mooney et al. | |
| 2012/0256336 A1 | 10/2012 | Yano et al. | |
| 2012/0264599 A1 | 10/2012 | Komatsu et al. | |
| 2012/0329791 A1 | 12/2012 | Ashwell et al. | |
| 2013/0029030 A1 | 1/2013 | Larsen | |
| 2013/0072547 A1 | 3/2013 | Hackam et al. | |
| 2013/0177536 A1 | 7/2013 | Mooney et al. | |
| 2013/0202707 A1 | 8/2013 | Ali et al. | |
| 2013/0302396 A1 | 11/2013 | Mooney et al. | |
| 2013/0331343 A1 | 12/2013 | Cao et al. | |
| 2014/0079752 A1 | 3/2014 | Huebsch et al. | |
| 2014/0112990 A1 | 4/2014 | Bencherif et al. | |
| 2014/0178964 A1 | 6/2014 | Mooney et al. | |
| 2014/0193488 A1 | 7/2014 | Kim et al. | |
| 2014/0227327 A1 | 8/2014 | Bencherif et al. | |
| 2014/0234423 A1 | 8/2014 | Sands et al. | |
| 2015/0024026 A1 | 1/2015 | Mooney et al. | |
| 2015/0072009 A1 | 3/2015 | Kim et al. | |
| 2015/0366956 A1 | 12/2015 | Mooney et al. | |
| 2016/0220667 A1 | 8/2016 | Mooney et al. | |
| 2016/0220668 A1 | 8/2016 | Mooney et al. | |
| 2016/0228543 A1 | 8/2016 | Mooney et al. | |
| 2016/0271298 A1 | 9/2016 | Mooney et al. | |
| 2016/0279219 A1 | 9/2016 | Mooney et al. | |
| 2016/0279220 A1 | 9/2016 | Mooney et al. | |
| 2016/0296611 A1 | 10/2016 | Ali et al. | |
| 2017/0042995 A1 | 2/2017 | Ali et al. | |
| 2017/0182138 A1 | 6/2017 | Kim et al. | |

FOREIGN PATENT DOCUMENTS

| | | |
|---|---|---|
| EP | 1561481 A2 | 8/2005 |
| JP | 2000503884 A | 4/2000 |
| JP | 2003506401 A | 2/2003 |
| JP | 2003180815 A | 7/2003 |
| JP | 2004520043 | 7/2004 |
| JP | 2005160669 A | 6/2005 |
| JP | 2005528401 A | 9/2005 |
| JP | 2007500673 | 1/2007 |
| JP | 2007503881 | 3/2007 |
| JP | 2007505827 A | 3/2007 |
| JP | 2007528848 | 10/2007 |
| JP | 2008515503 A | 5/2008 |
| JP | 2008528114 A | 7/2008 |
| JP | 2009519042 | 5/2009 |
| JP | 2009521406 | 6/2009 |
| JP | 2009540921 | 11/2009 |
| JP | 2010502824 A | 1/2010 |
| JP | 2010508976 | 3/2010 |
| JP | 2011511684 A | 4/2011 |
| JP | 2011511834 A | 4/2011 |
| JP | 2013531043 A | 8/2013 |
| WO | WO-9602555 A1 | 2/1996 |
| WO | WO-9616086 A1 | 5/1996 |
| WO | WO-9812228 A1 | 3/1998 |
| WO | WO-9816266 A1 | 4/1998 |
| WO | WO-9944583 A2 | 9/1999 |
| WO | WO-9951259 A2 | 10/1999 |
| WO | WO-0050006 A2 | 8/2000 |
| WO | WO-0110421 A1 | 2/2001 |
| WO | WO-0135932 A2 | 5/2001 |
| WO | WO-0137810 A2 | 5/2001 |
| WO | WO-0216557 A2 | 2/2002 |
| WO | WO-0240071 A1 | 5/2002 |
| WO | WO02058723 | 8/2002 |
| WO | WO-02092054 A2 | 11/2002 |
| WO | WO-2003/020884 A2 | 3/2003 |
| WO | WO-03020161 A2 | 3/2003 |
| WO | WO-03088905 A2 | 10/2003 |
| WO | WO-2004006990 A2 | 1/2004 |
| WO | WO-2004029230 A2 | 4/2004 |
| WO | WO-2004030706 A2 | 4/2004 |
| WO | WO-2004031371 A2 | 4/2004 |
| WO | WO-2004/089413 A1 | 10/2004 |
| WO | WO2005013896 | 2/2005 |
| WO | WO2005013933 | 2/2005 |
| WO | WO-2005020849 A2 | 3/2005 |

(56) References Cited

FOREIGN PATENT DOCUMENTS

| WO | WO-2005025614 A2 | 3/2005 |
|---|---|---|
| WO | WO-2005026318 A2 | 3/2005 |
| WO | WO-2005037190 A2 | 4/2005 |
| WO | WO-2005037293 A1 | 4/2005 |
| WO | WO-2005046748 A1 | 5/2005 |
| WO | WO-2005072088 A2 | 8/2005 |
| WO | WO-2006040128 A1 | 4/2006 |
| WO | WO-2006078987 A2 | 7/2006 |
| WO | WO-2006119619 A1 | 11/2006 |
| WO | WO-2006136905 A2 | 12/2006 |
| WO | WO-2007030901 A1 | 3/2007 |
| WO | WO-2007042554 A2 | 4/2007 |
| WO | WO2007063075 | 6/2007 |
| WO | WO-2007063075 A1 | 6/2007 |
| WO | WO-2007064152 A1 | 6/2007 |
| WO | WO-2007070660 A2 | 6/2007 |
| WO | WO-2007078196 A1 | 7/2007 |
| WO | WO-2007089870 A2 | 8/2007 |
| WO | WO-2007107739 A1 | 9/2007 |
| WO | WO 2007/150020 * | 12/2007 |
| WO | WO-2007149161 A2 | 12/2007 |
| WO | WO-2007150020 A1 | 12/2007 |
| WO | WO-2008018707 A1 | 2/2008 |
| WO | WO-2008031525 A1 | 3/2008 |
| WO | WO-2008057600 A2 | 5/2008 |
| WO | WO2008109852 | 9/2008 |
| WO | WO2008114149 | 9/2008 |
| WO | WO2008148761 | 12/2008 |
| WO | WO2008157394 | 12/2008 |
| WO | WO-2009002401 A2 | 12/2008 |
| WO | WO-2009005769 A2 | 1/2009 |
| WO | WO2009018500 | 2/2009 |
| WO | WO2009072767 | 6/2009 |
| WO | WO-2009074341 A1 | 6/2009 |
| WO | WO-2009100716 A2 | 8/2009 |
| WO | WO-2009102465 A2 | 8/2009 |
| WO | WO-2009146456 A1 | 12/2009 |
| WO | WO-2009155583 A1 | 12/2009 |
| WO | WO-2010/078209 | 7/2010 |
| WO | WO-2010120749 A2 | 10/2010 |
| WO | WO-2011014871 A1 | 2/2011 |
| WO | WO-2011063336 A2 | 5/2011 |
| WO | WO-2011109834 A2 | 9/2011 |
| WO | WO-2011130753 A2 | 10/2011 |
| WO | WO-2011150240 A1 | 12/2011 |
| WO | WO-2011151431 A1 | 12/2011 |
| WO | WO-2011163669 A2 | 12/2011 |
| WO | WO-2012009611 A2 | 1/2012 |
| WO | WO-2012019049 A1 | 2/2012 |
| WO | WO-2012048165 A2 | 4/2012 |
| WO | WO-2012064697 A2 | 5/2012 |
| WO | WO-2012148684 A1 | 11/2012 |
| WO | WO-2012149358 A1 | 11/2012 |
| WO | WO-2012167230 A1 | 12/2012 |
| WO | WO-2013106852 A1 | 7/2013 |
| WO | WO-2013158673 A1 | 10/2013 |
| WO | WO-2015168379 A2 | 11/2015 |
| WO | WO-2016123573 A1 | 8/2016 |
| WO | WO-2016161372 A1 | 10/2016 |

OTHER PUBLICATIONS

Kumamoto et al. "Induction of Tumor-Specific Protective Immunity by in situ Langerhans Cell Vaccine." *Nat. BioTechnol.* 20.1(2002):64-69.
Gamvrellis et al. "Vaccines that Facilitate Antigen Entry into Dendritic Cells." *Immunol. Cell Biol.* 82(2004):506-516.
Zhang et al. "A Comparative Study of the Antigen-Specific Immune Response Induced by Co-Delivery of CpG OGN and Antigen Using Fusion Molecules or Biodegradable Microparticles." *J. Pharma. Sci.* 98.12(2007):3283-3292.
"Antigens and Receptors." *Immunology*. Doan et al., eds. Philadelphia: Wolters Kluwer/Lippincott Williams & Wilsons. (2008):11-23.

Abrahams et al. "Expression and Secretion of Antiviral Factors by Trophoblast Cells Following Stimulation by the TLF-3 Agonist, Poly (I:C)." *Hum. Reprod.* 21.9(2006):2432-2439.
Agrawal et al. "Cutting Edge: Different Toll-Like Receptor Agonists Instruct Dendritic Cells to Induce Distinct Th Responses via Differential Modulation of Extracellular Signal-Regulated Kinase-Mitogen-Activated Protein Kinase and c-Fos." *J. Immunol.* 171.10(2003):4984-4989.
Akira et al. "Pathogen Recognition and Innate Immunity." *Cell.* 124.4(2006):783-801.
Akira et al. "Toll-Like Receptors: Critical Proteins Linking Innate and Acquired Immunity." *Nat. Immunol.* 2.8(2001):675-680.
Aldhous. "Print Me a Heart and a Set of Arteries." *New Scientist.* 2547(2006):19.
Ali et al. "Converging Cell Therapy with Biomaterials." *Cell Transplantation from Laboratory to Clinic*. Burlington, MA: Elsevier, Inc. (2006):591-609.
Ali et al. "In situ Regulation of DC Subsets and T Cells Mediates Tumor Regression in Mice." *Sci. Transl. Med.* 1.8(2009):8-19.
Ali et al. "Infection-Mimicking Materials to Program Dendritic Cells in situ." *Nat. Mater.* 8.2(2009):151-158.
Allen et al. "Regulation of Satellite Cells During Skeletal Muscle Growth and Development." *Proc. Soc. Exp. Biol. Med.* 194.2(1990):81-86.
Allen et al. "Regulation of Skeletal Muscle Satellite Cell Proliferation by Bovine Pituitary Fibroblast Growth Factor." *Exp. Cell Res.* 152.1(1984):154-160.
Almarza et al. "Evaluation of Three Growth Factors in Combination of Two for Temporomandibular Joint Disc Tissue Engineering." *Arch. Oral Biol.* 51.3(2006):215-221.
Alsberg et al. "Cell-Interactive Alginate Hydrogels for Bone Tissue Engineering." *J. Dent. Res.* 80.11(2001):2025-2029.
Alsberg et al. "Engineering Growing Tissues." *PNAS.* 99.18(2002):12025-12030.
Anderson et al. "The NOD Mouse: A Model of Immune Dysregulation." *Annu. Rev. Immunol.* 23(2005):447-485.
Anderson. "A Role for Nitric Oxide in Muscle Repair: Nitric Oxide-Mediated Activation of Muscle Satellite Cells." *Mol. Biol. Cell.* 11(2000):1859-1874.
Arany et al. "At the Edge of Translation—Materials to Program Cells for Directed Differentiation." *Oral Dis.* 17.3(2011):241-251.
Atala et al. "Endoscopic Treatment of Vesicoureteral Reflux with a Chondrocyte-Alginate Suspension." *J. Urol.* 152(1994):641-643.
Bachelder et al. "Acid-Degradable Polyurethane Particles for Protein-Based Vaccines: Biological Evaluation and in Vitro Analysis of Particle Degradation Products." *Mol. Pharm.* 5.5(2008):876-884.
Badovinac et al. "Regulation of CD8 T+ Cells Undergoing Primary and Secondary Responses to Infection in the Same Host." *J. Immunol.* 170(2003):4933-4942.
Bakri et al. "Pharmacokinetics of Intravitreal Bevacizumab (Avastin)." *Ophthalmology.* 114.5(2007):855-859.
Banchereau et al. "Dendritic Cells and the Control of Immunity." *Nature.* 392.6673(1998):245-252.
Bar-Or et al. "Induction of Antigen-Specific Tolerance in Multiple Sclerosis after Immunization with DNA Encoding Myelin Basic Protein in a Randomized, Placebo-Controlled Phase 1/2 Trial." *Arch. Neurol.* 64.10(2007):1407-1415.
Barbero et al. "Growth Factor Supplemented Matrigel Improves Ectopic Skeletal Muscle Formation—A Cell Therapy Approach." *J. Cell. Physiol.* 186(2001):183-192.
Barrio et al. "A Two-Dimensional Numerical Study of Spatial Pattern Formation in Interacting Turing Systems." *Bull. Math Biol.* 61.3(1999):483-505.
Beauchamp et al. "Dynamics of Myoblast Transplantation Reveal a Discrete Minority of Precursors with Stem Cell-Like Properties as the Myogenic Source." *J. Cell Biol.* 144.6(1999):1113-1122.
Bischoff. "Proliferation of Muscle Satellite Cells on Intact Myofibers in Culture." *Dev. Biol.* 115.1(1986):129-139.
Blanas et al. "Induction of Autoimmune Diabetes by Oral Administration of Autoantigen." *Science.* 274.5293(1996):1707-1709.
Bohl et al. "Role of Synthetic Extracellular Matrix in Development of Engineered Dental Pulp." *J. Biomater. Sci. Polym. Ed.* 9.7(1998):749-764.

(56) References Cited

OTHER PUBLICATIONS

Bonauer et al. "MicroRNA-92a Controls Angiogenesis and Functional Recovery of Ischemic Tissues in Mice." *Science.* 324. 5935(2009):1710-1713.
Boontheekul et al. "Regulating Myoblast Phenotype Through Controlled Gel Stiffness and Degradation." *Tissue Engin.* 13.7(2007):1431-1442.
Borselli et al. "Functional Muscle Regeneration with Combined Delivery of Angiogenesis and Myogenesis Factors." *PNAS.* 107.8(2010):3287-3292.
Bouhadir et al. "Synthesis of Cross-Linked Poly(aldehyde guluronate) Hydrogels." *Polymer.* 40(1999):3575-3584.
Bowne et al. "Injection of DNA Encoding Granulocyte-Macrophage Colony-Stimulating Factor Recruits Dendritic Cells for Immune Adjuvant Effects." *Cytokines Cell Mol. Ther.* 5.4(1999):217-225.
Brinkman et al. "Photo-Cross Linking of Type 1 Collagen Gels in the Presence of Smooth Muscle Cells: Mechanical Properties, Cell Viability, and Function." *Biomacromolecules.* 4.4(2003):890-895.
Brouwers et al. "Can the Growth Factors PTHrP, Ihh and VEGF, Together Regulate the Development of a Long Bone?" *J. Biomech.* 39.15(2006):2774-2782.
Burdick et al. "Stimulation of Neurite Outgrowth by Neurotrophins Delivered From Degradable Hydrogels." *Biomater.* 27.3(2006):452-459.
Cao et al. "Promoting Angiogenesis via Manipulation of VEGF Responsiveness with Notch Signaling." *Biomater.* 30.25(2009):4085-4093.
Carlson et al. "Notch Signaling Pathway and Tissue Engineering." *Front. Biosci.* 12(2007):5143-5156.
Carmeliet et al. "Angiogenesis in Cancer and Other Diseases." *Nature.* 407.6801(2000):249-257.
Carmeliet. "Mechanisms of Angiogenesis and Arteriogenesis." *Nat. Med.* 6.3(2000):389-395.
Chan et al. "Antifibrotic Effects of Suramin in Injured Skeletal Muscle After Laceration." *J. Appl. Physiol.* 95(2003):771-780.
Chan et al. "Helix Induction in Antimicrobial Peptides by Alginate in Biofilms." *J. Biol. Chem.* 279.37(2004):38749-38754.
Chen et al. "Integrated Approach to Designing Growth Factor Delivery Systems." *FASEB.* 21.14(2007):3896-3903.
Chen et al. "Polymeric Growth Factor Delivery Strategies for Tissue Engineering." *Pharm. Res.* 20.8(2003):1103-1112.
Chen et al. "Skeletal Muscle Stem Cells." *Reprod. Biol. Endocrinol.* 1(2003):101.
Chen et al. "Spatio-Temporal VEGF and PDGF Delivery Patterns Blood Vessel Formation and Maturation." *Pharm. Res.* 24.2(2007):258-264.
Choi. "Replacement Organs, Hot Off the Press." *New Scientist.* 177.2379(2003):16.
Chromiak et al. "Bioreactor Perfusion System for the Long-Term Maintenance of Tissue-Engineered Skeletal Muscle Organoids." *In Vitro Cell Dev. Biol. Anim.* 34.9(1998):694-703.
Clauss et al. "Interstitial Transport of Rabbit and Sheep Antibodies in Normal and Neoplastic Tissues." *Cancer Res.* 50.12(1990):3487-3492.
Cohen et al. "Controlled Delivery Systems for Proteins Based on Poly(Lactic/Glycolic Acid) Microspheres." *Pharm. Res.* 8.6(1991):713-720.
Conboy et al. "The Regulation of Notch Signaling Controls Satellite Cell Activation and Cell Fate Determination in Postnatal Myogenesis." *Dev. Cell.* 3.3(2002):397-409.
Conn et al. "Purification of a Glycoprotein Vascular Endothelial Cell Mitogen from a Rat Glioma-Derived Cell Line." *PNAS.* 87.4(1990):1323-1327.
Cooper et al. "Extended Amplification In Vitro and Replicative Senescence: Key Factors Implicated in the Success of Human Myoblast Transplantation." *Hum. Gene Ther.* 14(2003):1169-1179.
Cornelison et al. "Single-Cell Analysis of Regulatory Gene Expression in Quiescent and Activated Mouse Skeletal Muscle Satellite Cells." *Dev. Biol.* 191.2(1997):270-283.
Cornelison et al. "Syndecan-3 and Syndecan-4 Specifically Mark Skeletal Muscle Satellite Cells and Are Implicated in Satellite Cell Maintenance and Muscle Regeneration." *Dev. Biol.* 239.1(2001):79-94.
Cullen et al. "Investigation of Vascular Endothelial Growth Factor Effects on Pulmonary Endothelial Monolayer Permeability and Neutrophil Transmigration." *Gen. Pharmacol.* 35.3(2000):149-157.
Curiel et al. "Tumor Immunotherapy: Inching Toward the Finish Line." *J. Clin. Invest.* 109.3(2002):311-312.
D'Amico et al. "The Early Progenitors of Mouse Dendritic Cells and Plasmacytoid Predendritic Cells are within the Bone Marrow Hemopoietic Precursors Expressing Flt3." *J. Exp. Med.* 198.2(2003):293-303.
Daro et al. "Polyethylene Glycomodified GM-CSF Expands CD11bhighCD11chigh but not CD11blowCD11chigh Murine Dendritic Cells In Vivo: A Comparative Analysis with Flt3 Ligand." *J. Immunol.* 165.1(2000):49-58.
De Temmerman et al. "Particulate Vaccines: On the Quest for Optimal Delivery and Immune Response." *Drug Disc. Today.* 16.13/14(2011):569-582.
Den Haan et al. "CD8+ by not CD8– Dendritic Cells Cross-Prime Cytotoxic T Cells In Vivo." *J. Exp. Med.* 192.12(2000):1685-1696.
Dennis et al. "Excitability and Contractility of Skeletal Muscle Engineered From Primary Cultures and Cell Lines." *Am. J. Physiol. Cell Physiol.* 280(2001):C288-C295.
Dennis et al. "Excitability and Isometric Contractile Properties of Mammalian Skeletal Muscle Constructs Engineered in vitro." *In Vitro Cell Dev. Biol. Anim.* 36.5(2000):327-335.
Dieu et al. "Selective Recruitment of Immature and Mature Dendritic Cells by Distinct Chemokines Expressed in Different Anatomic Sites." *J. Exp. Med.* 188.2(1988):373-386.
Dor et al. "Making Vascular Networks in the Adult: Branching Morphogenesis Without a Roadmap." *Trends Cell Biol.* 13.3(2003):131-136.
Dranoff et al. "Vaccination with Irradiated Tumor Cells Engineered to Secrete Murine Granulocyte-Macrophage Colony-Stimulating Factor Stimulates Potent, Specific and Long-Lasting Anti-Tumor Immunity." *PNAS.* 90.8(1993):3539-3543.
Dranoff. "Cyotkines in Cancer Pathogenesis and Cancer Therapy." *Nat. Rev. Cancer.* 4.1(2004):11-22.
Dudley et al. "Adoptive Cell Transfer Therapy Following Non-Myeloablative by Lymphodepleting Chemotherapy for the Treatment of Patients with Refractory Metastatic Melanoma." *J. Clin. Oncol.* 23.10(2005):2346-2357.
Ehrbar et al. "Endothelial Cell Proliferation and Progenitor Maturation by Fibrin-Bound VEGF Variants with Differential Susceptibilities to Local Cellular Activity." *J. Control. Release.* 101(2004):93-109.
Eiselt et al. "Porous Carriers for Biomedical Applications Based on Alginate Hydrogels." *Biomat.* 21.19(2000):1921-1927.
El-Backly et al. "Regeneration of Dentine/Pulp-Like Tissue Using a Dental Pulp Stem Cell/Poly(lactic-co-glycolic) Acid Scaffold Construct in New Zealand White Rabbits." *Aust. Endod. J.* 34.2(2008):52-67.
Eldar et al. "Elucidating Mechanisms Underlying Robustness of Morphogen Gradients." *Curr. Opin. Genet. Dev.* 14.4(2004):435-439.
Eldar et al. "Robustness of the BMP Morphogen Gradient in *Drosophila* Embryonic Patterning." *Nature.* 419.6904(2002):304-308.
Eldar et al. "Self-Enhanced Ligand Degradation Underlies Robustness of Morphogen Gradients." *Dev. Cell.* 5.4(2003):635-646.
Engler et al. "Matrix Elasticity Directs Stem Cell Lingeage Specification." *Cell.* 126.4(2006):677-689.
Ennett et al. "Temporally Regulated Delivery of VEGF in vitro and in vivo." *J. Biomed. Mater. Res. A.* 79.1(2006):176-184.
Faissner et al. "Boundaries and Inhibitory Molecules in Developing Neural Tissues." *Glia.* 13.4(1995):233-254.
Farrar et al. "T Helper Subset Development: Roles of Instruction, Selection, and Transcription." *J. Clin. Invest.* 109.4(2002):431-435.
Ferrara et al. "Angiogenesis as a Therapeutic Target." *Nature.* 438.7070(2005):967-974.

(56) References Cited

OTHER PUBLICATIONS

Ferrara et al. "Discovery and Development of Bevacizumab, an Anti-VEGF Antibody for Treating Cancer." *Nat. Rev. Drug Discov.* 3.5(2004):391-400.
Folkman. "Angiogenesis." *Annu. Rev. Med.* 57(2006):1-18.
Fonseca et al. "Capitalizing on the Immunogenicity of Dying Tumor Cells." *Clin. Cancer Res.* 14.16(2008):1603-1608.
Friedrich et al. "Promoter Traps in Embryonic Stem Cells: A Genetic Screen to Identify and Mutate Developmental Genes in Mice." *Genes Dev.* 5(1991):1513-1523.
Fukushima et al. "The Use of an Antifibrosis Agent to Improve Muscle Recovery After Laceration." *Am. J. Sports Med.* 29.4(2001):394-402.
GenBank Accession No. A32848.1, Jul. 5, 2002.
GenBank Accession No. AAA35789.1, Apr. 27, 1993.
GenBank Accession No. AAA56738.1, Dec. 7, 1994.
GenBank Accession No. AAA60552.1, Nov. 24, 2003.
GenBank Accession No. AAA64297.1, Mar. 24, 1995.
GenBank Accession No. AAB21432.2, Jun. 5, 2000.
GenBank Accession No. AAB29057.2, Mar. 6, 2001.
GenBank Accession No. AAB31818.1, Jan. 25, 1995.
GenBank Accession No. AAC16450.1, May 15, 1998.
GenBank Accession No. AAH07789.1, Jun. 9, 2008.
GenBank Accession No. AAH20698.1, Jul. 15, 2006.
GenBank Accession No. AAH32517.2, Jun. 9, 2008.
GenBank Accession No. AAH93731.1, Jul. 17, 2006.
GenBank Accession No. ABC86910, Jan. 3, 2011.
GenBank Accession No. CAA01954.1, Jun. 15, 1995.
GenBank Accession No. CAA40093.1, Oct. 7, 2008.
GenBank Accession No. CAA62632.1, Sep. 15, 1995.
GenBank Accession No. CAG46721.1, Jun. 29, 2004.
GenBank Accession No. CB171013.1, Feb. 2, 2010.
GenBank Accession No. EU826563.1, Jul. 23, 2008.
GenBank Accession No. NM_000230.2, Dec. 17, 2012.
GenBank Accession No. NM_000514.3, Aug. 19, 2012.
GenBank Accession No. NM_000601.4, Nov. 25, 2012.
GenBank Accession No. NM_000614.3, Sep. 9, 2012.
GenBank Accession No. NM_000660.4, Dec. 9, 2012.
GenBank Accession No. NM_000800.3, Mar. 4, 2012.
GenBank Accession No. NM_001102654.1, Dec. 16, 2012.
GenBank Accession No. NM_001111283.1, Dec. 9, 2012.
GenBank Accession No. NM_001171630.1, Dec. 9, 2012.
GenBank Accession No. NM_001202.3, Nov. 18, 2012.
GenBank Accession No. NM_002506.2, Dec. 9, 2012.
GenBank Accession No. NM_002632.4, May 4, 2011.
GenBank Accession No. NM_003236.2, Aug. 21, 2011.
GenBank Accession No. NM_003263.3, Jan. 5, 2013.
GenBank Accession No. NM_003264.3, Jan. 6, 2013.
GenBank Accession No. NM_003268.5, Nov. 25, 2012.
GenBank Accession No. NM_006068.4, Oct. 28, 2012.
GenBank Accession No. NM_016562.3, Jan. 6, 2013.
GenBank Accession No. NM_030956.3, Oct. 28, 2012.
GenBank Accession No. NM_033023.4, Nov. 18, 2012.
GenBank Accession No. NM_138554.4, Dec. 29, 2012.
GenBank Accession No. NM_138636.4, Dec. 23, 2012.
GenBank Accession No. NM_170731.4, Dec. 9, 2012.
GenBank Accession No. NM_205819.3, Dec. 6, 2012.
GenBank Accession No. NM_205820.1, Jan. 5, 2013.
GenBank Accession No. NM_205823.2, Jan. 6, 2013.
GenBank Accession No. NP_001096124.1, Dec. 16, 2012.
GenBank Accession No. NP_002010.2, Dec. 9, 2012.
GenBank Accession No. NP_003254.2, Jan. 5, 2013.
GenBank Accession No. NP_003255.2, Jan. 6, 2013.
GenBank Accession No. NP_003259.2, Nov. 25, 2012.
GenBank Accession No. NP_006059.2, Oct. 28, 2012.
GenBank Accession No. NP_057646.1, Jan. 6, 2013.
GenBank Accession No. NP_112218.2, Oct. 28, 2012.
GenBank Accession No. NP_570912.2, Nov. 18, 2012.
GenBank Accession No. NP_612564.1, Dec. 29, 2012.
GenBank Accession No. NP_619542.1, Dec. 23, 2012.
GenBank Accession No. NP_991388.2, Dec. 6, 2012.
GenBank Accession No. NP_991389.1, Jan. 5, 2013.
GenBank Accession No. NP_991392.1, Jan. 6, 2013.
GenBank Accession No. P49771.1, Jan. 9, 2013.
Gerhardt et al. "VEGF Guides Angiogenic Sprouting Utilizing Endothelial Tip Cell Filopodia." *J. Cell Biol.* 161.6(2003):1163-1177.
Gilboa. "Dendritic-Cell Based Cancer Vaccines." *J. Clin. Invest.* 117.5(2007):1195-1203.
Gnjatic et al. "Toll-Like Receptor Agonists: Are They Good Adjuvants?" *Cancer J.* 16.4(2010):382-391.
Godbey et al. "Size Matters: Molecular Weight Affects the Efficiency of Poly(ethylenimine) as a Gene Delivery Vehicle." *J. Biomed. Mater. Res.* 45.3(1999):268-275.
Godbey et al. "Tracking the Intracellular Path of Poly(ethylenimine)/DNA Complexes for Gene Delivery." *PNAS.* 96.9(1999):5177-5181.
Gospodarowicz et al. "Effect of Fibroblast Growth Factor on the Division and Fusion of Bovine Myoblasts." *J. Cell Biol.* 70.2(1976):395-405.
Griffith et al. "Tissue Engineering—Current Challenges and Expanding Opportunities." *Science.* 295(2002):1009-1014.
Grimmer et al. "Tracheal Reconstruction Using Tissue-Engineered Cartilage." *Arch. Otolaryngol Head Neck Surg.*130.10(2004):1191-1196.
Gros et al. "A Common Somitic Origin for Embryonic Muscle Progenitors and Satellite Cells." *Nature.* 435(2005):954-958.
Gullberg et al. "Extracellular Matrix and Its Receptors During Development." *Int. J. Dev. Biol.* 39(1995):845-854.
Gussoni et al. "Dystophin Expression and in the mdx Mouse Restored by Stem Cell Transplantation." *Nature.* 401(1999):390-394.
Hamby et al. "Small Molecule Inhibitors of Tumor-Promoted Angiogenesis, Including Protein Tyrosine Kinase Inhibitors." *Pharmacol. Ther.* 82.2-3 1999 :169-193.
Hamdy et al. "Targeting Dendritic Cells with Nano-Particulate PLGA Cancer Vaccine Formulations." *Adv. Drug Deliv. Rev.* 63.10(2011):943-955.
Hamilton et al. "GM-CSF Biology." *Growth Factors.* 22.4(2004):225-231.
Hamilton. "GM-CSF in Inflammation and Autoimmunity." *Trends Immunol.* 23.8(2002):403-408.
Hanada. "Efficacy of Rehabilitative Therapy in Regional Musculoskeletal Conditions." *Best Pract. Res. Clin. Rheumatol.* 17.1(2003):151-166.
Hansen et al. "Comparison of Clinical Grade Type 1 Polarized and Standard Matured Dendritic Cells for Cancer Immunotherapy." *Vaccine.* 31.4(2013):639-646.
Hansen et al. "Integrin Binding and Cell Spreading on Extracellular Matrix Act at Different Points in the Cell Cycle to Promote Hepatocyte Growth." *Mol. Biol. Cell.* 5(1994):967-975.
Harris et al. "Open Pore Biodegradable Matrices Formed with Gas Foaming." *J. Biomed. Mater. Res.* 42.3(1998):396-402.
Harrison. "What is the Status of Reaction-Diffusion Theory Thirty-Four Years After Turing?" *J. Theor. Biol.* 125.4(1987):369-384.
Hartgerink et al. "Peptide-Amphiphile Nanofibers: A Versatile Scaffold for the Preparation of Self-Assembling Materials." *PNAS.* 99.8(2002):5133-5138.
Hartmann et al. "CpG DNA: A Potent Signal for Growth, Activation, and Maturation of Human Dendritic Cells." *PNAS.* 96(1999):9305-9310.
Hashimoto et al. "Development of Alginate Wound Dressings Linked with Hybrid Peptides Derived from Laminin and Elastin." *Biomaterials.* 25.7-8(2004)1407-1414.
Hawke et al. "Myogenic Satellite Cells: Physiology to Molecular Biology." *J. Appl. Physiol.* 91(2001):534-551.
Helm et al. "Synergy Between Interstitial Flow and VEGF Directs Capillary Morphogenesis in vitro Through a Gradient Amplification Mechanism." *PNAS.* 102.44(2005):15779-15784.
Henry et al. "The VIVA Trial: Vascular Endothelial Growth Factor in Ischemia for Vascular Angiogenesis." *Circulation.* 107.10(2003):1359-1365.

(56) References Cited

OTHER PUBLICATIONS

Hermanson. *Bioconjugate Techniques.* New York: Academic Press. (1996):152-185.
Heslop et al. "Transplanted Primary Neonatal Myoblasts can Give Rise to Functional Satellite Cells as Identified Using the Myf5nlacZl+ Mouse." *Gene Ther.* 8(2001):778-783.
Hildner et al. "Batf3 Deficiency Reveals a Critical Role for CD8α+ Dendritic Cells in Cytotoxic T Cell Immunity." *Science.* 322. 5904(2008):1097-1100.
Hill et al. "Designing Scaffolds to Enhance Transplanted Myoblast Survival and Migration." *Tissue Engin.* 12.5(2006):1295-1304.
Hill et al. "Muscle Satellite (Stem) Cell Activation During Local Tissue Injury and Repair." *J. Anat.* 203.1(2003):89-99.
Hill. "Macroporous Scaffold Architecture, Peptide, HGF/FGF and Myoblast Incorporation Enhance Myogenesis." *IADR/AADR/CADR 83rd General Session.* (Mar. 9-12, 2005). Poster #2829.
Hirano et al. "Peptide and Protein Presenting Materials for Tissue Engineering." *Adv. Mat.* 16.1(2004):17-25.
Hodge-Dufour et al. "Inhibition of Interferon γ Induced Interleukin 12 Production: A Potential Mechanism for the Anti-Inflammatory Activities of Tumor Necrosis Factor," *PNAS.* 95.23(1998):13806-13811.
Hodi et al. "Immunologic and Clinical Effects of Antibody Blockade of Cytotoxic T Lymphocyte-Associated Antigen 4 in Previously Vaccinated Cancer Patients." *PNAS.* 105.8(2008):3005-3010.
Horsley et al. "IL-4 Acts as a Myoblast Recruitment Factor During Mammalian Muscle Growth." *Cell.* 113.4(2003):483-494.
Hsiong et al. "Differentiation Stage Alters Matrix Control of Stem Cells." *J. Biomed. Mater. Res. Part A.* 8(2007):145-156.
Huang et al. "Fabrication and in vitro Testing of Polymeric Delivery Systems for Condensed DNA." *J. Biomed. Mater. Res.* 67(2003):1384-1392.
Huang et al. "Long-Term In Vivo Gene Expression via Delivery of PEI-DNA Condensates From Porous Polymer Scaffolds." *Hum. Gene Ther.* 16.5(2005):609-617.
Hubbell et al. "Materials Engineering for Immunomodulation." *Nature.* 462(2009):449-460.
Hubbell. "Biomaterials in Tissue Engineering." *BioTech.* 13(1995):565-576.
Huebsch et al. "Harnessing Traction-Mediated Manipulation of the Cell/Matrix Interface to Control Stem-Cell Fate." *Nat. Mater.* 9.6(2010):518-526.
Ishihara et al. "Roles of Bradykinin in Vascular Permeability and Angiogenesis in Solid Tumor." *Int. Immunopharmacol.* 2.4(2002):499-509.
Jain. "Molecular Regulation of Vessel Maturation." *Nat. Med.* 9.6(2003):685-693.
Jain. "The Manufacturing Techniques of Various Drug Loaded Biodegradable Poly(lactide-co-glycolide) (PLGA) Devices." *Biomater.* 21.23(2000):2475-2490.
Jankovic et al. "In the Absence of IL-12, CD4+ T Cell Responses to Intracellular Pathogens Fail to Default to a Th2 Pattern and are Host Protective in an IL-10-/- Setting." *Immunity.* 16.3(2002):429-439.
Jego et al. "Plasmacytoid Dendritic Cells Induce Plasma Cell Differenetiation Through Type I Interferon and Interleukin 6." *Immunity.* 19.2(2003):225-234.
Jiang et al. "Self-Organization of Periodic Patterns by Dissociated Feather Mesenchymal Cells and the Regulation of Size, Number and Spacing of Primorida." *Development.* 126.22(1999):4997-5009.
Jinushi et al. "Enhancing the Clinical Activity of Granulocyte-Macrophage Colony-Stimulating Factor-Secreting Tumor Cell Vaccines." *Immunol. Rev.* 222(2008):287-298.
Jinushi et al. "MFG-E8-Mediated Uptake of Apoptotic Cells by APCs Links the Pro- and Antiinflammatory Activities of GM-CSF." *J. Clin. Invest.* 117.7(2007):1902-1913.
Johnson et al. "Activation of Skeletal Muscle Satellite Cells and the Role of Fibroblast Growth, Factor Receptors." *Exp. Cell Res.* 219.2(1995):449-453.

Kanzler et al. "Therapeutic Targeting of Innate Immunity with Toll-Like Receptor Agaonists and Antagonists." *Nat. Med.* 13.5(2007):552-559.
Kawai et al. "Innate Immune Recognition of Viral Infection." *Nat. Immunol.* 7.2(2006):131-137.
Kawashima et al. "Pulmonary Delivery of Insulin With Nebulized DL-Lactide/Glycolide Copolymer (PLGA) Nanospheres to Prolong Hypoglycemic Effect." *J. Control. Release.* 62.12(1999):279-287.
Kim et al. "An Overview of Cartilage Tissue Engineering." *Yonsei Med. J.* 41.6(2000):766-773.
Kinoshita et al. "Successive Injections in MDX Mice of Myoblasts Grown with bFGF." *Neuromusc. Disord.* 6.3(1996):187-193.
Kisak et al. "The Vesosome—A Multicompartment Drug Delivery Vehicle." *Curr. Med. Chem.* 11.2(2004):199-219.
Klebanoff et al. "CD8+ T-Cell Memory in Tumor Immunology and Immunotherapy." *Immunol. Rev.* 211(2006):214-224.
Klinman. "Immunotherapeutic Uses of CpG Oligodeoxynucleotides." *Nat. Rev. Immunol.* 4.4(2004):249-258.
Kondo et al. "A Reaction-Diffusion Wave on the Skin of the Marine Angelfish *Pomacanthus.*" *Nature.* 376(2002):765-768.
Kong et al. "Controlling Rigidity and Degradation of Alginate Hydrogels via Molecular Weight Distribution." *Biomacromolec.* 5.5(2004):1720-1727.
Kong et al. "Designing Alginate Hydrogels to Maintain Viability of Immobilized Cells." *Biomat.* 24.22(2003):4023-4029.
Kong et al. "Non-Viral Gene Delivery Regulated by Stiffness of Cell Adhesion Substrates." *Nat. Mater.* 4(2005):406-410.
Krieg. "Development of TLR9 Agonists for Cancer Therapy." *J. Clin. Invest.* 117.5(2007):1184-1194.
Krishnamachari et al. "PLGA Microparticles that Co-Deliver Antigen and Toll Like Receptor Ligand Adjuvants for Applications in Cancer Immunotherapy." AAPS Pharmaceutica. Nov. 11, 2009. Web. Mar. 1, 2013. http://abstracts.aapspharmaceutica.com/ExpoAAPS09/CC/forms/attendee/index.aspx?content=sessionInfo&sessionId=2716.
Kumar et al. "Toll-Like Receptors and Innate Immunity." *Biochem. Biophys. Res. Commun.* 388.4(2009):621-625.
Kurts et al. "CD8 T Cell Ignorance or Tolerance to Islet Antigens Depends on Antigen Dose." *PNAS.* 96.22(1999):12703-12707.
Kwon et al. "In vivo Targeting Dendritic Cells for Activation of Cellular Immunity Using Vaccine Carriers Based on pH-Responsive Microparticles." *PNAS.* 102.51(2005):18264-18268.
Langer et al. "Tissue Engineering." *Science.* 260(1993):920-926.
Lanzavecchia et al. "Regulation of T Cell Immunity by Dendritic Cells." *Cell.* 106.3(2001):263-266.
Leach et al. "Coating of VEGF-Releasing Scaffolds with Bioactive Glass for Angiogenesis and Bone Regeneration." *Biomater.* 27.17(2006):3249-3255.
Lee et al. "Hydrogel Formation via Vell Crosslinking." *Adv. Mat.* 15.21(2003):1828-1832.
Lee et al. "Hydrogels for Tissue Engineering." *Chem. Rev.* 101. 7(2001):1869-1879.
Lefaucheur et al. "The Cellular Events of Injured Muscle Regeneration Depend on the Nature of the Injury." *Neuromusc. Disorders.* 5.6(1995):501-509.
Lensch et al. "Scientific and Clinical Opportunities for Modeling Blood Disorders With Embyronic Stem Cells." *Blood.* 107. 7(2006):2605-2612.
Leshem et al. "Hepatocyte Growth Factor (HGF) Inhibits Skeletal Muscle Cell Differentiation: A Role for the bHLH Protein Twist and the cdk Inhibitor p27." *J. Cell. Physiol.* 184(2000):101-109.
Li et al. "Effect of Growth Factors and Extracellular Matrix Materials on the Proliferation and Differentiation of Microencapsulated Myoblasts." *J. Biomater. Sci. Polym. Ed.* 14.6(2003):533-549.
Li et al. "Effects of Three-Dimensional Scaffolds on Cell Organization and Tissue Development." *Biotech. Bioprocess Eng.* 6.5(2001):311-325.
Li. "TNF-α is a Mitogen is Skeletal Muscle." *Am. J. Physiol. Cell Physiol.* 285(2003):C370-C376.
Lipton et al. "Developmental Fate of Skeletal Satellite Cells." *Science.* 205(1979):1292-1294.
Liu. "Dendritic Cell Subsets and Lineages, and Their Functions in Innate and Adaptive Immunity." *Cell.* 106.3(2001):259-262.

(56) References Cited

OTHER PUBLICATIONS

Lu et al. "Muscle-Derived Stem Cells Seeded Into Acellular Scaffolds Develop Calcium-Dependent Contractile Activity That is Modulated by Nicotinic Receptors." *Urology.* 61(2003):1285-1291.
Lubeck. "The Costs of Musculoskeletal Disease: Health Needs Assessment and Health Economics." *Best Pract. Res. Clin. Rheumatol.* 17.3(2003):529-539.
Lumelsky et al. "Differentiation of Embryonic Stem Cells to Insulin-Secreting Structures Similar to Pancreatic Islets." *Science.* 292.5520(2001):1389-1394.
Mach et al. "Differences in Dendritic Cells Stimulated in Vivo by Tumors Engineered to Secrete Granulocyte-Macrophage Colony-Stimulating Factor or Flt3-Ligand." *Cancer Res.* 60.12(2000):3239-3246.
Magram et al. "IL-12-Deficient Mice are Defective but not Devoid of Type 1 Cytokine Responses." *Ann. N.Y. Acad. Sci.* 795(1996):60-70.
Maini. "Spatial and Spatio-Temporal Patterns in a Cell-Haptotaxis Model." *J. Math. Biol.* 27.5(1989):507-522.
Maley et al. "Extracellular Matrix, Growth Factors, Genetics: Their Influence on Cell Proliferation and Myotube Formation in Primary Cultures of Adult Mouse Skeletal Muscle." *Exp. Cell Res.* 219.1(1995):169-179.
Martinsen et al. "Alginate as Immobilization Material." *Biotech. Bioeng.* 33.1(1989):79-89.
Massia et al. "An RGD Spacing of 440 nm is Sufficient for Integrin $\alpha v\beta 3$-Mediated Fibroblast Spreading and 140 nm for Focal Contact and Stress Fiber Formation." *J. Cell Biol.* 114.5(1991):1089-1100.
Matthew et al. "Subperiosteal Behaviour of Alginate and Cellulose Wound Dressing Materials." *Biomaterials.* 16.4(1995):275-278.
McKinney-Freeman et al. "Muscle-Derived Hematopoietic Stem Cells are Hematopoietic in Origin." *PNAS.* 99.3(2002):1341-1346.
McPherron et al. "Regulation of Skeletal Muscle Mass in Mice by a New TGF-$\beta$. Superfamily Member." *Nature.* 387(1997):83-90.
Melero-Martin et al. "Engineering Robust and Functional Vascular Networks In Vivo With Human Adult and Cord Blood-Derived Progenitor Cells." *Circ. Res.* 103.2(2008):194-202.
Mellman et al. "Dendritic Cells: Specialized and Regulated Antigen Processing Machines." *Cell.* 106.3(2001):255-258.
Menetrey et al. "Suturing Versus Immobilization of a Muscle Laceration: A Morphological and Functional Study in a Mouse Model." *Am. J. Sports Med.* 27.2(1999):222-229.
Meyer et al. "Clinical Investigations of Toll-Like Receptor Agonists." *Expert Opin. Investig. Drugs.* 17.7(2008):1051-1065.
Meylan et al. "Intracellular Pattern Recognition Receptors in the Host Response." *Nature.* 442.7098(2006):39-44.
Miller et al. "Hepatocyte Growth Factor Affects Satellite Cell Activation and Differentiation in Regenerating Skeletal Muscle." *Am. J. Physiol. Cell Physiol.* 278(2000):C174-C181.
Mitchell et al. "The Exogenous Administration of Basic Fibroblast Growth Factor to Regenerating Skeletal Muscle in Mice Does Not Enhance the Process of Regeneration." *Growth Factors.* 13.1-2(1996):37-55.
Moioli et al. "Matrices and Scaffolds for Drug Delivery in Dental, Oral and Craniofacial Tissue Engineering." *Adv. Drug Deliv. Rev.* 59.4-5(2007):308-324.
Mooney et al. "Switching From Differentiation to Growth in Hepatocytes: Control by Extracellular Matrix." *J. Cell. Phys.* 151.3(1992):497-505.
Moser et al. "Dendritic Cell Regulation of TH1-TH2 Regulation." *Nat. Immunol.* 1.3(2000):199-205.
Naik et al. "Development of Plasmacytoid and Conventional Dendritic Cell Subtypes From Single Precursor Cells Derived in vitro and in vivo." *Nat. Immunol.* 8.11(2007):1217-1226.
Nair et al. "Polymers as Biomaterials for Tissue Engineering and Controlled Drug Delivery." *Adv. Biochem. Eng. Biotechnol.* 102(2006):47-90.
NCBI Accession No. NM_000758, Apr. 1, 2012.
NCBI Accession No. NM_003265, Dec. 30, 2012.
NCBI Accession No. NM_017442, Apr. 14, 2012.
NCBI Accession No. NP_000749.2, Apr. 1, 2012.
NCBI Accession No. NP_001020537, Jan. 30, 2011.
NCBI Accession No. NP_001020538, Jan. 30, 2011.
NCBI Accession No. NP_001020539, Jan. 30, 2011.
NCBI Accession No. NP_001020540, Jan. 30, 2011.
NCBI Accession No. NP_001028928, Jan. 30, 2011.
NCBI Accession No. NP_003367, Jan. 30, 2011.
NCBI Accession No. NP_059138, Apr. 14, 2012.
Nehls et al. "A Novel, Microcarrier-Based in Vitro Assay for Rapid and Reliable Quantification of Three-Dimensional Cell Migration and Angiogenesis." *Microvasc. Res.* 50.3(1995):311-322.
Noguera-Troise et al. "Blockade of Dll4 Inhibits Tumour Growth by Promoting Non-Productive Angiogenesis." *Nature.* 444.7122(2006):1032-1037.
O'Garra et al. "Are Dendritic Cells Afraid of Commitment?" *Nat. Immunol.* 5.12(2004):1206-1208.
O'Shea et al. "Type 1 IFNs and Regulation of TH1 Responses: Enigmas Both Resolved and Emerge." *Nat. Immunol.* 1.1(2000):17-19.
Ohlstein et al. "The Stem Cell Niche: Theme and Variations." *Curr. Opin. Cell Biol.* 16.6(2004):693-699.
Oldenburg et al. "TLR13 Recognizes Bacterial 23S rRNA Devoid of Erythromycin Resistance-Forming Modification." *Science.* 337.6098(2012):1111-1115.
Oldenhove et al. "Decrease of Foxp3+ Treg Cell Number and Acquisition of Effector Cell Phenotype During Lethal Infection." *Immunity.* 31.5(2009):772-786.
Ota et al. "Percutaneous Subxiphoid Access to the Epicardium Using a Miniature Crawling Robotic Device." *Innovations.* 1.5(2006):227-231.
Overwijk et al. "Tumor Regression and Autoimmunity After Reversal of a Functionally Tolerant State of Self-Reactive CD8+ T Cells." *J. Exp. Med.* 198.4(2003):569-580.
Ozawa et al. "Microenvironmental VEGF Concentration, Not Total Dose, Determines a Threshold Between Normal and Aberrant Angiogenesis." *J. Clin. Invest.* 113.4(2004):516-527.
Padilla et al. "Insufficient TLR Activation Contributes to the Slow Development of CD8+ T Cell Responses in *Trypanosoma cruzi* Infection." *J. Immunol.* 183(2009):1245-1252.
Palacio et al. "Interleukin 10 and Tumor Necrosis Factor $\alpha$ Gene Expression in Respiratory and Peripheral Muscles." *Arch. Bronconeumol.* 38.7(2002):311-316. (Spanish Original and English Abstract).
Partridge et al. "Conversion of mdx Myofibres From Dystrophin-Negative to -Positive by Injection of Normal Myoblasts." *Nature.* 337(1989):176-179.
Pelinkovic et al. "Tissue Engineering and Gene Therapy of the Muscoskeletal System with Muscle Cells." *Z. Orthop. Ihre Grenzgeb.* 138.5(2000):402-406. (German Original and English Abstract).
Peters et al. "Engineering Vascular Networks in Porous Polymer Matrices." *J. Biomed. Mater. Res.* 60.4(2002):668-678.
Phillippi. "Patterning of Multiple Cell Lineages from a Single Stem Cell Population." *Annual Meeting of the American Society for Cell Biology.* (Dec. 10, 2006).
Pluen et al. "Role of Tumor-Host Interactions in Interstitial Diffusion of Macromolecules: Cranial vs. Subcutaneous Tumors." *PNAS.* 98.8(2001):4628-4633.
Pooyan et al. "Conjugates Beating Multiple Formyl-Methionyl Peptides Display Enhanced Binding to, but not Activation of Phagocytic Cells." *Bioconjugate Chem.* 13.2(2002):216-223.
Pope et al. "Organ-Specific Regulation of the CD8 T Cell Response to *Listeria monocytogenes* Infection." *J. Immunol.* 166(2001):3402-3409.
Pouzet et al. "Factors Affecting Functional Outcome After Autologous Skeletal Myoblast Transplantation." *Ann. Thorac. Surg.* 71(2001):844-851.
Pulendran et al. "Flt3-Ligand and Granulocyte Colony-Stimulating Factor Mobilize Distinct Human Dendritic Cell Subsets In Vivo." *J. Immunol.* 165(2000):566-572.
Qu et al. "Development of Approaches to Improve Cell Survival in Myoblast Transfer Therapy." *J. Cell Biol.* 142.5(1998):1257-1267.

(56) References Cited

OTHER PUBLICATIONS

Qu-Petersen et al. "Identification of a Novel Population of Muscle Stem Cells in Mice: Potential for Muscle Regeneration." *J. Cell Biol.* 157.5(2002):851-864.
Quezada et al. "CTLA4 Blockade and GM-CSF Combination Immunotherapy Alters the Intratumor Balance of Effector and Regulatory T Cells." *J. Clin. Invest.* 116.7(2006):1935-1945.
Rajagopalan et al. "Regional Angiogenesis With Vascular Endothelial Growth Factor in Peripheral Arterial Disease: A Phase II Randomized, Double-Blind, Controlled Study of Adenoviral Delivery of Vascular Endothelial Growth Factor 121 in Patients With Disabling Intermittent Claudication." *Circulation.* 108.16(2003):1933-1938.
Randolph et al. "Migration of Dendritic Cell Subsets and Their Precursors." *Annu. Rev. Immunol.* 26(2008):293-316.
Rappolee et al. "Macrophage-Derived Growth Factors." *Curr. Top. Microbiol. Immunol.* 181(1992):87-140.
Rapraeger. "Syndecan-Regulated Receptor Signaling." *J. Cell. Biol.* 149.5(2000):995-998.
Reddy et al. "Exploiting Lymphatic Transport and Complement Activation in Nanoparticle Vaccines." *Nat. Biotechnol.* 25.10(2007):1159-1164.
Reimann et al. "Satellite Cells in Normal and Regenerated Soleus Muscles of mdx and Control Mice." *Eur. J. Neurosci.* 10(1998):366. (Abstract #153.07).
Richards Grayson et al. "Multi-Pulse Drug Delivery From a Resorbable Polymeric Microchip Device." *Nat. Mater.* 2.11(2003):767-772.
Richardson et al. "Polymeric System for Dual Growth Factor Delivery." *Nat. Biotech.* 19.11(2001):1029-1034.
Riddle et al. "Role of Poly(lactide-co-glycolide) Particle Size on Gas-Foamed Scaffolds." *J. Biomater. Sci. Polym. Ed.* 15.12(2004):1561-1570.
Ridgway et al. "Inhibition of Dll4 Signalling Inhibits Tumour Growth by Deregulating Angiogenesis." *Nature.* 444.7122(2006):1083-1087.
Rinderknecht et al. "The Amino Acid Sequence of Human Insulin-Like Growth Factor I and its Structural Homology with Proinsulin." *J. Biol. Chem.* 253.8(1978):2769-2776.
Rosenberg et al. "Cancer Immunotherapy: Moving Beyond Current Vaccines." *Nat. Med.* 10.9(2004):909-915.
Roth et al. "SC68896, a Novel Small Molecule Proteasome Inhibitor, Exerts Antiglioma Activity In vitro and In vivo." *Clin. Cancer Res.* 15.21(2009):6609-6618.
Rowlands et al. "Directing Osteogenic and Myogenic Differentiation of MSCs: Interplay of Stiffness and Adhesive Ligand Presentation." *Am. J. Physiol Cell Physiol.* 295(2008):1037-1044.
Rowley et al. "Alginate Type and RGD Density Control Myoblast Phenotype." *J. Biomed. Mater. Res.* 60.2(2002):217-233.
Rowley et al. "Biomaterials to Spatially Regulate Cell Fate." *Adv. Mater.* 14.12(2002):886-889.
Rowley. "Alginate Hydrogels as Synthetic Extracellular Matrix Materials." *Biomaterials.* 20.1(1999):45-53.
Rubin et al. "Dissociation of Heparan Sulfate and Receptor Binding Domains of Hepatocyte Growth Factor Reveals That Heparan Sulfate-c-Met Interaction Facilitates Signaling." *J. Biol. Chem.* 276.35(2001):32977-32983.
Ryten et al. "ATP Regulates the Differentiation of Mammalian Skeletal Muscle by Activation of a P2X5 Receptor on Satellite Cells." *J. Cell. Biol.* 158.2(2002):345-355.
Ryu et al. "The Construction of Three-Dimensional Micro-Fluidic Scaffolds of Biodegradable Polymers by Solvent Vapor Based Bonding of Micro-Molded Layers." *Biomaterials.* 28.6(2007):1174-1184.
Salvador et al. "Combination of Immune Stimulating Adjuvants With Poly(lactide-co-glycolide) Microspheres Enhances the Immune Response of Vaccines." *Vaccine.* 30.3(2011):589-596.
Sano et al. "Swift Development of Protective Effector Functions in Naive CD8+ T Cells Against Malaria Liver Stages." *J. Exp. Med.* 194.2(2001):173-179.
Sansonetti. "The Innate Signaling of Dangers and the Dangers of Innate Signaling." *Nat. Immunol.* 7.12(2006):1237-1242.
Saxena et al. "Skeletal Muscle Tissue Engineering Using Isolated Myoblasts on Synthetic Biodegradable Polymers: Preliminary Studies." *Tissue Eng.* 5.6(1999):525-532.
Schaefer et al. Innate mmunity in the Human Female Reproductive Tract: Antiviral Response of Uterine Epithelial Cells to TLR3 Agonist Poly(I:C). *J. Immunol.* 174(2005):992-1002.
Schijns et al. "Mice Lacking IL-12 Develop Polarized Th1 Cells During Viral Infection." *J. Immunol.* 160(1998):3958-3964.
Schnorrer et al. "The Dominant Role of CD8+ Dendritic Cells in Cross-Presentation is not Dictated by Antigen Capture." *PNAS.* 103.28(2006):10729-10734.
Schuler et al. "The Use of Dendritic Cells in Cancer Immunotherapy." *Curr. Opin. Immunol.* 15.2(2003):138-147.
Seale et al. "Pax7 Is Required for the Specification of Myogenic Satellite Cells." *Cell.* 102.6(2000):777-786.
Shansky et al. "Letter to the Editor: A Simplified Method for Tissue Engineering Skeletal Muscle Organoids In Vitro." *In Vitro Cell. Dev. Biol.* 33(1997):659-661.
Shakweh et al. "Design and Characterisation of Poly(lactide-co-glycolide) Small Particulate Systems for the Delivery of Immunostimulant CpG Oligonucleotide." *J. Nanosci. Nanotechnol.* 6.9-10(2006):2811-2820.
Sheehan et al. "Skeletal Muscle Satellite Cell Proliferation in Response to Members of the Fibroblast Growth Factor Family and Hepatocyte Growth Factor." *J. Cell. Physiol.* 181.3(1999):499-506.
Sheridan et al. "Bioabsorbable Polymer Scaffolds for Tissue Engineering Capable of Sustained Growth Factor Delivery." *J. Control. Release.* 64.1-3(2000):91-102.
Shi et al. "A Novel Toll-Like Receptor that Recognizes Vascular Stomatitis Virus." *J. Biol. Chem.* 286.6(2011):4517-4524.
Shortman et al. "Steady-State and Inflammatory Dendritic-Cell Development." *Nat. Rev. Immunol.* 7(2007):19-30.
Sick et al. "WNT and DKK Determine Hair Follicle Spacing Through a Reaction-Diffusion Mechanism." *Science.* 314.5804(2006):1447-1450.
Silva et al. "Spatiotemporal Control of Vascular Endothelial Growth Factor Delivery From Injectable Hydrogels Enhances Angiogenesis." *J. Thromb. Haemost.* 5.3(2007):590-598.
Skokos et al. "CD8-DCs Induce IL-12-Independent Th1 Differentiation Through Delta 4 Notch-Like Ligand in Response to Bacterial LPS." *J. Exp. Med.* 204.7(2007):1525-1531.
Skuk et al. "Efficacy of Myoblast Transplantation in Nonhuman Primates Following Simple Intramuscular Cell Injections: Toward Defining Strategies Applicable to Humans." *Exp. Neurol.* 175.1(2002):112-126.
Skuk et al. "Myoblast Transplantation: The Current Status of a Potential Therapeutic Tool for Myopathies." *J. Musc. Res. Cell. Motil.* 24.4-6(2003):285-300.
Smidsrød et al. "Alginate as Immobilization Matrix for Cells." *Trends Biotechnol.* 8.3(1990):71-78.
Sohier et al. "Critical Factors in the Design of Growth Factor Releasing Scaffolds for Cartilage Tissue Engineering." *Exp. Opin. Drug Deliv.* 5.5(2008):543-566.
Steinman et al. "Taking Dendritic Cells into Medicine." *Nature.* 449.7161(2007):419-426.
Storrie et al. "Sustained Delivery of Plasmid DNA From Polymeric Scaffolds for Tissue Engineering." *Adv. Drug Deliv. Rev.* 58.4(2006):500-514.
Straub et al. "Animal Models for Muscular Dystrophy Show Different Patterns of Sarcolemmal Distruption." *J. Cell Biol.* 139.2(1997):375-385.
Sun et al. "Sustained Vascular Endothelial Growth Factor Delivery Enhances Angiogenesis and Perfusion in Ischemic Hind Limb." *Pharm. Res.* 22.7(2005):1110-1116.
Takeshita et al. "Therapeutic Angiogenesis." *J. Clin. Invest.* 93.2(1994):662-670.
Tamura et al. "Immunotherapy of Tumors with Autologous Tumor-Derived Heat Shock Protein Preparations." *Science.* 278.3(1997):117-120.

(56) References Cited

OTHER PUBLICATIONS

Tatsumi et al. "HGF/SF Is Present in Normal Adult Skeletal Muscle and Is Capable of Activating Satellite Cells." *Dev. Biol.* 194.1(1998):114-128.
Thurston et al. "The Delta Paradox: DLL4 Blockade Leads to More Tumour Vessels but Less Tumour Growth." *Nat. Rev. Cancer.* 7.5(2007):327-331.
Tidball. "Inflammatory Cell Response to Acute Muscle Injury." *Med. Sci. Sports Exerc.* 27.7(1995):1022-1032.
Turing. "Discussion: Turing's Theory of Morphogenesis—It's Influence on Modelling Biological Pattern and Form." *Bull. Math. Biol.* 52.1-2(1990):119-159.
Turing. "The Chemical Basis of Morphogenesis." *Philosophical Transactions of the Royal Society of London. Series B.* 237.641(1952):37-72.
Uchida et al. "Immunization by Particle Bombardment of Antigen-Loaded poly-(DL-lactide-co-glycolide) Microspheres in Mice." *Vaccine.* 12(2006):2120-2130.
Urbanek et al. "Stem Cell Niches in the Adult Mouse Heart." *PNAS.* 103.24(2006):9226-9231.
van Duin et al. "Triggering TLR Signaling in Vaccination." *Trends Immunol.* 27.1(2006):49-55.
Vandenburgh et al. "Tissue-Engineered Skeletal Muscle Organoids for Reversible Gene Therapy." *Hum. Gene Ther.* 17(1996):2195-2200.
Vieira et al. "The Bulk of Endogenously Produced IgG2a is Eliminated From the Serum of Adult C57BL/6 Mice With a Half-Life of 6-8 Days." *Eur. J. Immunol.* 16.7(1986):871-874.
Vieira et al. "The Half-Lives of Serum Immunoglobulins in Adult Mice." *Eur. J. Immunol.* 18.2(1988):313-316.
Villadangos et al. "Intrinsic and Cooperative Antigen-Presenting Functions of Dendritic-Cell Subsets in vivo." *Nat. Rev. Immunol.* 7.7(2007):543-555.
Villadangos. "Presentation of Antigens by MHC Class II Molecules: Getting the Most Out of Them." *Molec. Immunol.* 38.5(2001):329-346.
von Dassow et al. "The Segment Polarity Network is a Robust Developmental Module." *Nature.* 406.6792(2000):188-192.
Wakim et al. "Dendritic Cell-Induced Memory T Cell Activation in Nonlymphoid Tissues." *Science.* 319(2008):198-202.
Waldron-Lynch et al. "Advances in Type 1 Diabetes Therapeutics: Immunomodulation and β-Cell Savage." *Endocrinol. Metab. Clin. North Am.* 38.2(2009):303-317.
Wan et al. "Peritoneal Macrophage Uptake, Pharmacokinetics and Biodistribution of Macrophage-Targeted PEG-fMLF (N-Formyl-Methionyl-Leucyl-Phenylalanine) Nanocarriers for Improving HIV Drug Delivery." *Pharm. Res.* 24.11(2007):2110-2119.
Wang et al. "Biological Activity of Bevacizumab, a Humanized Anti-VEGF Antibody in vitro." *Angiogenesis.* 7.4(2004):335-345.
Wei et al. "Global Mapping of H3K4me3 and H3K27me3 Reveals Specificity in Plasticity in Lineage Fate Determination of Differentiating CD4+ T Cells." *Immunity.* 30.1(2009):155-167.
Wernig et al. "Function of Skeletal Muscle Tissue Formed After Myoblast Transplantation into Irradiated Mouse Muscles." *J. Physiol.* 522.2(2000):333-345.
White et al. "Leukemia Inhibitory Factor Enhances Regeneration in Skeletal Muscles After Myoblast Transplantation." *Musc. Nerve.* 24.5(2001):695-697.
World Health Organization. "Global Burden of Musculoskeletal Disease Revealed in new WHO Report." *Bull. World Health Organ.* 81.11(2003):853-854.
World Health Organization. "The World Health Report 2004: Changing History." *The World Health Report.* (2004):1-169.
Wright et al. "Muscle-Based Gene Therapy and Tissue Engineering for the Musculoskeletal System." *Drug Disc. Today.* 6.14(2001):728-733.
Yancopoulos et al. "Vascular-Specific Growth Factors and Blood Vessel Formation." *Nature.* 407.6801(2000):242-248.

Yuen et al. "Mimicking Nature by Codelivery of Stimulant and Inhibitor to Create Temporally Stable and Spatially Restricted Angiogenic Zones." *PNAS.* 107.42(2010):17933-17938.
Zammit et al. "Kinetics of Myoblast Proliferation Show That Resident Satellite Cells are Competent to Fully Regenerate Skeletal Muscle Fibers." *Exp. Cell Res.* 281.1(2002):39-49.
Zammit et al. "Muscle Satellite Cells Adopt Divergent Fates: A Mechanism for Self-Renewal?" *J. Cell Biol.* 166.3(2004):347-357.
Zeltinger et al. "Effect of Pore Size and Void Fraction on Cellular Adhesion, Proliferation, and Matrix Deposition." *Tissue Eng.* 7.5(2001):557-572.
Zhao et al. "Active Scaffolds for On-Demand Drug and Cell Delivery." *PNAS.* 108.1(2011):67-72.
Zhao et al. "Directed Cell Migration via Chemoattractants Released from Degradable Microspheres." *Biomat.* 26(2005):5048-5063.
Zhou et al. "Microstructure and Mechanical Properties of Poly(L-lactide) Scaffolds Fabricated by Gelatin Particle Leaching Method." *J. Appl. Polymer Sci.* 98(2005):1373-1379.
"Wound Management: Past, Present, and Future." *Clinicians' Pocket Guide to Chronic Wound Repair.* Mulder et al., eds. Springhouse, PA: Springhouse Corporation. (1998):85-90.
Anderson et al. "Biomaterial Microarrays: Rapid, Microscale Screening of Polymer-Cell Interaction." *Biomaterials.* 26.23(2005):4892-4897.
Anderson et al. "Nanoliter-Scale Synthesis of Arrayed Biomaterials and Application to Human Embryonic Stem Cells." *Nat. Biotechnol.* 22.7(2004):863-866.
Balakrishna et al. "Structural Correlates of Antibacterial and Membrane-Permeabilizing Activities in Acylpolyamines." *Antimicrob. Agents Chemother.* 50.3(2006):852-861.
Bachem et al. "Superior Antigen Cross-Presentation and XCR1 Expression Define Human $CD11c^+ CD141^+$ Cells as Homologues of Mouse $CD8^+$ Dendritic Cells." *J. Exp. Med.* 207.6(2010):1273-1281.
Bar-Cohen et al. "Electroactive Polymer Actuators and Sensors." *MRS Bullet.* 33.3(2008):173-181.
Bates. "Improved Muscle Regeneration by Combining VEGF With IGF1." *Regen. Med.* 5.6(2010):853-854.
Beaucage et al. "The Functionalization of Oligonucleotides Via Phosphoramidite Derivatives." *Tetrahedron.* 49.10(1993):1925-1963.
Beebe et al. "Functional Hydrogel Structures for Autonomous Flow Control Inside Microfluidic Channels." *Nature.* 404(2000):588-590.
Bekiari et al. "Study of Poly(N,N-dimethylacrylamide)/CdS Nanocomposite Organic/Inorganic Gels." *Langmuir.* 20.19(2004):7972-7975.
Blumenthal et al. "Polyurethane Scaffolds Seeded with Genetically Engineered Skeletal Myoblasts: A Promising Tool to Regenerate Myocardial Function." *Artificial Organs.* 34.2(2010):E46-E54.
Brinkmann et al. "Neutrophil Extracellular Traps Kill Bacteria." *Science.* 303.5663(2004):1532-1535.
Calvert. "Electroactive Polymer Gels." *Electroactive Polymer (EAP) Acutators as Artificial Muscle: Reality, Potential, and Challenges.* Bar-Cohen, ed. Bellingham, WA: Spie Press. (2004):151-170.
Calvert. "Gel Sensors and Actuators." *MRS Bullet.* 33.3(2008):207-212.
Conconi et al. "In vitro and in vivo Evaluation of Acellular Diaphragmatic Matrices Seeded with Muscle Precurosrs Cells and Coated with VEGF Silica Gel to Repair Muscle Defect of the Diaphram." *J. Biomed. Mater. Res.* 89A.2(2009):304-316.
Coulson et al. "Flow of Fluids through Granular Beds and Packed Columns." *Chemical Engineering.* New York: Pergamon Press. 2(1978):125-171.
Crameri et al. "Improved Green Fluorescent Protein by Molecular Evolution Using DNA Shuffling." *Nat. Biotechnol.* 14.3(1996):315-319.
Doan et al. "Subcellular Localization of a Sporulation Membrane Protein is Achieved Through a Network of Interactions Along and Across the Septum." *Mol. Microbiol.* 55.6(2005)1767-1781.
Egholm et al. "Peptide Nucleic Acids (PNA). Oligonucleotide Analogues with an Achiral Peptide Backbone." *J. Am. Chem. Soc.* 114.5(1992):1895-1897.

(56) References Cited

OTHER PUBLICATIONS

Egholm et al. "PNA Hybridizes to Complementary Oligonucleotides Obeying the Watson-Crick Hydrogen-Bonding Rules." *Nature.* 365.6446(1993):566-568.
Falsey et al. "Peptide and Small Molecule Microarray for High Throughput Cell Adhesion and Functional Assays." *Bioconjug. Chem.* 12.3(2001):346-353.
Fischer et al. "A Brilliant Monomeric Red Fluorescent Protein to Visualize Cytoskeleton Dynamics in Dictyostelium." *FEBS Lett.* 577.1-2(2004):227-232.
Fischer et al. "Visualizing Cytoskeleton Dynamics in Mammalian Cells Using a Humanized Variant of Monomeric Red Fluorescent Protein." *FEBS Lett.* 580.10(2006):2495-2502.
Fox. "Management of Worsening Multiple Sclerosis with Mitoxantrone: A Review." *Clin. Ther.* 28.4(2006):461-474.
GenBank Accession No. AAI44040, Mar. 18, 2009.
GenBank Accession No. CAG29322.1, Oct. 16, 2008.
GenBank Accession No. CAG33149.1, Oct. 21, 2008.
GenBank Accession No. EF064765.1, Nov. 13, 2006.
Glasbey et al. "Image Analysis and Three-Dimensional Modelling of Pores in Soil Aggregates." *Eur. J. Soil Sci.* 42.2(1991):479-486.
Gupta et al. "Magnetically Controlled Targeted Micro-Carrier Systems." *Life Sci.* 44.3(1989):175-186.
Heath. "Cells for Tissue Engineering." *Trends Biotechnol.* 18.1(2006):17-19.
Iwamoto et al. "Preparation of an Ionic Polymer Gel Microactuator and Measurement of its Periodic Motions." *Nippon Kagaku Kaishi.* 9(1997):609-614. (Japanese Original and English Abstract).
Juntanon et al. "Electrically Controlled Release of Sulfosalicylic Acid from Crosslinked Poly(Vinyl Alcohol) Hydrogel." *Int. J. Pharm.* 356(2008):1-11.
Khownium et al. "Novel Endotoxin-Compounds with Terephthalaldehyde-bis-guanyllhydrazone Scaffolds." *Bioorg. Med. Chem. Lett.* 16(2006):1305-1308.
Kim et al. "The Effect of VEGF on the Myogenic Differentiation of Adipose Tissue Derived Stem Cells Within Thermosensitive Hydrogel Matrices." *Biomaterials.* 31.6(2010)1213-1218.
Kwon et al. "Electrically Erodible Polymer Gel for Controlled Release of Drugs." *Nature.* 354(1991):291-293.
Lao et al. "Magnetic and Hydrogel Composite Materials for Hyperthermia Applications." *J. Mater. Sci. Mater. Med.* 15.10(2004):1061-1064.
Lauterbach et al. "Mouse CD8α$^+$ DCs and Human BDCA3$^+$ DCs are Major Producers of IFN-λ in Response to Poly IC." *J. Exp. Med.* 207.12(2010):2703-2717.
Letsinger et al. "Phosphoramidate Analogs of Oligonucleotides." *J. Org. Chem.* 35.11(1970):3800-3803.
Liu et al. "Nanostructured Materials Designed for Cell Binding and Transduction." *Biomacromolecules.* 2.2(2001):362-368.
López et al. "Magnetic Applications of Polymer Gels." *Macromol. Symp.* 166.1(2001):173-178.
Meier et al. "Peptide Nucleic Acids (PNAs)—Unusual Properties of Noionic Oligonucleotide Analogues." *Angew. Chem. Int. Ed.* 31.8(1992):1008-1010.
Meraz et al. "Mesoporous Silicon Particles for the Presentation of Tumor Antigens and Adjuvant for Anti-Cancer Immunity." *Cancer Res.* 71.S24(2011):159s-160s. (Abstract #P1-01-12).
Miller et al. "Lipopolysaccharide Sequestrants: Structural Correlates of Activity and Toxicity in Novel Acylhomospermines." *J. Med. Chem.* 48(2005):2589-2599.
Miyata et al. "Biomolecule-Sensitive Hydrogels." *Adv. Drug Deliv. Rev.* 54.1(2002):79-98.
Murdan. "Electro-Responsive Drug Delivery from Hydrogels." *J. Control. Release.* 92(2003):1-17.
Nagai et al. "A Variant of Yellow Fluorescent Protein with Fast and Efficient Maturation for Cell-Biological Applications." *Nat. Biotechnol.* 20.1(2002):87-90.
NCBI Accession No. NM_004119, Apr. 14, 2013.
NCBI Accession No. NM_006274.2, Mar. 31, 2013.
Niamlang et al. "Electrically Controlled Release of Salicylic Acid from poly(p-phenylene vinylene) Polyacrylamide Hydrogels." *Int. J. Pharm.* 371(2009):126-133.
Orner et al. "Arrays for the Combinatorial Exploration of Cell Adhesion." *J. Am. Chem. Soc.* 126.35(2004):10808-10809.
Paradee et al. "Effects of Crosslinking Ratio, Model Drugs, and Electric Field Strength on Electrically Controlled Release for Alginate-Based Hydrogels." *J. Mater. Sci. Mater. Med.* 23(2012):999-1010.
Parker et al. "Effect of Mitoxantrone on Outcome of Children with First Relapse of Acute Lymphoblastic Leukemia (ALL R3): An Open-Label Radomised Trial." *Lancet.* 376(2010):2009-2017.
Porter et al. "Separation of Natural Populations of Coliform Bacteria from Freshwater and Sewage by Magnetic-Bead Cell Sorting." *J. Microbiol. Meth.* 33.3(1998):221-226.
Qui et al. "Environment-Sensitive Hydrogels for Drug Delivery." *Adv. Drug Deliv. Rev.* 53.3(2001):321-339.
Rhoads et al. "Satellite Cell-Mediated Angiogenesis in vitro Coincides with a Functional Hypoxia-Inducible Factor Pathway." *Am. J. Physiol. Cell Physiol.* 296.6(2009):C1321-C1328.
Rizzo et al. "An Improved Cyan Fluorescent Protein Variant Useful for FRET." *Nat. Biotechnol.* 22.4(2004):445-449.
Salvay et al. "Inductive Tissue Engineering with Protein and DNA-Releasing Scaffolds." *Mol. Biosyst.* 2.1(2006):36-48.
Shaner et al. "Improved Monomeric Red, Orange and Yellow Fluorescent Proteins Derived from *Discosoma* sp. Red Fluorescent Protein." *Nat. Biotechnol.* 22.12(2004):1567-1572.
Takahashi et al. "Induction of Pluripotent Stem Cells from Adult Human Fibroblasts by Defined Factors." *Cell.* 131.5(2007):861-872.
Tanaka et al. "Collapse of Gels in an Electric Field." *Science.* 218(1982):467-469.
Ten Dijke et al. "Growth Factors for Wound Healing." *Nat. Biotechnol.* 7(1989):793-798.
Tomer et al. "Electrically Controlled Release of Macromolecules from Cross-Linked Hyaluronic Acid Hydrogels." *J. Control. Release.* 33.3(1995):405-413.
Tourniaire et al. "Polymer Microarrays for Cellular Adhesion." *Chem. Commun.* 20(2006):2118-2120.
Tsien. "The Green Fluorescent Protein." *Annu. Rev. Biochem.* 67(1998):509-544.
Wang et al. "Evolution of New Nonantibody Proteins via Iterative Somatic Hypermutation." *PNAS.* 101.48(2004):16745-16749.
Xie et al. "Preparation and Application of Surface-Coated Superparamagnetic Nanobeads in the Isolation of Genomic DNA." *J. Magn. Magnetic Mater.* 277.1(2004):16-23.
Yu et al. "Induced Pluripotent Stem Cell Lines Derived from Human Somatic Cells." *Science.* 318.5858(2007):1917-1920.
Yuk et al. "Electric Current-Sensitive Drug Delivery System Using Sodium Alginate/Polyacrylic Acid Composites." *Pharm. Res.* 9.7(1992):955-957.
Alsberg et al. "Regulating Bone Formation via Controlled Scaffold Design." *J. Dent. Res.* 82.11(2003):903-908.
Augst et al. "Alginate Hydrogels as Biomaterials." *Macromol. Biosci.* 6(2006):623-633.
Bouhadir et al. "Degradation of Partially Oxidized Alginate and its Potential Application for Tissue Engineering." *Biotechnol. Prog.* 17.5(2001):945-950.
Bryant et al. "Photo-Patterning of Porous Hydrogels for Tissue Engineering." *Biomater.* 28.19(2007):2978-2986.
Kong et al. "Controlling Degradation of Hydrogels via the Size of Crosslinked Junctions." *Adv. Mater.* 16.21(2004):1917-1921.
Kong et al. "Decoupling the Dependence of Rheological/Mechanical Properties of Hydrogels from Solids Concentration." *Polymer.* 43(2002):6239-6246.
Kong et al. "Design of Biodegradable Hydrogel for the Local and Sustained Delivery of Angiogenic Plasmid DNA." *Pharma. Res.* 25.5(2008):1230-1238.
Langenkamp et al. "Kinetics of Dendritic Cell Activation: Impact on Priming of $T_H1$, $T_H2$ and Nonpolarized T Cells." *Nat. Immunol.* 1.4(2000):311-316.
Leor et al. "Cells, Scaffolds, and Molecules for Myocardial Tissue Engineering." *Pharmacol. Therapeutics.* 105(2005):151-163.

(56) References Cited

OTHER PUBLICATIONS

Lutolf et al. "Repair of Bone Defects Using Synthetic Mimetics of Collagenous Extracellular Matrices." *Nat. Biotechnol.* 21.5(2003):513-518.

Pedersen et al. "Induction of Regulatory Dendritic Cells by Desamethasone and 1α,25-Dihydroxyvitamin D3." *Immunol. Lett.* 91(2004):63-69.

Reis e Sousa. "Activation of Dendritic Cells: Translating Innate into Adaptive Immunity." *Curr. Opin. Immunol.* 16.1(2005):21-25.

Silva et al. "Material-Based Deployment Enhances Efficacy of Endothelial Progenitor Cells." *PNAS.* 105.38(2008):14347-14352.

Dar et al. "Optimization of Cardiac Cell Seeding and Distribution in 3D Porous Alginate Scaffolds." *Biotechnol. Bioeng.* 80(2002):305-312.

Marui et al. "Simultaneous Application of Basic Fibroblast Growth Factor and Hepatocyte Growth Factor to Enhance the Blood Vessels Formation." *J. Vasc. Surg.* 41.1(2005):82-90.

Mohan et al. "Novel Porous, Polysaccharide Scaffolds for Tissue Engineering Applications." *Trends Biomater. Artif. Organs.* 18.2(2005):219-224.

Ohashi et al. "Surgical Excision Combined with Autologous Whole Tumor Cell Vaccination is an Effective Therapy for Murine Neuroblastoma." *J. Ped. Surg.* 41(2006):1361-1368.

Shoichet et al. "Stability of Hydrogels Used in Cell Encapsulation: An In Vitro Comparison of Alginate and Agarose." *Biotechnol. Bioeng.* 50(1996):374-381.

Corcione et al. "CCL19 and CXCL12 trigger in vitro chemotaxis of human mantle cell lymphoma B cells." *Clin CancerRes.* Feb. 1, 2004;10(3):964-71.

Latorre et al. "Applications of magnetic nanoparticles in medicine: magnetic fluid hyperthermia." *P R Health Sci J.* Sep. 2009;28(3):227-38.

Malhotra et al. "Use of an oncolytic virus secreting GM-CSF as combined oncolytic and immunotherapy for treatment of colorectal and hepatic adenocarcinomas." *Surgery.* Apr. 2007;141(4):520-9.

Nestle et al. "Vaccination of melanoma patients with peptide- or tumor lysate-pulsed dendritic cells." *Nat Med.* Mar 1998;4(3):328-32.

Sato, "Human dendritic cells." *Biotherapy.* Nov. 2004;18(6):467-77.

Wang et al. "Photothermal effects of supramolecularly assembled gold nanoparticles for the targeted treatment of cancer cells." *Angew Chem Int Ed Engl.* May 17 2010;49(22):3777-81.

Yang et al., "The effect of incorporating RGD adhesive peptide in polyethylene glycol diacrylate hydrogel on osteogenesis of bone marrow stromal cells." *Biomaterials.* 26(2005):5991-5998.

"Collagen: The Fibrous Proteins of the Matrix." *Molecular Cell Biology.* Lodish et al., eds. New York: W.H. Freeman. Section 22.3(2000):979-985.

"Transient." Merriam-Webster Dictionary. Web. Jul. 18, 2014. www.merriam-webster.com/dictionary/transient.

Agache et al. "Mechanical Properties and Young's Modulus of Human Skin in Vivo." *Arch. Dermatol. Res.* 269.3(1980):221-232.

Aguado et al. "Improving Viability of Stem Cells During Syringe Needle Flow Through the Design of Hydrogel Cell Carriers." *Tissue Eng. Part A.* 18.7-8(2012):806-815.

Akpalo et al. "Fibrin-Polyethylene Oxide Interpenetrating Polymer Networks: New Self-Supported Biomaterials Combining the Properties of Both Protein Gel and Synthetic Polymer." *Acta Biomater.* 7.6(2011):2418-2427.

American Diabetes Association. "Standards of Medical Care in Diabetes—2013." *Diabetes Care.* 36.S1(2013):S11-S66.

Annaidh et al. "Characterization of the Anistropic Mechanical Properties of Excised Human Skin." *J. Mech. Behav. Biomed. Mater.* 5.1(2012):139-148.

Aschner et al. "Metabolic Memory for Vascular Disease in Diabetes." *Diabetes Technol. Ther.* 14.S1(2012):S68-S74.

Aubin et al. "Directed 3D Cell Alignment and Elongation in Microengineered Hydrogels." *Biomater.* 31.27(2010):6941-6951.

Babensee et al. "Host Response to Tissue Engineered Device." *Adv. Drug Deli. Rev.* 33.1-2(1998):111-139.

Becker et al. "Cytological Demonstration of the Clonal Nature of Spleen Colonies Derived from Transplanted Mouse Marrow Cells." *Nature.* 197(1963):452-454.

Bell. "Models for the Specific Adhesion of Cells to Cells." *Science.* 200.4342(1978):618-627.

Bencherif et al. "Influence of Cross-Linker Chemistry on Release Kinetics of PEG-co-PGA Hydrogels." *J. Biomed. Mater. Res. A.* 90.1(2009):142-153.

Bencherif et al. "End-Group Effects on the Properties of PEG-co-PGA Hydrogels." *Acta Biomater.* 5.6(2009):1872-1883.

Bencherif et al. "Influence of the Degree of Methacrylation of Hyaluronic Acid Hydrogels Properties." *Biomater.* 29.12(2008):1739-1749.

Bencherif et al. "Injectable Preformed Scaffolds with Shape-Memory Properties." *PNAS.* 109.48(2012):19590-19595.

Bencherif et al. "Nanostructured Hybrid Hydrogels Prepared by a Combination of Atom Transfer Radical Polymerization and Free Radical Polymerization." *Biomater.* 30.29(2009):5270-5278.

Bencherif et al. "Synthesis by AFET ATRP of Degradable Nanogel Precursors for in situ Formation of Nanostructured Hyaluronic Acid Hydrogel." *Biomacromol.* 10.9(2009):2499-2507.

Benton et al. "Photocrosslinking of Gelatin Macromers to Synthesize Porous Hydrogels that Promote Valvular Interstitial Cell Function." *Tissue Eng. Part A.* 15.11(2009):3221-3230.

Berg et al. "IL-10 is a Central Regulator of Cyclooxygenase-2 Expression and Prostaglandin Production." *J. Immunol.* 166.4(2001):2674-2680.

Bergstraesser et al. "Stimulation and Inhibition of Human Mammary Epithelial Cell Duct Morphogenesis In Vitro." *Proc. Assoc. Am. Physicians.* 108.2(1996):140-154.

Bianco et al. "The Meaning, the Sense and the Significance: Translating the Science of Mesenchymal Stem Cells into Medicine." *Nat. Med.* 19.1(2013):35-42.

Bilodeau et al. "Regular Pyramid Punch Problem." *J. Appl. Mech.* 59.3(1992):519-523.

Boateng et al. "Wound Healing Dressings and Drug Delivery Systems: A Review." *J. Pharm. Sci.* 97.8(2008):2892-2923.

Boerckel et al. "Mechanical Regulation of Vascular Growth and Tissue Regeneration in vivo." *PNAS.* 108.37(2011):E674-E680.

Boontheekul et al. "Controlling Alginate Gel Degradation Utilizing Partial Oxidation and Bimodal Molecular Weight Distribution." *Biomaterials.* 26.15(2005):2455-2465.

Brignone et al. "A Phase I Phamacokinetic and Biological Correlative Study of IMP321, a Novel MHC Class II Agonist, in Patients with Advanced Renal Cell Carcinoma." *Clin. Cancer Res.* 15.19(2009):6225-6231.

Broxmeyer et al. "Insights into the Biology of Cord Blood Stem/Progenitor Cells." *Cell Prolif.* 44.S1(2011):55-59.

Buckwalter et al. "Form of Antigen Dictates Immunity: Irradiated Cell vs. Whole Cell Lysate Vaccination." *J. Immunol.* 178(2007).

Bullard et al. "Fetal Wound Healing: Current Biology." *World J. Surg.* 27.1(2003):54-61.

Buonaguro et al. "Translating Tumor Antigens into Cancer Vaccines." *Clin. Vaccine Immunol.* 18.1(2011):23-34.

Burdick et al. "Controlled Degradation and Mechanical Behavior of Photopolymerized Hyaluronic Acid Networks." *Biomacromol.* 6.1(2005):386-391.

Burdick et al. "Photoencapsulation of Osteoblasts in Injectable RGD-Modified PEG Hydrogels for Bone Tissue Engineering." *Biomater.* 23.22(2002):4315-4323.

Bégué et al. "Vaccination Against Human Papillomavirus. Implementation and Efficacy Against Cervical Cancer Control." *Bull. Acad. Natl. Med.* 191.9(2007):1805-1816. (French original and English abstract).

Bürger et al. "Effect of VEGF and its Receptor Antagonist SU-5416, an Inhibitor of Angiogenesis, on Processing of the β-amyloid Precursor Protein in Primary Neuronal Cells Derived From Brain Tissue of Tg2576 Mice." *Int. J. Dev. Neurosci.* 28.7(2010):597-604.

Cameron et al. "The Influence of Substrate Creep on Mesenchymal Stem Cell Behaviour and Phenotype." *Biomater.* 32.26(2011):5979-5993.

(56) References Cited

OTHER PUBLICATIONS

Caulfield et al. "Regulation of Major Histocompatibility Complex Class II Antigens on Human Alveolar Macrophages by Granulocyte-Macrophage Colony-Stimulating Factor in the Presence of Glucocorticoids." *Immunol.* 98.1(1999):104-110.
Ceriello et al. "The 'Metabolic Meory': Is more than just Tight Glucose Control Necessary to Prevent Diabetic Complications?" *J. Clin. Endocrinol. Metab.* 94.2(2009):410-415.
Ceriello et al. "The Emerging Challenge in Diabetes: The 'Metabolic Memory.'" *Vascular Pharmacol.* 57.5-6(2012):133-138.
Chan et al. "Traction Dynamics of Filopodia on Compliant Substrates." *Science.* 322.5908(2008):1687-1691.
Chang. "Mouse Models for Studies of Retinal Degeneration and Diseases," *Methods Mol. Biol.* 935(2013):27-39.
Chen et al. "Adipogenic Differentiation of Adipose Tissue-Derived Human Mesenchymal Stem Cells: Effects of Gastric Bypass Surgery." *Surg. Endosc.* 26(2012):3449-3456.
Chen et al. "Functional Human Vascular Network Generated in Photocrosslinkable Gelatin Methacrylate Hydrogels." *Adv. Funct. Mater.* 22.10(2012):2027-2039.
Chiang et al. "Whole Tumor Antigen Vaccines." *Semin. Immunol.* 22.3(2010):132-143.
Choi et al. "In Vitro Mineralization by Preosteoblasts in Poly(DL-lactide-co-glycolide) Inverse Opal Scaffolds Reinforced with Hydrozyapatite Nanoparticles." *Langmuir.* 26.14(2010):12126-12131.
Choi et al. "Three-Dimentional Scaffolds for Tissue Engineering: The Importance of Uniformity in Pore Size and Structure." *Langmuir.* 26.24(2010):19001-19006.
Chou et al. "Characterization of Photocross Linked Alginate Hydrogels for Nucleus Pulposus Cell Encapsulation." *J. Biomed. Mater. Res. A.* 91A.1(2009):187-194.
Clark et al. "Myosin II and Mechanotransduction: A Balancing Act." *Trends Cell Biol.* 17.4(2007):178-186.
Comisar et al. "Engineering RGD Nanopatterned Hydrogels to Control Preosteoblast Behavior: A Combined Computational and Experimental Approach." *Biomaterials.* 28(2007):4409-4417.
Cook et al. "A Sialomucopeptide Liberated by Trypsin from the Human Erythrocyte." *Nature.* 188(1960):1011-1012.
Cooper. "Metabolic Memory: Implications for Diabetic Vascular Complications." *Pediatr. Diabetes.* 10.5(2009):343-346.
Cuda et al. "In Vitro Actin Filament Sliding Velocities Produced by Mixtures of Different Types of Myosin." *Biophys. J.* 72.4(1997):1767-1779.
Cukierman et al. "Taking Cell-Matrix Adhesions to the Third Dimension." *Science.* 294.5547(2001):1708-1712.
David et al. "The in vitro Desensitization of Sensitive Cells by Trypsin." *J. Exp. Med.* 120(1964):1189-1200.
Davies et al. "Antibody-Antigen Complexes." *Annu. Rev. Biochem.* 59(1990):439-473.
de Jong et al. "Regulation of Notch Signaling Genes During BMP2-Induced Differentiation of Osteoblast Precursor Cells."*Biochem. Biophys. Res. Commun.*320(2004):100-107.
Dembo et al. "Stresses at the Cell-to-Substrate Interface During Locomotion of Fibroblasts." *Biophys. J.* 76.4(1999):2307-2316.
Dexter et al. "Conditions Controlling the Proliferation of Haemopoietic Stem Cells In Vitro." *J. Cell. Physiol.* 91.3(1977):335-344.
Di Nicola et al. "Human Bone Marrow Stromal Cells Suppress T-Lymphocyte Proliferation Induced by Cellular or Nonspecific Mitogenic Stimuli." *Blood.* 99.10(2002):3838-3843.
Diduch et al. "Two Cell Lines from Bone Marrow tht Differ in Terms of Collagen Synthesis, Osteogenic Characteristics, and Matrix Mineralization." *J. Bone Joint Surg. Am.* 75.1(1993):92-105.
Diridollou et al. "Skin Ageing: Changes of Physical Properties of Human Skin in vivo." *J. Cosmet. Sci.* 23.6(2001):353-362.
Discher et al. "Tissue Cells Feel and Respond to the Stiffness of their Substrate." *Science.* 310.5751(2005):1139-1143.
Disis et al. "Granulocyte-Macrophage Colony-Stimulating Factor: An Effective Adjuvant for Protein and Peptide-Based Vaccines." *Blood.* 88.1(1996):202-210.

Donati et al. "New Hypothesis on the Role of Alternating Sequences in Calcium-Alginate Gels." *Biomacromol.* 6.2(2005):1031-1040.
Douay et al. "Ex vivo Production of Human Red Blood Cells from Hematopoietic Stem Cells: What is the Future in Transfusion?" *Transfus. Med. Rev.* 21.2(2007):91-100.
Dranoff. "GM-CSF-Based Cancer Vaccines." *Immunol. Rev.* 188(2002):147-154.
DuFort et al. "Balancing Forces: Architectural Control of Mechanotransduction." *Nat. Rev. Mol. Cell Biol.* 12.5(2011):308-319.
Dupont et al. "Role of YAP/TAZ in Mechanotransduction." *Nature.* 474.7350(2011):179-183.
Edwards et al. "Evaluation of Biomechanical Properties of Human Skin." *Clin. Dermatol.* 13.4(1995):375-380.
Eming et al. "Inflammation in Wound Repair: Molecular and Cellular Mechanisms." *J. Invest. Dermatol.* 127.3(2007):514-525.
Engler et al. "Microtissue Elasticity: Measurements by Atomic Force Microscopy and its Influence on Cell Differentiation." *Methods Cell. Biol.* 83(2007):521-545.
Engler et al. "Substrate Compliance Versus Ligand Density in Cell on Gel Response." *Biophys. J.* 86.1 Pt1(2004):617-628.
Exposito et al. "The Fibrallar Collagen Family." *Int. J. Mol. Sci.* 11.2(2010):407-426.
Falanga. "Wound Healing and its Impairment in the Diabetic Foot." *Lancet.* 366.9498(2005):1736-1743.
Fauquemberque et al. "HLA-A*0201-Restricted CEA-Derived Peptide CAP1 is not a Suitable Target for T-Cell-Based Immunotherapy." *J. Immunother.* 33.4(2010):402-413.
Fisher et al. "The Study of Protein Mechanics with the Atomic Force Microscope." *Trends Biochem. Sci.* 24.10(1999):379-384.
Friedenstein et al. "Fibroblast Precursors in Normal and Irradiated Mouse Hematopoietic Organs." *Exp. Hematol.* 4.5(1976):267-274.
Gardel et al. "Traction Stress in Focal Adhesions Correlates Biphasically with Actin Retrograde Flow Speed." *J. Cell Biol.* 183. 6(2008):999-1005.
Gasic et al. "Removal and Regeneration of the Cell Coating in Tumour Cells." *Nature.* 196(1962):170.
Gauthier et al. "Temporary Increase in Plasma Membrane Tension Coordinates the Activation of Exocytosis and Contraction During Cell Spreading." *PNAS.* 108.35(2011):14467-14472.
Geerligs et al. "Linear Viscoelastic Behavior of Subcutaneous Adipose Tissue." *Biorheol.* 45.6(2008):677-688.
GenBank Accession No. AAA36738.1, Aug. 3, 1993.
GenBank Accession No. AAA60022.1, Jan. 7, 1995.
GenBank Accession No. AAA64239.1, Mar. 23, 1995.
GenBank Accession No. AAB18786.3, Jul. 12, 1999.
GenBank Accession No. AAH94877.1, May 20, 2005.
GenBank Accession No. AEO22039.1, Sep. 17, 2011.
GenBank Accession No. AF344424.1, Apr. 8, 2002.
GenBank Accession No. AF414120.1, Sep. 26, 2001.
GenBank Accession No. AF450242.1, Feb. 11, 2002.
GenBank Accession No. AJ583695.1, Oct. 7, 2008.
GenBank Accession No. AY291313.1, Apr. 26, 2004.
GenBank Accession No. BC094887.1, Jul. 21, 2006.
GenBank Accession No. CAA01955.1, Nov. 14, 2006.
GenBank Accession No. DQ103757.1, Jul. 25, 2005.
GenBank Accession No. JN602184.1, Sep. 17, 2011.
GenBank Accession No. M16006.1, Jan. 7, 1995.
GenBank Accession No. M24902.1, Jan. 7, 1995.
GenBank Accession No. M73239.1, Mar. 23, 1995.
GenBank Accession No. NM_000091.4, May 10, 2014.
GenBank Accession No. NM_000572.2, May 18, 2014.
GenBank Accession No. NM_000638.3, May 4, 2014.
GenBank Accession No. NM_000758.3, May 4, 2014.
GenBank Accession No. NM_000885.4, Apr. 13, 2014.
GenBank Accession No. NM_000963.3, Jun. 13, 2014.
GenBank Accession No. NM_001001522.1, May 18, 2014.
GenBank Accession No. NM_001845.4, May 3, 2014.
GenBank Accession No. NM_001901.2, May 18, 2014.
GenBank Accession No. NMM_002421.3_05112014.
GenBank Accession No. NM_002982.3, May 3, 2014.
GenBank Accession No. NM_003377.4, May 5, 2014.
GenBank Accession No. NM_003392.4, May 5, 2014.

(56) References Cited

OTHER PUBLICATIONS

GenBank Accession No. NM_004469.4, May 25, 2014.
GenBank Accession No. NM_005429.3, Mar. 31, 2014.
GenBank Accession No. NM_015719.3, Feb. 26, 2014.
GenBank Accession No. NP_000082.2, May 10, 2014.
GenBank Accession No. NP_000629.3, May 4, 2014.
GenBank Accession No. NP_000749.2, May 4, 2014.
GenBank Accession No. NP_000876.3, Apr. 13, 2014.
GenBank Accession No. NP_000954.1, Jun. 13, 2014.
GenBank Accession No. NP_001001522.1, May 18, 2014.
GenBank Accession No. NP_001836.2, May 3, 2014.
GenBank Accession No. NP_001892.1, May 18, 2014.
GenBank Accession No. NP_002973.1, May 3, 2014.
GenBank Accession No. NP_003239.2, Feb. 18, 2014.
GenBank Accession No. NP_003368.1, May 5, 2014.
GenBank Accession No. NP_003383.2, May 5, 2014.
GenBank Accession No. NP_004460.1, May 25, 2014.
GenBank Accession No. NP_005420.1, May 11, 2014.
GenBank Accession No. NP_056534.2, Feb. 26, 2014.
GenBank Accession No. U76381.2, Jul. 12, 1999.
Genes et al. "Effect of Substrate Mechanics on Chondrocyte Adhesion to Modified Alginate Surfaces." *Arch. Biochem. Biophys.* 422.2(2004):161-167.
Graessley. "Entangled Linear, Branched and Network Polymer Systems—Molecular Theories." *Adv. Poly. Sci.* 47(1982):67-117.
Guillaume et al. "Two Abundant Proteasome Subtypes that Uniquely Process Some Antigens Presented by HLA Class I Molecules." *PNAS.* 107.43(2010):18599-18604.
Guo et al. "Droplet Microfluidics for High-Throughput Biological Assays." *Lab Chip.* 12.12(2012):2146-2155.
Gurkan et al. "The Mechanical Environment of Bone Marrow: A Review." *Ann. Biomed. Eng.* 36.12(2008):1978-1991.
Halim et al. "Biologic and Synthetic Skin Substitutes: An Overview." *Indian J. Plast. Surg.* 43(2010):S23-S28.
Harris. "Classification, Diagnostic Criteria, and Screening for Diabetes." *Diabetes in America.* NIH Publication No. 95-1468. Chapter 2. (1995):15-36.
Holland et al. "Transforming Growth Factor-β1 Release from Oligo(poly(ethylene glycol) Fumarate) Hydrogels in Conditions that Model the Cartilage Wound Healing Environment." *J. Control. Release.* 94(2004):101-114.
Humphries et al. "Integrin Ligands at a Glance." *J. Cell. Sci.* 119.Pt19(2006):3901-3903.
Huston et al. "Protein Engineering of Antibody Binding Sites: Recovery of Specific Activity in an Anti-Digoxin Single-Chain Fv Analogue Produced in *Escherichia coli.*" *PNAS.* 85.16(1988):5879-5883.
Hutson et al. "Synthesis and Characterization of Tunable Poly(ethylene Glycol): Gelatin Methacrylate Composite Hydrogels." *Tissue Eng. Part A.* 17.13-14(2011):1713-1723.
Hwang et al. "Fabrication of Three-Dimensional Porous Cell-Laden Hydrogel for Tissue Engineering." *Biofabrication.* 2.3(2010):035003.
Ihnat et al. "Hypothesis: The 'Metabolic Memory', the New Challenge of Diabetes." *Diabet. Med.* 24.6(2007)582-586.
Isern et al. "Self-Renewing Human Bone Marrow Mesenspheres Promote Hematopoietic Stem Cell Expansion." *Cell Rep.* 3.5(2013):1714-1724.
Janmey et al. "From Tissue Mechanics to Transcription Factors." *Differentiation.* 86.3(2013):112-120.
Jiang et al. "Two-Piconewton Slip Bond Between Fibronectin and the Cytoskeleton Depends on Talin." *Nature.* 424.6946(2003):334-337.
Jokinen et al. "Integrin-Mediated Cell Adhesion to Type I Collagen Fibrils." *J. Biol. Chem.* 279.30(2004):31956-31963.
Jugdutt et al. "Aging and Defective Healing, Adverse Remodeling, and Blunted Post-Conditioning in the Reperfused Wounded Heart." *J. Am. Coll. Cardiol.* 51.14(2008):1399-1403.
Kang et al. "Effect of Porous Structure on the Degradation of Freeze-Dried Gelatin Hydrogels." *J. Bioact. Compat. Poly.* 14.4(1999):331-343.

Katayama et al. "Integrated Analysis of the Genome and the Transcriptome by FANTOM." *Brief Bioinform.* 5.3(2004):249-258.
Kearney et al. "Macroscale Delivery Systems for Molecular and Cellular Payloads." *Nat. Mater.* 12.11(2013):1004-1017.
Kennedy et al. "Rapid and Extensive Collapse from Electrically Responsive Macroporous Hydrogels." *Adv. Healthc. Mater.* 3.4(2014):500-507.
Khetan et al. "Degradation-Mediated Cellular Traction Directs Stem Cell Fate in Covalently Crosslinked Three-Dimensional Hydrogels." *Nat. Mater.* 12.5(2013):458-465.
Kim et al. "Multifunctional Capsule-in-Capsules for Immunoprotection and Trimodal Imaging." *Angew. Chem. Int. Ed.* 50.10(2011):2317-2321.
Klein et al. "Cell-Cycle Control by Physiological Matrix Elasticity and In Viivo Tissue Stiffening." *Curr. Biol.* 19.18(2009):1511-1518.
Kohane. "Microparticles and Nanoparticles for Drug Delivery." *Biotechnol. Bioeng.* 96.2(2007):203-209.
Kong et al. "FRET Measurements of Cell-Traction Forces and Nano-Scale Clustering of Adhesion Ligands Varied by Substrate Stiffness." *PNAS.* 102.12(2005):4300-4305.
Kratky et al. "Direct Activation of Antigen-Presenting Cells is Required for CD8+ T-Cell Priming and Tumor Vaccination." *PNAS.* 108.42(2011):17414-17419.
Kuwahara et al. "Cell Delivery Using an Injectable and Adhesive Transglutaminase-Gelatin Gel." *Tissue Eng. Part C Methods.* 16.4(2010):609-618.
Lee et al. "Intravenous hMSCs Improve Myocardial Infarction in Mice because Cells Embolized in Lung are Activated to Secrete the Anti-Inflammatory Protein TSG-6." *Cell Stem Cell.* 5.1(2009):54-63.
Lee et al. "Engineering Liver Tissue Spheroids with Inverted Colloidal Crystal Scaffolds." *Biomater.* 30.27(2009):4687-4694.
Lele et al. "Investigating Complexity of Protein-Protein Interactions in Focal Adhesions." *Biochem. Biophys. Res. Commun.* 369.3(2008):929-934.
Levental et al. "Soft Biological Materials and their Impact on Cell Function." *Soft Matter.* 3(2007):299-306.
Li et al. "A Novel Cyclohexene Derivate, Ethyl (6R)-6-[N-(2-Chloro-4-fluorophenyl)sulfamoyl]cyclohex-1-ene-1-carboxylate (TAK-242), Selectively Inhibits Toll-Like Receptor 4-Mediated Cytokine Production Through Suppression of Intracellular Signaling." *Mol. Pharmacol.* 69.4(2006):1288-1295.
Li et al. "Purified Hybrid Cells from Dendritic Cell and Tumor Cell Fusions are Superior Activators of Antitumor Immunity." *Cancer Immunol. Immunother.* 50.9(2001):456-462.
Lin et al. "Transdermal Regulation of Vascular Network Bioengineering Using a Photopolymerizable Methacrylated Gelatin Hydrogel." *Biomater.* 34.28(2013):6785-6796.
Liu et al. "Heterobifunctional Poly(Ethylene Glycol)-Tethered Bone Morphogenetic Protein-2-Stimulated Bone Marrow Mesenchymal Stromal Cell Differentiation and Osteogenesis." *Tissue Eng.* 13.5(2007)1113-1124.
Liu et al. "On the Viscoelastic Character of Liver Tissue: Experiments and Modelling of the Linear Behaviour." *Biorheol.* 37.3(2000):191-201.
Lo et al. "Cell Movement is Guided by the Rigidity of the Substrate." *Biophys. J.* 79.1(2000):144-152.
Ludewig et al. "Immunotherapy with Dendritic Cells Directed Against Tumor Antigens Shared with Normal Host Cells Results in Severe Autoimmune Disease." *J. Exp. Med.* 191.5(2000):795-804.
Majeti et al. "Identification of a Hierarchy of Multipotent Hematopoietic Progenitors in Human Cord Blood." *Cell Stem Cell.* 1.6(2007):635-645.
Malmqvist. "Biospecific Interaction Analysis Using Biosensor Technology." *Nature.* 361.6408(1993):186-187.
Mammoto et al. "Mechanical Control of Tissue and Organ Development," *Development.* 137.9(2010):1407-1420.
Manayski et al. "Vascular Niche Controls Organ Regeneration." *Circ. Res.* 114.17(2014):1077-1079.
Mansoor et al. "Engineering T Cells for Cancer Therapy." *Br. J. Cancer.* 93.10(2005):1085-1091.

(56) References Cited

OTHER PUBLICATIONS

Masedunskas et al. "Role for the Actomyosin Complex in Regulated Exocytosis Revealed by Intravital Microscopy." *PNAS.* 108.33(2011):13552-13557.
McDonald et al. "Early Fracture Callus Displays a Smooth Muscle-Like Viscoelastic Properties Ex Viivo: Implications for Fracture Healing." *J. Orthop. Res.* 27.11(2009):1508-1513.
McKinnon et al. "Biophysically Defined and Cytocompatible Covalently Adaptable Networks as Viscoelastic 3D Cell Culture Systems." *Adv. Mater.* 26.6(2014):865-872.
McWhorter et al. "Modulation of Macrophage Phenotype by Cell Shape." *PNAS.* 110.43(2013):17253-17258.
Melief et al. "Immunotherapy of Established (Pre)Malignant Disease by Synthetic Long Peptide Vaccines." *Nat. Rev. Cancer.* 8(2008):351-360.
Merkel et al. "Using Mechanobiological Mimicry of Red Blood Cells to Extend Circulation Times of Hydrogel Microparticles." *PNAS.* 108.2(2011):586-591.
Metters et al. "Fundamental Studies of Biodegradable Hydrogels as Cartilage Replacement Materials." *Biomed. Sci. Instrum.* 35(1999):33-38.
Miljkovic et al. "Chondrogenesis, Bone Morphogenetic Protein-4 and Mesenchymal Stem Cells." *Osteoarthritis Cartilage.* 16(2008):1121-1130.
Miller et al. "Melanoma." *N. Engl. J. Med.* 355.1(2006):51-65.
Miralles et al. "Actin Dynamics Control SRF Activity by Regulation of its Coactivator MAL." *Cell.* 113.3(2003):329-342.
Molinari et al. "Modification of Surface Membrane Antigens by Trypsin." *Proc. Soc. Exp. Biol. Med.* 148.4(1975):991-994.
Molloy et al. "Movement and Force Produced by a Single Myosin Head." *Nature.* 378.6553(1995):209-212.
Mooney et al. "Cytoskeletal Filament Assembly and the Control of Cell Spreading and Function by Extracellular Matrix." *J. Cell Sci.* 108(1995):2311-2320.
Muralidharan-Chari et al. "ARF6-Regulated Shedding of Tumor Cell-Derived Plasma Membrane Microvesicles." *Curr. Biol.* 19.22(2009):1875-1885.
NCBI Accession No. NM_001561.5, Mar. 16, 2014.
NCBI Accession No. NM_004448.3, Apr. 23, 2014.
NCBI Accession No. NM_005018.2, Apr. 27, 2014.
NCBI Accession No. NM_181780.3, Jan. 27, 2014.
NCBI Accession No. NP_001193, May 3, 2014.
NCBI Accession No. NP_001552.2, Mar. 16, 2014.
NCBI Accession No. NP_003237.2, May 25, 2014.
NCBI Accession No. NP_003318.1, May 4, 2014.
NCBI Accession No. NP_003327.3, May 4, 2014.
NCBI Accession No. NP_005009.2, Apr. 27, 2014.
NCBI Accession No. NP_861445.3, Jan. 27, 2014.
Nichol et al. "Cell-Laden Microengineered Gelatin Methacrylate Hydrogels." *Biomater.* 31.21(2010):5536-5544.
Nicodemus et al. "Cell Encapsulation in Biodegradable Hydrogels for Tissue Engineering Applications." *Tissue Eng. Part B Rev.* 14.2(2008):149-165.
Niessen et al. "The α6β4 Integrin is a Receptor for Both Lamin and Kalinin." *Exp. Cell Res.* 211.2(1994):360-367.
Osunkoya et al. "Synthesis and Fate of Immunological Surface Receptors on Cultured Burkitt Lymphoma Cells." *Int. J. Cancer.* 4.2(1969):159-165.
Page-McCaw et al. "Matrix Metalloproteinases and the Regulation of Tissue Remodelling." *Nat. Rev. Mol. Cell Biol.* 8.3(2007):221-233.
Pailler-Mattei et al. "In vivo Measurements of the Elastic Mechanical Properties of Human Skin by Indentation Tests." *Med. Eng. Phys.* 30.5(2008):599-606.
Pardoll. "The Blockade of Immune Checkpoints in Cancer Immunotherapy." *Nat. Rev. Cancer.* 12.4(2012):252-264.
Parekh et al. "Modulus-Driven Differentiation of Marrow Stromal Cells in 3D Scaffolds that is Independent of Myosin-Based Cytoskeletal Tension." *Biomater.* 32.9(2011):2256-2264.
Parekkadan et al. "Mesenchymal Stem Cell-Derived Molecules Reverse Fulminant Hepatic Failure." *PLoS One.* 2.9(2007):e941.
Park et al. "Photopolymerized Hyaluronic Acid-Based Hydrogels and Interpenetrating Networks." *Biomater.* 24.6(2003):893-900.
Pawlaczyk et al. "Age-Dependent Biomechanical Properties of the Skin." *Postepy. Dermatol. Alergol.* 30.5(2013):302-306.
Pek et al. "The Effect of Matrix Stiffness on Mesenchymal Stem Cell Differentiation in a 3D Thixotropic Gel." *Biomater.* 31.3(2010):385-391.
Pena et al. "Effects of TGF-β and TGF-β Neutralizing Antibodies on Fibroblast-Induced Collagen Gel Contraction: Implications for Proliferative Vitroretinpathy." *Invest. Ophthalmol. Vis. Sci.* 35.6(1994):2804-2808.
Peyton et al. "The Use of Poly(ethylene glycol) Hydrogels to Investigate the Impact of ECM Chemistry and Mechanics on Smooth Muscle Cells." *Biomater.* 27.28(2006):4881-4893.
Pinho et al. "PDGFRα and CD51 Mark Human Nestin+ Sphere-Forming Mesenchymal Stem Cells Capable of Hematopoietic Progenitor Cell Expansion." *J. Exp. Med.* 210.7(2013):1351-1367.
Qi et al. "Patterned Differentiation of Individual Embryoid Bodies in Spatially Organized 3D Hybrid Microgels." *Adv. Mater.* 22.46(2010):5276-5281.
Qin et al. "Soft Lithography for Micro- and Nanoscale Patterning." *Nat. Protoc.* 5.3(2010):491-502.
Raeber et al. "Molecularly Engineered PEG Hydrogels: A Novel Model System for Proteolyrically Mediated Cell Migration." *Biophys. J.* 89.2(2005):1374-1388.
Ramón-Azcón et al. "Gelatin Methacrylate as a Promising Hydrogel for 3D Microscale Organization and Proliferation of Dielectroretically Patterned Cells." *Lab on a Chip.* 12.16(2012):2959-2969.
Ranganath et al. "Harnessing the Mesenchymal Stem Cell Secretome for the Treatment of Cardiovascular Disease." *Cell Stem Cell.* 10.3(2012):244-258.
Raposo et al. "Extracellular Vesicles: Exosomes, Microvesicles, and Friends." *J. Cell. Biol.* 200.4(2013):373-383.
Roccaro et al. "BM Mesenchymal Stromal Cell-Derived Exosomes Facilitate Multiple Myeloma Progression." *J. Clin. Invest.* 123.4(2013):1542-1555.
Rodriguez et al. "Minimal "Self" Peptides that Inhibit Phagocytic Clearance and Enhance Delivery of Nanoparticles." *Science.* 339.6122(2013):971-975.
Sacchetti et al. "Self-Renewing Osteoprogenitors in Bone Marrow Sinusoids can Organize a Hematopoietic Microenvironment." *Cell.* 131.2(2007):324-336.
Sakai et al. "An Injectable, in situ Enzymatically Gellable, Gelatin Derivative for Drug Delivery and Tissue Engineering." *Biomater.* 30.20(2009):3371-3377.
Scheel et al. "Toll-Like Receptor-Dependent Activation of Several Human Blood Cell Types by Protamine Condensed mRNA." *Eur. J. Immunol.* 35(2005):1557-1566.
Schofield. "The Relationship Between the Spleen Colony-Forming Cell and the Haemopoietic Stem Cell." *Blood. Cells.* 4.1-2(1978):7-25.
Schwartz. "Integrins and Extracellular Matrix in Mechanotransduction." *Cold Spring Harb. Perspect. Biol.* 2.12(2010):a005066.
Sensi et al. "Unique Tumor Antigens: Evidence for Immune Control of Genome Integrity and Immunogenic Targets for T Cell-Mediated Patient-Specific Immunotherapy." *Clin. Cancer Res.* 12.17(2006):5023-5032.
Shi et al. "Granulocyte-Macrophage Colony-Stimulating Factor (GM-CSF) and T-Cell Responses: What we do and don't know." *Cell Res.* 16.2(2006):126-133.
Shin et al. "Contractile Forces Sustain and Polarize Hematopoiesis from Stem and Progenitor Cells." *Cell Stem Cell.* 14.1(2014):81-93.
Shin et al. "Lamins Regulate Cell Trafficking and Lineage Maturation of Adult Human Hematopoetic Cells." *PNAS.* 110.47(2013):18892-18897.
Shin et al. "Myonsin-II Inhibition and Soft 2D Matrix Maximize Multinucleation and Cellular Projections Typical of Platelet-Producing Megakaryocytes." *PNAS.* 108.28(2011):11458-11463.
Siegwart et al. "Synthesis, Characterization, and in vitro Cell Culture Viability of Degradable Poly(N-isopropylacrylamide-co-

(56) References Cited

OTHER PUBLICATIONS 5,6-benzo-2-methylene-1,3-dioxepane)-Based Polymers and Cross-linked Gels." *J. Biomed. Mater. Res. A.* 87.2(2008):345-358.
Silva et al. "Effects of VEGF Temporal and Spatial Presentation on Angiogenesis." *Biomaterials.* 31.6(2010):1235-1241.
Singer et al. "Cutaneous Wound Healing." *N. Engl. J. Med.* 341.10(1999):738-746.
Solon et al. "Fibroblast Adaptation and Stiffness Matching to Soft Elastic Substrates." *Biophys. J.* 93.12(2007):4453-4461.
Stachowiak et al. "Inverse Opal Hydrogel-Collagen Composite Scaffolds as a Supportive Microenvironment for Immune Cell Migration." *J. Biomed. Mater. Res.* 85A(2008):815-828.
Sun et al. "Biomimetic Interpenetrating Polymer Network Hydrogels Based on Methacrylated Alginate and Collagen for 3D Pre-Osteoblast Spreading and Osteogenic Differentiation." *Soft Matter.* 8(2012):2398-2404.
Sun et al. "Highly Stretchable and Tough Hydrogels." *Nature.* 489.7414(2012):133-136.
Suri et al. "Photopatterned Collagen-Hyaluronic Acid Interpenetrating Polymer Network Hydrogels." *Acta Biomater.* 5.7(2009):2385-2397.
Swift et al. "Nuclear Lamin-A Scales with Tissue Stiffness and Enhances Matrix-Directed Differentiation." *Science.* 341.6149(2013):1240104.
Syed et al. "Stem Cell Therapy Market." *Nat. Rev. Drug Discov.* 12.3(2013):185-186.
Tabata et al. "Enhanced Vascularization and Tissue Granulation by Basic Fibroblast Growth Factor Impregnated in Gelatin Hydrogels." *J. Control. Release.* 31.2(1994):189-199.
Tannous. "*Gaussia* Luciferase Reporter Assay for Monitoring Biological Processes in Culture and in vivo." *Nat. Protoc.* 4.4(2009):582-591.
Thomas et al. "Intravenous Infusion of Bone Marrow in Patients Receiving Radiation and Chemotherapy." *N. Engl. J. Med.* 257.11(1957):491-496.
Thurner et al. "Vaccination with Mage-3A1 Peptide-Pulsed Mature, Monocyte-Derived Dendritic Cells Expands Specific Cytotoxic T Cells Induces Regression of Some Metastases in Advanced Stage IV Melanoma." *J. Exp. Med.* 190.11(1999):1669-1678.
Tong et al. "Engineering Interpenetrating Network Hydrogels as Biomimetic Cell Niche with Independently Tunable Biochemical and Mechanical Properties." *Biomater.* 35.6(2014):1807-1815.
Trappmann et al. "Extracelluar-Matrix Tethering Regulates Stem-Cell Fate." *Nat. Mater.* 11.7(2012):642-649.
Trappmann et al. "How Cells Sense Extracellular Matrix Stiffness: A Material's Perspective." *Curr. Opin. Biotechnol.* 24.5(2013):948-953.
Ugarte et al. "Notch Signaling Enhances Osteogenic Differentiation While Inhibiting Adipogenesis in Primary Human Bone Marrow Stromal Cells." *Exp. Hematol.* 37(2009):867-875.
Uhlenbruck. "Action of Proteolytic Enzymes on the Human Erythrocyte Surface." *Nature.* 190(1961):181.
Ulrich et al. "Probing Cellular Mechanobiology in Three-Dimensional Culture with Collagen-Agarose Matrices." *Biomater.* 31.7(2010):1875-1884.
UniProtKB/Swiss-Prot Accession No. P02751.4, Apr. 16, 2014.
UniProtKB/Swiss-Prot Accession No. P02778.2, Jun. 11, 2014.
UniProtKB/Swiss-Prot Accession No. P04626.1, Apr. 16, 2014.
UniProtKB/Swiss-Prot Accession No. P05121.1, Apr. 16, 2014.
UniProtKB/Swiss-Prot Accession No. P05231.1, Jun. 11, 2014.
UniProtKB/Swiss-Prot Accession No. P09038.3, Jun. 11, 2014.
UniProtKB/Swiss-Prot Accession No. P10145.1, Jun. 11, 2014.
UniProtKB/Swiss-Prot Accession No. P13500.1, Jun. 11, 2014.
UniProtKB/Swiss-Prot Accession No. P14210.2, Jun. 11, 2014.
UniProtKB/Swiss-Prot Accession No. P14780.3, Jun. 11, 2014.
UniProtKB/Swiss-Prot Accession No. P14902.1, May 14, 2014.
UniProtKB/Swiss-Prot Accession No. P15692.2, Jun. 11, 2014.
UniProtKB/Swiss-Prot Accession No. P16035.2, Jun. 11, 2014.
UniProtKB/Swiss-Prot Accession No. P16410.3, Apr. 16, 2014.
UniProtKB/Swiss-Prot Accession No. P48061.1, Jun. 18, 2014.
UniProtKB/Swiss-Prot Accession No. P80162.4, Jun. 11, 2014.
UniProtKB/Swiss-Prot Accession No. P98066.2, Feb. 19, 2014.
UniProtKB/Swiss-Prot Accession No. Q8TDQ0.3, Mar. 19, 2014.
UniProtKB/Swiss-Prot Accession No. Q96HF1.2, May 14, 2014.
UniProtKB/Swiss-Prot Accession No. Q9BQ51.2, Mar. 19, 2014.
UniProtKB/Swiss-Prot Accession No. Q9HCB6.2, Jun. 11, 2014.
UniProtKB/Swiss-Prot Accession No. Q9NZQ7.1, Apr. 16, 2014.
Van der Bruggen et al. "T Cell-Defined Tumor Antigens." *Cancer Immunity.* (2013). Http:www.cancerimmunity.org/peptide.
Venturoni et al. "Investigations into the Polymorphism of Rat Tail Tendon Fibrils Using Atomic Force Microscopy." *Biochem. Biophys. Res. Commun.* 303.2(2003):508-513.
Vincent et al. "Stem Cell Differentiation: Post-Degradation Forces Kick in." *Nat. Mater.* 12.5(2013):384-386.
Vogel et al. "Local Force and Geometry Sensing Regulate Cell Functions." *Nat. Rev. Mol. Cell Biol.* 7.4(2006):265-275.
Wang et al. "Mechanotransduction at a Distance: Mechanically Coupling the Extracellular Matric with the Nucleus." *Nat. Rev. Mol. Cell. Biol.* 10.1(2009):75-82.
Wang-Gillam et al. "A Phase I Study of IMP321 and Gemcitabine as the Front-Line Therapy in Patients with Advanced Pancreatic Adenocarcinoma." *Invest. New Drugs.* 31.3(2013):707-713.
Warner et al. "Cyclooxygenases: New Forms, New Inhibitors, and Lessons from the Clinic." *FASEB J.* 18.7(2004):790-804.
Weisenberger et al. "Comprehensive DNA Methylation Analysis on the Illumina® Infinium® Assay Platform." Illumina, Inc. Mar. 25, 2008. Web.
Weiss et al. "The Demonstration of Rupture of Cell Surfaces by an Immunological Technique." *Exp. Cell Res.* 30(1963):331-338.
Wen et al. "Mechanically Robust Gelatin-Alginate IPN Hydrogels by a Combination of Enzymatic and Ionic Crosslinking Approaches." *Macromol. Mater. Eng.* 299(2013):504-513.
Wieland et al. "Engineering Molecular Circuits Using Synthetic Biology in Mammalian Cells." *Annu. Rev. Chem. Biomol. Eng.* 3(2012):209-234.
Wipff et al. "Myofibroblast Contraction Activates Latent TGF-β1 from the Extracellular Matrix." *J. Cell Biol.* 179.6(2007):1311-1323.
Wong et al. "Focal Adhesion Kinase Links Mechanical Force to Skin Fibrosis via Inflammatory Signaling." *Nat. Med.* 18.1(2011):148-152.
Wong et al. "Mechanical Force Prolongs Acute Inflammation via T-Cell-Dependent Pathways During Scar Formation." *FASEB. J.* 25.12(2011):4498-4510.
Wong et al. "Pushing Back: Wound Mechanotransduction in Repair and Regeneration." *J. Invest. Dermatol.* 131.11(2011):2186-2196.
Wozniak et al. "Mechanotransduction in Development: A Growing Role for Contractility." *Nat. Rev. Mol. Cell Biol.* 10.1(2009):34-43.
Yeung et al. "Effects of Substrate Stiffness on Cell Morphology, Cytoskeletal Structure, and Adhesion." *Cell Motil. Cytoskeleton.* 60.1(2005):24-34.
Yoo et al. "Bio-Inspired, Bioengineered and Biomimetic Drug Delivery Carriers." *Nat. Rev. Drug Discov.* 10.7(2011):521-535.
Yoon. "Hidden Markov Models and their Applications in Biological Sequene Analysis." *Curr. Genomics.* 10.6(2009):402-415.
Young et al. "Gelatin as a Delivery Vehicle for the Controlled Release of Bioactive Molecules." *J. Control. Release.* 109.1-3(2005):256-274.
Zemel et al. "Optimal Matrix Rigidity for Stress Fibre Polarization in Stem Cells." *Nat. Phys.* 6.6(2010):468-473.
Zhang et al. "A Tension-Induced Mechanostransduction Pathway Promotes Epithelial Morphogenesis." *Nature,* 471.7336(2011):99-103.
Zhang et al. "Talin Depletion Reveals Independence of Initial Cell Spreading from Integrin Activation and Traction." *Nat. Cell Biol.* 10.9(2008):1062-1068.
Zhao et al. "Stress-Relaxation Behavior in Gels with Ionic and Covalent Crosslinks." *J. Appl. Phys.* 107.6(2010):63509.
Brunner et al. Enhanced dendritic cell maturation by TNF-alpha or cytidine-phosphateguanosine DNA drives T cell activation in vitro and therapeutic anti-tumor immune responses in vivo. J Immunol. Dec. 1, 2000;165(11):6278-86.

(56) References Cited

OTHER PUBLICATIONS

Fransen et al. Local immunomodulation for cancer therapy: Providing treatment where needed. Oncoimmunology. Nov. 1, 2013;2(11):e26493.

Kathuria et al. Synthesis and characterization of elastic and macroporous chitosan-gelatin cryogels for tissue engineerin. Act Abiomaterialia 5 (2009) 406-418.

Liu et al. Immunostimulatory CpG oligodeoxynucleotides enhance the immune response to vaccine strategies involving granulocyte-macrophage colony-stimulating factor. Blood. Nov. 15, 1998;92(10):3730-6.

Yamazaki et al. CD8+ CD205+ splenic dendritic cells are specialized to induce Foxp3+ regulatory T cells. J Immunol. Nov. 15, 2008;181(10):6923-33.

Dong et al., Antitumor effect of secreted Flt3-ligand can act at distant tumor sites in a murine model of head and neck cancer. Cancer Gene Ther. Feb. 2003;10(2):96-104.

Kared et al., Treatment with granulocyte colony-stimulating factor prevents diabetes in NOD mice by recruiting plasmacytoid dendritic cells and functional CD4(+)CD25(+) regulatory T-cells. Diabetes. Jan. 2005;54(1):78-84.

McColl. Chemokines and dendritic cells: a crucial alliance. Immunol Cell Biol. Oct. 2002;80(5):489-96.

Wu et al., Intraperitoneal administration of poly(I:C) with polyethylenimine leads to significant antitumor immunity against murine ovarian tumors. Cancer Immunol Immunother. Aug. 2011;60(8):1085-96.

Salem et al., Defining the antigen-specific T-cell response to vaccination and poly(I:C)/TLR3 signaling: evidence of anhanced primary and memory CD8 T-cell responses and antitumor immunity. J Immunother. May-Jun. 2005;28 (3):220-8.

\* cited by examiner

|  | NO STIM | TNF-ALPHA/LPS | CpG-ODN | COND OLIGO |
|---|---|---|---|---|
| CCR7 | 23.5±4.3 | 27.4±2.0 | 25.6±4.2 | 34.8±7.1 |
| MHCII | 22.6±3.6 | 31.1±8.3 | 39.9±0.55 | 48.8±1.7 |
| CD86 | 20.0±4.3 | 67.5±10 | 38.1±2.3 | 57.3±2.8 |

| CONDITIONS | CpG-ODN (ug) | GM-CSF (ng) | TOTAL CELL ($10^{-6}$ CELLS) | CD11c(+)DCs ($10^{-6}$ CELLS) | CD11c(+)MHCII(+) (%) | CD11c(+)CCR7(+) (%) |
|---|---|---|---|---|---|---|
| 1 | - | 400 | 2.37±0.53 | 0.51±0.06 | 18±4.3 | 22±4.5 |
| 2 | 10 | - | 1.32±0.24 | 0.46±0.09 | 35±10 | 28±7.6 |
| 3 | 10 | 3 | 3.25±0.65 | 1.48±0.17 | 46±6.7 | 53±3.2 |
| 4 | 10 | 7 | 5.43±1.76 | 1.39±0.23 | 26±3.5 | 47±2.4 |
| 5 | 10 | 400 | 1.12±0.68 | 0.51±0.47 | 44±12 | 50±6.5 |
| 6 | 25 | 400 | 2.3±0.89 | 0.75±0.07 | 33±6.4 | 43±7.6 |
| 7 | 50 | 400 | 3.35±0.86 | 0.81±0.17 | 3.0±0.6 | 4.1±2.3 |
| 8 | 100 | 400 | 4.23±1.88 | 0.45±0.09 | 6.7±0.2 | 10±5.6 |
| 9 | 50 | 1000 | 5.12±2.34 | 3.32±0.74 | 10±1.2 | 65±1.4 |
| 10 | 50 | 3000 | 5.59±3.65 | 2.51±0.63 | 12±3.4 | 45±2.4 |
| 11 | 50 | 7000 | 6.51±2.58 | 3.91±0.78 | 11±2.4 | 60±7.8 |

Fig. 7A

CONTINUOUS CELL PROGRAMMING DEVICES

RELATED APPLICATIONS

This application is a national stage application, filed under 35 U.S.C. § 371, of International Application No. PCT/US2009/000914, filed Feb. 13, 2009, which claims the benefit of provisional applications U.S. Ser. No. 61/065,672 filed Feb. 13, 2008 and U.S. Ser. No. 61/143,630 filed Jan. 9, 2009, the contents of which are incorporated by reference in their entireties.

GOVERNMENT SUPPORT

This invention was made with Government support under R37DE013033 awarded by the National Institutes of Health. The Government has certain rights in the invention.

BACKGROUND OF THE INVENTION

Dendritic cells are the most potent activators of the immune system among antigen presenting cells. Research focused on using dendritic cells for a therapeutic benefit has been slow because dendritic cells are rare and difficult to isolate.

SUMMARY OF THE INVENTION

The invention features a device and method for continuous programming of cells, e.g., immune cells such as dendritic cells, in situ. For example, the device is implanted and is in-dwelling while constantly recruiting, educating, and dispersing or sending cells forth to lymph nodes or sites of disease or infection in the body. Improvements over existing devices include long term, ongoing activation of cells that enter the device and concomitant long term, ongoing egress of immunologically activated, e.g., antigen primed cells. The device includes a scaffold composition, a recruitment composition, and a deployment composition. The deployment composition that mediates prolonged and continuous egress of primed cells is an infection-mimicking composition such as a bacterially-derived immunomodulator. In preferred embodiments, the bacterially-derived immunomodulator is a nucleic acid such as a cytosine-guanosine oligonucleotide (CpG-ODN).

The methods are used to treat a wide variety of diseases and to develop vaccines against a wide variety of antigens. In a preferred embodiment, the present invention is used to develop a cancer vaccine. Another preferred embodiment of the present invention comprises an infection-mimicking microenvironment with means to activate the host immune system and subsequently induce an immune response. The use of a synthetic cytosine-guanosine oligonucleotide (CpG-ODN) sequence with exogenous granulocyte macrophage colony stimulating factor (GM-CSF) provides a method for precisely controlling dendritic cell migration and modulating antigen-specific immune responses. In fact, the new approach of using of this synthetic cytosine-guanosine oligonucleotide (CpG-ODN) sequence demonstrates significant improvements and provides a new avenue for development of immune therapy.

Various components of the device are tabulated and described below.

TABLE 1

| EXEMPLARY DEVICE | FUNCTION | | |
| --- | --- | --- | --- |
| | Attract a DC to Device | Present an Immunogenic Factor | Induce DC Migration from Device |
| 1 | Scaffold Composition | Scaffold Composition | Scaffold Composition |
| 2 | Bioactive Composition | Bioactive Composition | Bioactive Composition |
| 3 | Scaffold Composition | Bioactive Composition | Bioactive Composition |
| 4 | Scaffold Composition | Scaffold Composition | Bioactive Composition |
| 5 | Bioactive Composition | Scaffold Composition | Scaffold Composition |
| 6 | Bioactive Composition | Bioactive Composition | Scaffold Composition |
| 7 | Bioactive Composition | Scaffold Composition | Bioactive Composition |
| 8 | Scaffold Composition | Bioactive Composition | Scaffold Composition |

Devices perform three primary functions, e.g. attracting cells to the device, presenting an immunogenic factor, and inducing cell migration away from the device. Each of these primary functions are performed by the scaffold (bold font) and/or biological (standard font) composition(s). Table 1 provides exemplary combinations of either the scaffold or biological composition paired with at least one primary function in exemplary devices (1-8). For example, the scaffold composition performs all three primary functions (device 1). In an alternative example, the scaffold composition performs one primary function, e.g. attracts cells to the device (preferably, dendritic cells), whereas the biological composition performs two primary functions, e.g. presents an immunogenic factor and induces cells (preferably, dendritic cells) to migrate away from the device (device 3). Device 5, for instance, is the inverse combination of device 3. Exemplary secondary functions of the scaffold and/or biological compositions include, but are not limited to, targeting the device to a particular cell or tissue type, adhering/releasing the device to/from the surface of one or more cells or tissues, and modulating the stability/degradation of the device.

The invention comprises a device comprising a scaffold composition and bioactive composition, said bioactive composition being incorporated into or conjugated onto said scaffold composition, wherein said scaffold composition attracts a dendritic cell, introduces a immunogenic factor into said dendritic cell thereby activating said dendritic cell, and induces said dendritic cell to migrate away from said scaffold composition. Alternatively the bioactive composition incorporated into or coated onto the scaffold composition attracts a dendritic cell, introduces a immunogenic factor into said dendritic cell thereby activating said dendritic cell, and induces said dendritic cell to migrate away from said scaffold composition. In other preferred embodiments, the scaffold composition or bioactive composition separately attract a dendritic cell to the device, introduce an immunogenic factor into the dendritic cell, and induce the dendritic cell to migrate away from the device.

In preferred embodiments, the recruitment composition is GM-CSF, e.g., encapsulated GM-CSF. The device temporally controls local GM-CSF concentration, thereby controlling recruitment, residence, and subsequent dispersement/deployment of immune cells to lymph nodes or tissue sites distant from location of the device, e.g., sites of infection or tumor location. The concentration of GM-CSF determines whether if functions as a recruitment element or a deployment element. Accordingly, a method of programming dendritic cells in situ is carried out by introducing to a subject a device comprising scaffold composition and encapsulated recruitment composition. A pulse of recruitment composition is released from said device within 1-7 days of introduction of the device, leaving a residual amount of the recruitment composition in or on the device. The pulse is followed by slow release of the residual amount over several weeks. The local concentration of the recruitment composition and the temporal pattern of release mediates recruitment, retention, and subsequent release of dendritic cells from the device. For example, the pulse comprises at least 50, 60, 75, 90 or 95% of the amount of the recruitment composition associated with the device. An exemplary temporal release profile comprises a pulse characterized by release of at least 60% of the amount of the recruitment composition associated with said device in 1-5 days following the introduction of the device to a subject. Following the pulse, the residual amount is slowly released over an extended period of time (e.g., 1, 2, 3, 4, 5, 6, 7, 8, 9, 10, 12 days or 2, 3, 4, 5 or more weeks) following the pulse period.

The method of making a scaffold is carried out by providing a scaffold composition, incorporating into or coating onto said scaffold composition a first bioactive composition comprising polypeptides with means for attracting or repelling a dendritic cell, and contacting said scaffold composition with a second bioactive composition, wherein said second bioactive composition is covalently or non-covalently associated with said scaffold composition wherein said second bioactive composition comprises a immunogenic factor. In an alternate embodiment of this method, the linking and contacting steps are repeated to yield a plurality of layers, wherein said second bioactive composition comprises a combination of compounds with means to activate a dendritic cell.

Methods comprise continuous in situ dendritic cell programming, comprising administering to a subject, a device comprising a scaffold composition and bioactive composition, said bioactive composition being incorporated into or conjugated onto said scaffold composition, wherein said scaffold composition attracts a dendritic cell, introduces a immunogenic factor into said dendritic cell thereby activating said dendritic cell, and induces said dendritic cell to migrate away from said scaffold composition. The devices recruit and stimulate a heterogeneous population of dendritic cells. Each subset is specialized and contributes significantly to the generation of an immune response. For example, the device mediates CpG-ODN presentation and enrichment of a subset of dendritic cells, plasmacytoid DC (pDC), which are particularly important in development of anti-tumor immunity.

Methods comprise increasing vaccine efficacy, comprising administering to a subject, a device comprising a scaffold composition and bioactive composition, said bioactive composition being incorporated into or conjugated onto said scaffold composition, wherein said scaffold composition attracts a dendritic cell, introduces a immunogenic factor into said dendritic cell thereby activating said dendritic cell, and induces said dendritic cell to migrate away from said scaffold composition, thereby increasing the effectiveness of a vaccination procedure.

Methods comprise vaccinating a subject against cancer, comprising administering to a subject, a device comprising a scaffold composition and bioactive composition, said bioactive composition being incorporated into or conjugated onto said scaffold composition, wherein said scaffold composition attracts a dendritic cell, introduces a immunogenic factor into said dendritic cell thereby activating said dendritic cell, and induces said dendritic cell to migrate away from said scaffold composition, thereby conferring upon a subject anti-tumor immunity. In the case of a localized or solid tumor, the device is administered or implanted at or near the tumor site or site from which the tumor was excised or surgically removed. For example, the device is implanted at a distance of 1, 3, 5, 10, 15, 20, 25, 40 mm from a tumor site or site of excision, e.g., the PLG vaccine device is administered 16-21 mm away from a tumor mass.

Immunogenic factors include toll-like receptor (TLR) ligands. In a preferred embodiment, the immunogenic factor used is a modified TLR-9 ligand sequence, PEI-CpG-ODN.

Scaffold compositions comprise a non-biodegradable material. Exemplary non-biodegradable materials include, but are not limited to, metal, plastic polymer, or silk polymer. Moreover, scaffold compositions are composed of a biocompatible material. This biocompatible material is non-toxic or non-immunogenic.

Bioactive compositions are covalently or non-covalently linked to the scaffold composition. Bioactive compositions comprise an element, either covalently or non-covalently bonded to the surface of the scaffold composition, with means to attract a dendritic cell. Alternatively, or in addition, bioactive compositions comprise an element, either covalently or non-covalently bonded to the surface of the scaffold composition, with means to introduce an immunogenic factor into a dendritic cell. Alternatively, or further in addition, bioactive compositions comprises an element, either covalently or non-covalently bonded to the surface of the scaffold composition, with means to induce a dendritic cell to migrate away from the scaffold composition.

The element of the bioactive composition with means to manipulate a dendritic cell is a secreted or membrane-bound amino acid, peptide, polypeptide, protein, nucleotide, dinucleotide, oligonucleotide, polynucleotide, polymer, small molecule or compound. In a preferred embodiment, this element is granulocyte macrophage colony stimulating factor (GM-CSF), because this element attracts dendritic cells to the scaffold composition. In another preferred embodiment, this element is a PEI-CpG-ODN sequence because this element has means to introduce CpG-ODN sequences into a dendritic cell thereby activating the cell. In a third preferred embodiment, this element is a polynucleotide or polypeptide encoding for CCR7, a chemokine receptor that mediates dendritic cell migration towards lymph nodes and away from the scaffold composition. The CCR7 element is introduced into a dendritic cell simultaneously or sequentially with PEI-CpG-ODN sequences to enhance dendritic cell migration away from the scaffold composition.

Scaffold compositions of the present invention contain an external surface. Scaffold compositions of the present invention alternatively, or in addition, contain an internal surface. External or internal surfaces of the scaffold compositions are solid or porous. Pore size is less than about 10 nm, in the range of about 100 nm-20 µm in diameter, or greater than about 20 µm.

Scaffold compositions of the present invention comprise one or more compartments.

Devices of the present invention are administered or implanted orally, systemically, sub- or trans-cunataneously, as an arterial stent, or surgically.

The devices and methods of the invention provide a solution to several problems associated with protocols for continuous cell programming in situ. In situ cell programming systems that stimulate immune responses of the cells and induce their outward migration to populate infected or diseased bodily tissues enhance the success of recovery, e.g., the specific elimination of diseased tissue. Such a device that controls cell function and/or behavior, e.g., locomotion, contains a scaffold composition and one or more bioactive compositions. The bioactive composition is incorporated into or coated onto the scaffold composition. The scaffold composition and/or bioactive composition temporally and spatially (directionally) controls dendritic cell attraction, programming, and migration.

The devices mediate active recruitment, modification, and release of host cells from the material in vivo, thereby improving the function of cells that have contacted the scaffold. For example, the device attracts or recruits cells already resident in the body to the scaffold material, and programs or reprograms the resident cells to a desired fate (e.g., immune activation).

This device includes a scaffold composition which incorporates or is coated with a bioactive composition; the device regulates attraction, activation, and migration of dendritic cells. Depending on the application for which the device is designed, the device regulates attraction, activation, and/or migration of dendritic cells through the physical or chemical characteristics of the scaffold itself. For example, the scaffold composition is differentially permeable, allowing cell migration only in certain physical areas of the scaffold. The permeability of the scaffold composition is regulated, for example, by selecting or engineering a material for greater or smaller pore size, density, polymer cross-linking, stiffness, toughness, ductility, or viscoelasticity. The scaffold composition contains physical channels or paths through which cells can move more easily towards a targeted area of egress of the device or of a compartment within the device. The scaffold composition is optionally organized into compartments or layers, each with a different permeability, so that the time required for a cell to move through the device is precisely and predictably controlled. Migration is also regulated by the degradation, de- or re-hydration, oxygenation, chemical or pH alteration, or ongoing self-assembly of the scaffold composition.

Attraction, activation, and/or migration are regulated by a bioactive composition. The device controls and directs the activation and migration of cells through its structure. Chemical affinities are used to channel cells towards a specific area of egress. For example, cytokines are used to attract or retard the migration of cells. By varying the density and mixture of those bioactive substances, the device controls the timing of the migration. The density and mixture of these bioactive substances is controlled by initial doping levels or concentration gradient of the substance, by embedding the bioactive substances in scaffold material with a known leaching rate, by release as the scaffold material degrades, by diffusion from an area of concentration, by interaction of precursor chemicals diffusing into an area, or by production/excretion of compositions by resident support cells. The physical or chemical structure of the scaffold also regulates the diffusion of bioactive agents through the device.

The bioactive composition includes one or more compounds that regulate cell function and/or behavior. The bioactive composition is covalently linked to the scaffold composition or non-covalently associated with the scaffold.

Signal transduction events that participate in the process of cell migration are initiated in response to immune mediators. Thus, the device optionally contains a second bioactive composition that comprises GM-CSF, a CpG-ODN sequence, a cancer antigen, and/or an immunomodulator.

In some cases, the second bioactive composition is covalently linked to the scaffold composition, keeping the composition relatively immobilized in or on the scaffold composition. In other cases, the second bioactive composition is noncovalently associated with the scaffold. Noncovalent bonds are generally one to three orders of magnitude weaker than covalent bonds permitting diffusion of the factor out of the scaffold and into surrounding tissues. Noncovalent bonds include electrostatic, hydrogen, van der Waals, π aromatic, and hydrophobic.

The scaffold composition is biocompatible. The composition is bio-degradable/erodible or resistant to breakdown in the body. Relatively permanent (degradation resistant) scaffold compositions include metals and some polymers such as silk. Preferably, the scaffold composition degrades at a predetermined rate based on a physical parameter selected from the group consisting of temperature, pH, hydration status, and porosity, the cross-link density, type, and chemistry or the susceptibility of main chain linkages to degradation or it degrades at a predetermined rate based on a ratio of chemical polymers. For example, a high molecular weight polymer comprised of solely lactide degrades over a period of years, e.g., 1-2 years, while a low molecular weight polymer comprised of a 50:50 mixture of lactide and glycolide degrades in a matter of weeks, e.g., 1, 2, 3, 4, 6, 10 weeks. A calcium cross-linked gels composed of high molecular weight, high guluronic acid alginate degrade over several months (1, 2, 4, 6, 8, 10, 12 months) to years (1, 2, 5 years) in vivo, while a gel comprised of low molecular weight alginate, and/or alginate that has been partially oxidized, will degrade in a matter of weeks.

Exemplary scaffold compositions include polylactic acid, polyglycolic acid, PLGA polymers, alginates and alginate derivatives, gelatin, collagen, fibrin, hyaluronic acid, laminin rich gels, agarose, natural and synthetic polysaccharides, polyamino acids, polypeptides, polyesters, polyanhydrides, polyphosphazines, poly(vinyl alcohols), poly(alkylene oxides), poly(allylamines)(PAM), poly(acrylates), modified styrene polymers, pluronic polyols, polyoxamers, poly (uronic acids), poly(vinylpyrrolidone) and copolymers or graft copolymers of any of the above. One preferred scaffold composition includes an RGD-modified alginate.

Another preferred scaffold composition a macroporous poly-lactide-co-glycolide (PLG). For example, the PLG matrix includes GM-CSF, danger signals, and a target antigen, e.g., a cancer antigen and serves as a residence for recruited DCs as they are programmed. The recruitment element, GM-CSF, is encapsulated into the PLG scaffolds. PLG matrices that comprise the encapsulated GM-CSF provide a pulse of the dendritic cell recruitment composition and then a gradual slower rate of release. The pulse comprises at least 40, 50, 60, 75, 80% or more of the initial amount of bioactive composition with the remaining percent being released gradually over then next days or weeks after administration to the site in or on the subject to be treated. For example, release is approximately 60% of bioactive GM-CSF load within the first 5 days, followed by slow and sustained release of bioactive. GM-CSF over the next 10 days. This release profile mediates a rate of diffusion of the factor through the surrounding tissue to effectively recruit resident DCs.

Porosity of the scaffold composition influences migration of the cells through the device. Pores are nanoporous, microporous, or macroporous. For example, the diameter of nanopores are less than about 10 nm; micropore are in the range of about 100 nm-20 µm in diameter; and, macropores are greater than about 20 µm (preferably greater than about 100 µm and even more preferably greater than about 400 µm). In one example, the scaffold is macroporous with aligned pores of about 400-500 µm in diameter.

The device is manufactured in one stage in which one layer or compartment is made and infused or coated with one or more bioactive compositions. Exemplary bioactive compositions comprise polypeptides or polynucleotides. Alternatively, the device is manufactured in two or more (3, 4, 5, 6, ... 10 or more) stages in which one layer or compartment is made and infused or coated with one or more bioactive compositions followed by the construction of a second, third, fourth or more layers, which are in turn infused or coated with one or more bioactive compositions in sequence. Each layer or compartment is identical to the others or distinguished from one another by the number or mixture of bioactive compositions as well as distinct chemical, physical and biological properties.

A method of making a scaffold is carried out by providing a scaffold composition and covalently linking or noncovalently associating the scaffold composition with a first bioactive composition. The first bioactive composition preferably contains granulocyte macrophage colony stimulating factor. The scaffold composition is also contacted with a second bioactive composition, preferably one or more cytosine-guanosine oligonucleotide (CpG-ODN) sequences. The second bioactive composition is associated with the scaffold composition to yield a doped scaffold, i.e., a scaffold composition that includes one or more bioactive substances. The contacting steps are optionally repeated to yield a plurality of doped scaffolds, e.g., each of the contacting steps is characterized by a different amount of the second bioactive composition to yield a gradient of the second bioactive composition in the scaffold device. Rather than altering the amount of composition, subsequent contacting steps involve a different bioactive composition, i.e., a third, fourth, fifth, sixth . . . , composition or mixture of compositions, that is distinguished from the prior compositions or mixtures of prior doping steps by the structure or chemical formula of the factor(s). The method optionally involves adhering individual niches, layers, or components, to one another and/or insertion of semi-permeable, permeable, or nonpermeable membranes within or at one or more boundaries of the device to further control/regulate locomotion of cells or bioactive compositions.

Therapeutic applications of the device include the instruction of immune cells. For example, the method includes the steps of providing a device that includes scaffold composition with a bioactive composition incorporated therein or thereon and a mammalian cell bound to the scaffold and contacting a mammalian tissue with the device, e.g., by implanting or affixing the device into or onto a mammalian tissue. At the time of administering or implanting the device, exemplary relative amounts of each component, recruiting composition (e.g., GM-CSF), danger signal (e.g., CpG-ODN), and antigen (e.g., purified tumor antigen or tumor cell lysate) are as follows: GM-CSF: 0.5 µg-500 µg; CpG-ODN: 50 µg-3,000 µg; and Tumor antigen/lysate: 100 µg-10,000 µg.

A method of modulating an activity of a cell, e.g., a host cell, is carried out by administering to a mammal a device containing a scaffold composition and a recruitment composition incorporated therein or thereon, and then contacting the cell with a deployment signal. The deployment signal induces egress of the cells from the device. The activity of the cell at egress differs from that prior to entering the device. Cells are recruited into the device and remain resident in the device for a period of time, e.g., minutes; 0.2. 0.5, 1, 2, 4, 6, 12, 24 hours; 2, 4, 6, days; weeks (1-4), months (2, 4, 6, 8, 10, 12) or years, during which the cells are exposed to structural elements and bioactive compositions that lead to a change in the activity or level of activity of the cells. The cells are contacted with or exposed to a deployment signal that induces egress of the altered (re-educated or reprogrammed) cells and the cells migrate out of the device and into surrounding tissues or remote target locations.

The deployment signal is a composition such as protein, peptide, or nucleic acid. For example, cells migrating into the device only encounter the deployment signal once they have entered the device. In some cases, the deployment signal is a nucleic acid molecule, e.g., a plasmid containing sequence encoding a protein that induces migration of the cell out of the device and into surrounding tissues. The deployment signal occurs when the cell encounters the plasmid in the device, the DNA becomes internalized in the cell (i.e., the cell is transfected), and the cell manufactures the gene product encoded by the DNA. In some cases, the molecule that signals deployment is an element of the device and is released from the device in delayed manner (e.g., temporally or spatially) relative to exposure of the cell to the recruitment composition. Alternatively, the deployment signal is a reduction in or absence of the recruitment composition. For example, a recruitment composition induces migration of cells into the device, and a reduction in the concentration or depletion, dissipation, or diffusion of the recruitment composition from the device results in egress of cells out of the device. In this manner, immune cells such as T cells, B cells, or dendritic cells (DCs) of an individual are recruited into the device, primed and activated to mount an immune response against an antigen-specific target. Optionally, an antigen corresponding to a target to which an immune response is desired is incorporated into or onto the scaffold structure. Cytokines, such as granulocyte macrophage colony stimulating factor (GM-CSF) are also a component of the device to amplify immune activation and/or induce migration of the primed cells to lymph nodes. Other cell specific recruitment compositions are described below.

The device recruit cells in vivo, modifies these cells, and then promotes their migration to another site in the body. This approach is exemplified herein in the context of dendritic cells and cancer vaccine development but is also useful to other vaccines such as those against microbial pathogens as well as cell therapies in general. Cells educated using the devices described herein promote regeneration of a tissue or organ immediately adjacent to the material, or at some distant site. Alternatively, the cells are educated to promote destruction of a tissue (locally or at a distant site). The methods are also useful for disease prevention, e.g., to promote cell-based maintenance of tissue structure and function to stop or retard disease progression or age-related tissue changes. The education of cells within the device, "programming" and "reprogramming" permits modification of the function or activity of any cell in the body to become a multipotent stem cell again and exert therapeutic effects.

The inability of traditional and ex vivo DC-based vaccination strategies to coordinate and sustain an immune response mediated by the heterogeneous DC network in cancer patients has led to limited clinical effectiveness of these approaches. The devices and methods described herein have distinct advantages, because preferential recruitment and expansion of pDCs dramatically improves immune responses to cancer antigens and reduces tumor progression compared to previous vaccine approaches.

Other features and advantages of the invention will be apparent from the following description of the preferred embodiments thereof, and from the claims. All references cited herein are incorporated by reference.

BRIEF DESCRIPTION OF THE DRAWINGS

FIG. 1 is a diagram showing the mechanisms by which bacterial invasion and bacterial toxins damage resident skin cells promoting the production of inflammatory cytokines, including GM-CSF, and activation of dermal endothelium. Cytokine stimulation induces extravasation of leukocytes and recruits skin resident DCs (langerhans cells) and monocytes/preDCs. DCs, recruited to the site of inflammation encounter and ingest bacterium and bacterial products including antigenic molecules and CpG-rich DNA, which stimulates TLR9 activation. As a result of TLR ligation and the inflammatory conditions, the DC rapidly matures to upregulate its expression of MHC-antigen complexes, costimulatory molecules, and CCR7 and begins to home to the lymph nodes where it initiates and propagates antigen specific T-cell responses.

FIG. 2A is a schematic representation of PEI condensation of CpG-rich oligonucleotide sequences. The PEI polycation with positively charged amine groups is mixed with CpG-ODNs consisting of negatively charged phosphate groups at charge ratios (NH3+:PO4−) resulting in positively charged PEI-CpG-ODN condensates. FIG. 2B is a bar graph showing the zeta potential (my) of CpG-ODN 1826 and its PEI condensates at charge ratios of 4, 7 and 15. Box plots represent the mean and standard deviation (n=4) FIG. 2C is a bar graph showing the particle size of CpG-ODN 1826 and its PEI condensates at charge ratios of 4, 7 and 15. Values represent the average particle size and the standard deviation (n=4).

FIGS. 3A-B are bright field images of cells and their corresponding fluorescent images displaying the uptake of TAMRA labeled CpG-ODN molecules (A) or PEI-CpG-ODN condensates (B). FIG. 3C is a bar graph showing quantification of uptake of naked (-○-) and PEI-CpG-ODN (-●-) condensates over a period of 110 hours. FIG. 3D is a line graph showing quantification of uptake of PEI-CpG-ODN condensates and subsequent decondensation within JAWSII DCs. The number of PEI-CpGODN condensates in the cells (-■-), and the amount of uncondensed CpG-ODN (-□-) was monitored and quantified over a period of 70 hours. Scale bar—20 μm. Values in C (n>10 cells) and D (n>7 cells) represent the mean and standard deviation.

FIG. 4A is a series of brightfield images of activated DC morphology in correlation with fluorescent images displaying the uptake of TAMRA labeled CpG-ODN molecules condensed with PEI (charge ratio—7). FIG. 4B is a series of FACS histograms of JawsII DCs positive for the activation markers CD86, MHCII and CCR7 following no stimulation (tinted line), CpG-ODN (- - -), and PEI-CpG-ODN condensates (-) FIG. 4C is a chart showing tabulated data displaying the percentage of DCs positive for the activation markers CD86, MHCII, and CCR7 following no stimulation, and stimulation with TNF-αc/LPS or CpG-ODN or PEI-CpG-ODN. FIG. 4D is a bar graph showing CpG-ODN and DC emigration toward CCL19. The effects of no stimulation (■), and PEI (■) or CpG-ODN (■) or PEI-CpG-ODN (■) stimulation on DC emigration from the top wells of transwell systems toward media supplemented with 300 ng/ml CCL19. Migration counts taken at 24 hours. Scale bar—20 μm. Values in C and D (n=4) represent the mean and standard deviation. CpG-ODN activation media (5 μg/ml). * $P<0.05$** $P<0.01$.

FIG. 5A is a series of bar graphs showing the percentage of JawsII DCs positive for MHCII and CCR7 expression after PEI-CpG-ODN (5 μg/ml) stimulation in media supplemented with 0 (□), 50 (■) and 500 ng/ml GM-CSF (■). FIG. 5B is a line graph showing CpG-ODN and DC emigration toward CCL19 in the presence of GM-CSF. The effects of no stimulation (-■-), and stimulation with PEI (- - -) or CpG-ODN (-●-) or PEI-CpG-ODN (-●-) on DC emigration from the top wells of transwell systems toward media supplemented with 300 ng/ml CCL19. Migration counts taken at 24 hours. Values represent the mean and standard deviation (n=4).

FIG. 6A is a line graph showing the fraction of PEI-CpG-ODN condensates retained in PLG matrices over time with incubation in PBS in vitro. FIGS. 6B-C are bar graphs showing emigration of JAWS II DCs from CpG-ODN loaded scaffolds. (B) The total number of DCs that migrated from scaffolds loaded with 5, 50, 500 μg of CpG-ODN toward media supplemented with 300 ng/ml CCL19. (C) The total number of DCs that migrated from scaffolds loaded with 25 μg of CpG-ODN in the presence of 500 ng/ml GM-CSF toward media supplemented with 300 ng/ml CCL19. Migration counts taken at 48 hours. Values represent mean and standard deviation (n=4 or 5).

FIGS. 7A-B. PLG-based infection mimics continuously program DCs in situ. FIG. 7a is a chart showing the tabulated data of host DC recruitment (cell #) and DC activation (% expressing MHC or CCR7) in response to various dosages of PEI-CpG-ODN and GM-CSF loaded into PLG matrices. Matrices were implanted into the backs of C57/BL6J mice for 7 days. FIG. 7B is a bar graph showing the number of CD11c(+)MHCII(+) and CD11c(+)CCR7(+) host DCs isolated from matrices loaded with PEI-ODN control, 10 μg PEI-CpG-ODN, 400 and 3000 ng GM-CSF, and 400 and 3000 ng GM-CSF in combination with 10 μg PEI-CpG-ODN at Day 7 after implantation into the backs of C57/BL6J mice. Values represent the mean and standard deviation (n=3-5). * $P<0.05$** $P<0.01$.

FIG. 8a is a bar graph showing the number of FITC(+) DCs that have homed to the inguinal lymph nodes as a function of time subsequent to their residence at FITC painted blank matrices (-□-), FITC painted GM-CSF loaded matrices (-■-), and FITC painted GM-CSF and CpG-ODN matrices (-■-). GM-CSF dose was 3000 ng and CPG-ODN dose was 10 μg. FIG. 8B is a digital photograph of inguinal lymph nodes extracted from C57BL/6J mice (control) and at 10 days after the implantation of matrices incorporating 10 μg CpG-ODN+3000 ng GM-CSF (infection-mimic). FIGS. 8C-D are bar graphs showing the total number of cells (C) and CD11c+DCs (D) isolated from inguinal lymph nodes extracted from C57BL/6J mice at 2 and 7 days after the implantation of blank matrices (□) and matrices incorporating 3000 ng GM-CSF (■) or 10 μg CpG-ODN+3000 ng GM-CSF (■). Values in A, C and D represent the mean and standard deviation (n=4 or 5). * $P<0.05$** $P<0.01$.

FIG. 10A is a series of representative photomicrographs of tumor sections from mice vaccinated with PLG cancer vaccines that appropriately control the presentation of tumor lysates, 3000 ng GM-CSF and CpG-ODN and blank (blank) scaffold controls. Sections were stained to detect for CD4(+) and CD8(+) T cell infiltrates into tumor tissue that was explanted from mice that had developed tumors at days 20-25. FIG. 10B is a bar graph showing T-cell infiltrates into B16-F10 melanoma tumors of vaccinated animals. Tumors were explanted from C57BL/6J mice treated with blank PLG scaffolds (□), or PLG scaffolds incorporating B16-F10 melanoma tumor lysates, 3000 ng GM-CSF and 10 µg PEI-CpG-ODN (■) at days 20-25. T-cell infiltrates were examined in randomized sections of tumors (n=4, 1 mm³). Scale bar—50 µm. Values in A, D and E represent the mean and standard deviation (n=3 or 4). * P<0.05** P<0.01.

FIG. 11A is a line graph showing cumulative release of GM-CSF from PLG matrices over a period of 23 days. FIG. 11B is a photograph showing H&E staining of sectioned PLG scaffolds explanted from subcutaneous pockets in the backs of C57BL/6J mice after 14 days: Blank scaffolds, and GM-CSF (3000 ng) loaded scaffolds. FIG. 11c is a series of FACS plots of cells isolated from explanted scaffolds and stained for the DC markers, CD11c and CD86. Cells were isolated from blank and GM-CSF (3000 ng) loaded scaffolds implanted for 28 days. Numbers in FACS plots indicate the percentage of the cell population positive for both markers. FIG. 11D is a bar graph showing the fractional increase in CD11c(+)CD86(+) DCs isolated from PLG scaffolds at day 14 after implantation in response to doses of 1000, 3000 and 7000 ng of GM-CSF, as normalized to the blank control (Blanks). FIG. 11E is a line graph showing the in vivo concentration profiles of GM-CSF at the implant site of PLG scaffolds incorporating 0 (-), 3000 (-○-), and 7000 ng (-●-) of GM-CSF as a function of time post implantation. FIG. 11F is a bar graph showing the percentage of CD11c(+)CCR7(+) host DCs isolated from scaffolds loaded with 0 (□), 400 (■), 3000 ng (■), and 7000 ng of GM-CSF (☒) as a function of time after implantation into the backs of C57BL/6J mice. Scale bar in B—500 µm. Values in A, D, E, and F represent mean and standard deviation (n=4 or 5). * P<0.05 ** P<0.01.

(FIG. 13A) shows a comparison of survival times in mice vaccinated with PLG matrices loaded with tumor lysates and 1, 10, 50 or 100 µg of CpG-ODN. FIG. 13B shows a comparison of survival times in mice vaccinated with PLG matrices loaded with tumor lysates, 3000 ng GM-CSF and 1, 10, 50 or 100 µg of CpG-ODN. A correlation between the number of (FIG. 13C) CD11c(+)PDCA-1(+) DCs, (FIG. 13D) CD11c(+)CD11b(+) DCs, and (FIG. 13E) CD11c(+)CD8(+) cDCs at the PLG vaccine site at day 10 and the percent of animals surviving B16-F10 melanoma tumor challenge at Day 100. FIG. 13F shows the fraction of total DC population consisting of CD11c(+)CD11b(+) cDCs, CD11c(+)PDCA-1(+) pDCs, and CD11c(+)CD8(+) cDCs generated at the PLG vaccine site at day 10. Survival percentage is taken at Day 100 after challenge with B16-F10 melanoma cells.

FIG. 14A shows a comparison of the survival time in C57BL/6 mice treated with blank PLG scaffolds, and PLG vaccines (3 µg GM-CSF+100 µg CpG-ODN+ tumor lysates). FIG. 14B shows a comparison of tumor growth in C57BL/6 mice treated with blank PLG scaffolds, and PLG vaccines (3 µg GM-CSF+100 µg CpG-ODN+ tumor lysates). Mice were inoculated with $5 \times 10^5$ B16-F10 melanoma tumor cells at Day 0 and tumors were allowed to grow for 7 days when mice were either implanted with blank PLG matrices or PLG vaccine. The average tumor size was expressed as one-half the product of the smallest and largest diameter.

DETAILED DESCRIPTION OF THE INVENTION

Figure 1:
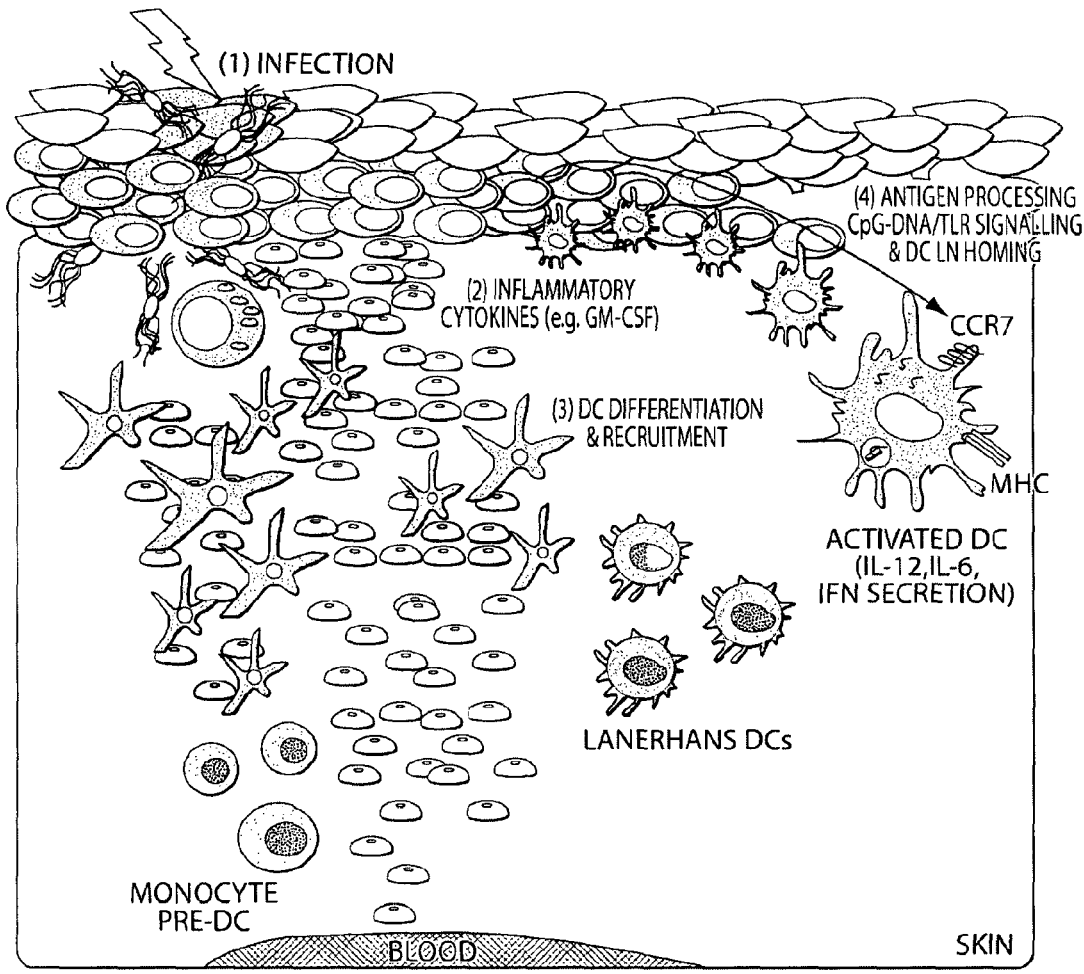
FIG. 1 is a diagram of the immune response to infection.

Cancer vaccines typically depend on cumbersome and expensive manipulation of cells in the laboratory, and subsequent cell transplantation leads to poor lymph node homing and limited efficacy. The invention solves these problems by using materials that mimic key aspects of bacterial infection to directly control immune cell trafficking and activation in the body. Polymers were designed to first release a cytokine to recruit and house host dendritic cells (DCs), and subsequently present cancer antigens and danger signals to activate the resident DCs and dramatically enhance their homing to lymph nodes. Specific and protective anti-tumor immunity was generated with these materials, as 90% survival was achieved in animals that otherwise die from cancer within 25 days. These materials are useful in cancer and other vaccines to program and control the trafficking of a variety of cell types in the body.

A polymer system was designed to not only serve as a drug delivery device, but also as a physical, antigen-presenting structure to which the DCs are recruited, and where DCs reside while they are activated using a material (poly [lactide-co-glycolide]) and bioactive molecules (GM-CSF and CpG-ODN). These bioactive molecules have excellent safety profiles. The material system serves as an effective cancer vaccine, eliminating the time, expense and regulatory burden inherent to existing cell therapies and reducing or eliminating the need for multiple, systemic injections and high total drug loading. The devices described herein utilize infection-mimicking materials to program DCs in situ.

A quantitative understanding of the ability of GM-CSF to impact DC recruitment, activation and emigration in vitro was developed in order to appropriately design a material system for vaccination. GM-CSF enhanced DC recruitment and proliferation in a dose dependent manner. However, high concentrations (>100 ng/ml) of GM-CSF inhibited DC migration toward a lymph node derived chemoattractant (CCL19). Immunohistochemical staining revealed that the high concentrations of GM-CSF (500 ng/ml) also down-regulated DC expression of the CCL19 receptor CCR7 and MHCII. These results indicated that control over GM-CSF exposure was needed to both recruit and program DCs in vivo. If GM-CSF alone is to be used for both purposes, its local concentration is designed to decrease over time in order to release DCs that become trapped in the material. Alternatively, provision of a danger signal (e.g., CpG-ODN) in the local environment is used to release DCs from GM-CSF inhibition once they reside at the infection-mimicking site.

Based on this understanding, a macroporous poly-lactide-co-glycolide (PLG) matrix was designed to present GM-CSF, danger signals, and cancer antigens in a defined spatiotemporal manner in vivo, and serve as a residence for recruited DCs as they are programmed. GM-CSF was encapsulated (54% efficiency) into PLG scaffolds using a high pressure $CO_2$ foaming process. These matrices released approximately 60% of their bioactive GM-CSF load within the first 5 days, followed by slow and sustained release of bioactive GM-CSF over the next 10 days. This release profile allows diffusion of the factor through the surrounding tissue to effectively recruit resident DCs.

Inflammatory Mediators

Dendritic Cell (DC) proliferation, migration and maturation are sensitive to inflammatory mediators, and granulocyte macrophage colony stimulating factor (GM-CSF) has been identified as a potent stimulator of immune responses, specifically against cancer antigens. GM-CSF also has the ability to recruit and program these antigen-presenting immune cells. Additionally, Cytosine-guanosine (CpG) oligonucleotide (CpG-ODN) sequences found in bacterial DNA are potent immunomodulators that stimulate DC activation, leading to specific T-cell responses. Creating an infection mimicking microenvironment by the presentation of exogenous GM-CSF and CpG-ODN provides an avenue to precisely control the number and timing of DC migration and modulate antigen specific immune responses.

The vertebrate immune system employs various mechanisms for pathogen recognition making it adept at generating antigen-specific responses and clearing infection. Immunity is controlled by antigen presenting cells (APCs), especially dendritic cells (DCs), which capture antigens and are activated by stimuli, unique 'danger signals' of the invading pathogen, such as CpG dinucleotide sequences in bacterial DNA (Bancbereau J, and Steinman R M. Nature. 392, 245-252. (1998); Klinman D M. Nat. Rev. Immunol. 4, 249-58 (2004); each herein incorporated by reference).

However, cancerous cells, derived from self-tissues, are void of the danger signals required to signal DC maturation and instead promote an immunosuppressive microenvironment that allows cells to escape immunity. Key elements of infection are inflammatory cytokines and danger signals (FIG. 1). A polymeric material system is ideal to present these factors in the required spatiotemporal manner to provide an infection-mimicking microenvironment in situ that useful as a vaccine. These infection mimics provide the continuous programming of host DCs, providing for efficient DC activation and dispersement in situ. These infection-mimicking devices are used for numerous vaccine applications including melanoma cancer vaccines.

In many infections, inflammatory cytokines and danger signals stimulate specific DC responses that mediate immune recognition and pathogen clearance (FIG. 1). For example, upon bacterial invasion and release of toxins, skin cells such as fibroblasts, keratinocytes and melanocytes are damaged resulting in the release of inflammatory cytokines, such as GM-CSF (Hamilton J. Trends in Immunol. 23, 403-408. (2002); Hamilton J., and Anderson G. Growth Factors. 22(4), 225-231. (2004); each herein incorporated by reference), that act to recruit Langerhans DC (skin) and DC precursors (monocytes; blood) (Hamilton J. Trends in Immunol. 23, 403-408. (2002); Hamilton J., and Anderson G. Growth Factors. 22(4), 225-231. (2004); Bowne W. B., et al. Cytokines Cell Mol Ther. 5(4), 217-25. (1999); Dranoff, G. Nat. Rev. Cancer 4, 11-22 (2004); each herein incorporated by reference). As DCs arrive to the site of infection they begin to differentiate, and increase in phagocytic ability in response to the inflammation (Mellman I., and Steinman R. M. Cell. 106, 255-258. (2001), herein incorporated by reference), and DCs that ingest bacteria or their products begin to process antigens and DC maturation proceeds via endosomal TLR9 signaling stimulated by CpG dinucleotide sequences in bacterial DNA (Krieg A. M., Hartmann G., and Weiner G. J. CpG DNA: A potent signal for growth, activation, and maturation of human dendritic cells. Proc Natl Acad Sci USA. 16, 9305-9310 (1999), herein incorporated by reference). Mature DCs then home to the lymph nodes where they prime antigen specific T-cell responses that clear infection.

CpG-ODNs are potent "danger signals" that upregulate DC expression of CCR7, CD80/86 costimulatory molecules, and MHC-antigen complexes. Importantly, TLR9 signaling induces DCs into promoting Th1-like, cytotoxic-Tcell responses, by cytokine production (e.g. type 1 IFN) and cross-presentation of antigen onto MHCI molecules. The presentation of these signals concurrently with tumor antigens provides the danger signal needed to promote immune responses that effectively fight cancerous cells.

Different classes of CPG-ODNs promote different immune responses depending on the ODN's specific structure and sequence. The ODN utilized in the present invention, CpG-ODN 1826, has been successfully tested in various mouse vaccination models, including melanoma. CpG-ODN 1826 has shown a beneficial effect alone or when used as adjuvant for peptide vaccines and whole cell vaccines. Moreover, ODN 1826 has been shown to directly promote DC maturation and cytokine production. This particular CpG ODN sequence also indirectly activates Th1 cells and NK cells and, thus, enhances adaptive cellular immune responses.

Vector systems that promote CpG internalization into DCs to enhance delivery and its localization to TLR9 have been developed. The amine-rich polycation, polyethylenimine (PEI) has been extensively used to condense plasmid DNA, via association with DNA phosphate groups, resulting in small, positively charge condensates facilitating cell membrane association and DNA uptake into cells (Godbey W. T., Wu K. K., and Mikos, A. G. J. of Biomed Mater Res, 1999, 45, 268-275; Godbey W. T., Wu K. K., and Mikos, A. G. Proc Natl Acad Sci USA. 96(9), 5177-81. (1999); each herein incorporated by reference). Consequently, PEI has been utilized as a non-viral vector to enhance gene transfection and to fabricate PEI-DNA loaded PLG matrices that promoted long-term gene expression in host cells in situ (Huang Y C, Riddle F, Rice K G, and Mooney D J. Hum Gene Ther. 5, 609-17. (2005), herein incorporated by reference). Therefore, CpG-ODNs were condensed with PEI molecules, and the size and charge of these PEI-CpG-ODN condensates, as dependent on the amine-phosphate charge ratio, was characterized. The ability of PEI condensation to enhance DC internalization of CpG-ODN was assessed, and the subsequent decondensation of PEI-CpG-ODN within DCs and its promotion of DC activation was analyzed in vitro. To determine whether PEI-CpG-ODNs had the potential to improve upon the vaccination effects of the GM-CSF based system described in chapter 3, its stimulatory effects on DCs maturation and mobilization in the presence of GM-CSF was also examined.

To appropriately mimic infection and program cells in situ a PLG system was designed to not only serve as a drug delivery device, that releases inflammatory cytokines (eg. GM-CSF) but also as a physical structure to which the DCs are recruited and reside while they are activated by danger signals (eg. CpG-ODNs). The ability to control DC recruitment to and DC residence within porous PLG matrices is achieved using temporal control over the delivery of GM-CSF in situ, which results in batches of programmed DCs being dispersed only when GM-CSF levels were designed to subside in situ. This system dispersed 6% of programmed DCs to the lymph nodes and induced protective anti-tumor immunity in 23% of mice when applied as a cancer vaccine. The cell programming and dispersement efficiency is improved using an overriding secondary signal (CpG-ODN) that continuously releases DCs from GM-CSF inhibition and promotes DC maturation and dispersement in the presence of high GM-CSF levels in situ. Specifically, PLG matrices were fabricated to locally present synthetic CpG-ODN with exogenous GM-CSF allowing for DCs recruited by GM-CSF to be stimulated by CpG-ODN in situ.

Dendritic Cells

Dendritic cells (DCs) are immune cells within the mammalian immune system and are derived from hematopoietic bone marrow progenitor cells. More specifically, dendritic cells can be categorized into lymphoid (or plasmacytoid) dendritic cell (pDC) and myeloid dendritic cell (mDC) subdivisions having arisen from a lymphoid (or plasmacytoid) or myeloid precursor cell, respectively. From the progenitor cell, regardless of the progenitor cell type, an immature dendritic cell is born. Immature dendritic cells are characterized by high endocytic activity and low T-cell activation potential. Thus, immature dendritic cells constitutively sample their immediate surrounding environment for pathogens. Exemplary pathogens include, but are not limited to, a virus or a bacteria. Sampling is accomplished by pattern recognition receptors (PRRs) such as the toll-like receptors (TLRs). Dendritic cells activate and mature once a pathogen is recognized by a pattern recognition receptor, such as a toll-like receptor.

Mature dendritic cells not only phagocytose pathogens and break them down, but also, degrade their proteins, and present pieces of these proteins, also referred to as antigens, on their cell surfaces using MHC (Major Histocompatibility Complex) molecules (Classes I, II, and III). Mature dendritic cells also upregulate cell-surface receptors that serve as co-receptors for T-cell activation. Exemplary co-receptors include, but are not limited to, CD80, CD86, and CD40. Simultaneously, mature dendritic cells upregulate chemotactic receptors, such as CCR7, that allows the cell to migrate through the blood stream or the lymphatic system to the spleen or lymph node, respectively.

Dendritic cells are present in external tissues that are in contact with the external environment such as the skin (dendritic cells residing in skin are also referred to as Langerhans cells). Alternatively, dendritic cells are present in internal tissues that are in contact with the external environment such as linings of the nose, lungs, stomach, and intestines. Finally, immature dendritic cells reside in the blood stream. Once activated, dendritic cells from all off these tissues migrate to lymphoid tissues where they present antigens and interact with T cells and B cells to initiate an immune response. One signaling system of particular importance for the present invention involves the chemokine receptor CCR7 expressed on the surface of dendritic cells and the chemokine receptor ligand CCL19 secreted by lymph node structures to attract migrating mature dendritic cells toward high concentrations of immune cells. Exemplary immune cells activated by contact with mature dendritic cells include, but are not limited to, helper T cells, killer T cells, and B cells. Although multiple cell types within the immune system present antigens, including macrophages and B lymphocytes, dendritic cells are the most potent activators of all antigen-presenting cells.

Dendritic cells earned their name from the characteristic cell shape comprising multiple dendrites extending from the cell body. The functional benefit of this cell shape is a significantly increased cell surface and contact area to the surroundings compared to the cell volume. Immature dendritic cells sometimes lack the characteristic dendrite formations and are referred to as veiled cells. Veiled cells possess large cytoplasmic veils rather than dendrites.

Toll-Like Receptors (TLRs)

TLRs are a class of single transmembrane domain, non-catalytic, receptors that recognize structurally conserved molecules referred to as pathogen-associated molecular patterns (PAMPs). PAMPs are present on microbes and are distinguishable from host molecules. TLRs are present in all vertebrates. Thirteen TLRs (referred to as TLRs 1-13, consecutively) have been identified in humans and mice. Humans comprise TLRs 1-10.

TLRs and interleukin-1 (IL-1) receptors comprise a receptor superfamily the members of which all share a TIR domain (Toll-IL-1 receptor). TIR domains exist in three varieties with three distinct functions. TIR domains of subgroup 1 are present in receptors for interleukins produced by macrophages, monocytes, and dendritic cells. TIR domains of subgroup 2 are present in classical TLRs which bind directly or indirectly to molecules of microbial origin. TIR domains of subgroup 3 are present in cytosolic adaptor proteins that mediate signaling between proteins comprising TIR domains of subgroups 1 and 2.

TLR ligands comprise molecules that are constantly associated with and highly specific for a threat to the host's survival such as a pathogen or cellular stress. TLR ligands are highly specific for pathogens and not the host. Exemplary pathogenic molecules include, but are not limited to, lipopolysaccharides (LPS), lipoproteins, lipoarabinomannan, flagellin, double-stranded RNA, and unmethylated CpG islands of DNA.

In one preferred embodiment of the present invention, the Toll-Like receptor 9 (TLR9) is activated by specific unmethylated CpG-containing sequences in bacterial DNA or synthetic oligonucleotides (ODNs) found in the endosomal compartment of dendritic cells. Methylation status of the CpG site is a crucial distinction between bacterial and mammalian DNA, as well as between normal and cancerous tissue. Unmethylated ODNs including one or more CpG motifs mimic the effects of bacterial DNA. Alternatively, or in addition, unmethylated ODNs including one or more CpG motifs occur within oncogenes present within malignant tumor cells.

One or more sequences of the TLR-9 receptor recognizes one or more CpG-ODN sequences of the present invention. TLR-9 receptors encompassed by the present invention are described by the following sequences.

Human TLR-9, isoform A, is encoded by the following mRNA sequence (NCBI Accession No. NM_017442 and SEQ ID NO: 1; the start codon for all mRNA sequences presented herein is bolded and capitalized):

```
   1 ggaggtcttg tttccggaag atgttgcaag gctgtggtga aggcaggtgc agcctagcct
  61 cctgctcaag ctacaccctg gccctccacg catgaggccc tgcagaactc tggagatggt
 121 gcctacaagg gcagaaaagg acaagtcggc agccgctgtc ctgagggcac cagctgtggt
 181 gcaggagcca agacctgagg gtggaagtgt cctcttagaa tggggagtgc ccagcaaggt
 241 gtaccgcta ctggtgctat ccagaattcc catctctccc tgctctctgc ctgagctctg
 301 ggccttagct cctccctggg cttggtagag gacaggtgtg aggccctcat gggatgtagg
 361 ctgtctgaga ggggagtgga aagaggaagg ggtgaaggag ctgtctgcca tttgactatg
 421 caaatggcct ttgactcatg ggaccctgtc ctcctcactg ggggcagggt ggagtggagg
 481 gggagctact aggctggtat aaaaatctta cttcctctat tctctgagcc gctgctgccc
 541 ctgtgggaag ggacctcgag tgtgaagcat ccttccctgt agctgctgtc cagtctgccc
 601 gccagaccct ctggagaagc ccctgccccc cagcATGggt ttctgccgca gcgccctgca
 661 cccgctgtct ctcctggtgc aggccatcat gctggccatg acctggccc tgggtacctt
 721 gcctgccttc ctaccctgtg agctccagcc ccacgcctg gtgaactgca actggctgtt
 781 cctgaagtct gtgcccact tctccatggc agcacccgt ggcaatgtca ccagcctttc
 841 cttgtcctcc aaccgcatcc accacctcca tgattctgac tttgcccacc tgcccagcct
 901 gcggcatctc aacctcaagt ggaactgccc gccggttggc ctcagcccca tgcacttccc
 961 ctgccacatg accatcgagc cagcaccttt cttggctgtg cccaccctgg aagagctaaa
1021 cctgagctac aacaacatca tgactgtgcc tgcgctgccc aaatccctca tatccctgtc
1081 cctcagccat accaacatcc tgatgctaga ctctgccagc ctcgccgccc tgcatgccct
1141 gcgcttccta ttcatggacg gcaactgtta ttacaagaac ccctgcaggc aggcactgga
1201 ggtggcccg ggtgccctcc ttggcctggg caacctcacc cacctgtcac tcaagtacaa
1261 caacctcact gtggtgcccc gcaacctgcc ttcagcctg gagtatctgc tgttgtccta
1321 caaccgcatc gtcaaactgg cgcctgagga cctggccaat ctgaccgccc tgcgtgtgct
1381 cgatgtgggc ggaaattgcc gccgctgcga ccacgctccc aaccctgca tggagtgccc
1441 tcgtcacttc ccccagctac atcccgatac cttcagccac ctgagccgtc ttgaaggcct
1501 ggtgttgaag gacagttctc tctcctggct gaatgccagt tggttccgtg ggctgggaaa
1561 cctccgagtg ctggacctga gtgagaactt cctctacaaa tgcatcacta aaaccaaggc
1621 cttccagggc ctaacacagc tgcgcaagct taacctgtcc ttcaattacc aaaagagggt
1681 gtcctttgcc cacctgtctc tggccccttc cttcgggagc ctggtcgccc tgaaggagct
1741 ggacatgcac ggcatcttct tccgctcact cgatgagacc acgctccggc cactggccg
1801 cctgccatg ctccagactc tgcgtctgca gatgaacttc atcaaccagg cccagctcgg
1861 catcttcagg gccttccctg gcctgcgcta cgtggacctg tcggacaacc gcatcagcgg
1921 agcttcggag ctgacagcca ccatggggga ggcagatgga gggagaagg tctggctgca
1981 gcctgggac cttgctccgg ccccagtgga cactcccagc tctgaagact tcaggcccaa
2041 ctgcagcacc ctcaacttca cccttggatct gtcacggaac aacctggtga ccgtgcagcc
```

-continued

```
2101 ggagatgttt gcccagctct cgcacctgca gtgcctgcgc ctgagccaca actgcatctc
2161 gcaggcagtc aatggctccc agttcctgcc gctgaccggt ctgcaggtgc tagacctgtc
2221 ccacaataag ctggacctct accacgagca ctcattcacg gagctaccac gactggaggc
2281 cctggacctc agctacaaca gccagcccct tggcatgcag ggcgtgggcc acaacttcag
2341 cttcgtggct cacctgcgca ccctgcgcca cctcagcctg gcccacaaca acatccacag
2401 ccaagtgtcc cagcagctct gcagtacgtc gctgcgggcc ctggacttca gcggcaatgc
2461 actgggccat atgtgggccg agggagacct ctatctgcac ttcttccaag gcctgagcgg
2521 tttgatctgg ctggacttgt cccagaaccg cctgcacacc ctcctgcccc aaaccctgcg
2581 caacctcccc aagagcctac aggtgctgcg tctccgtgac aattacctgg ccttctttaa
2641 gtggtggagc ctccacttcc tgcccaaact ggaagtcctc gacctggcag gaaaccagct
2701 gaaggccctg accaatggca gcctgcctgc tggcacccgg ctccggaggc tggatgtcag
2761 ctgcaacagc atcagcttcg tggccccgg cttctttcc aaggccaagg agctgcgaga
2821 gctcaacctt agcgccaacg ccctcaagac agtggaccac tcctggtttg ggcccctggc
2881 gagtgccctg caaatactag atgtaagcgc caaccctctg cactgcgcct gtggggcggc
2941 ctttatggac ttcctgctgg aggtgcaggc tgccgtgccc ggtctgccca gccgggtgaa
3001 gtgtggcagt ccgggccagc tccagggcct cagcatcttt gcacaggacc tgcgcctctg
3061 cctggatgag gccctctcct gggactgttt cgccctctcg ctgctggctg tggctctggg
3121 cctgggtgtg cccatgctgc atcacctctg tggctgggac ctctggtact gcttccacct
3181 gtgcctggcc tggcttccct ggcggggcg gcaaagtggg cgagatgagg atgccctgcc
3241 ctacgatgcc ttcgtggtct tcgacaaaac gcagagcgca gtggcagact gggtgtacaa
3301 cgagcttcgg gggcagctgg aggagtgccg tgggcgctgg gcactccgcc tgtgcctgga
3361 ggaacgcgac tggctgcctg gcaaaaccct ctttgagaac ctgtgggcct cggtctatgg
3421 cagccgcaag acgctgtttg tgctggccca cacggaccgg gtcagtggtc tcttgcgcgc
3481 cagcttcctg ctggcccagc agcgcctgct ggaggaccgc aaggacgtcg tggtgctggt
3541 gatcctgagc cctgacggcc gccgctcccg ctatgtgcgg ctgcgccagc gcctctgccg
3601 ccagagtgtc ctcctctggc cccaccagcc cagtggtcag cgcagcttct gggcccagct
3661 gggcatggcc ctgaccaggg acaaccacca cttctataac cggaacttct gcagggacc
3721 cacggccgaa tagccgtgag ccggaatcct gcacggtgcc acctccacac tcacctcacc
3781 tctgcctgcc tggtctgacc ctcccctgct cgcctccctc accccacacc tgacacagag
3841 caggcactca ataaatgcta ccgaaggc
```

Human TLR-9, isoform A, is encoded by the following amino acid sequence (NCBI Accession No. NP_059138 and SEQ ID NO: 2):

MGFCRSALHPLSLLVQAIMLAMTLALGTLPAFLPCELQPHGLVNCNWLFLKSVPHFSMAAPRGNVTSL

SLSSNRIHHLHDSDFAHLPSLRHLNLKWNCPPVGLSPMHFPCHMTIEPSTFLAVPTLEELNLSYNNIMTV

PALPKSLISLSLSHTNILMLDSASLAGLHALRFLFMDGNCYYKNPCRQALEVAPGALLGLGNLTHLSLK

YNNLTVVPRNLPSSLEYLLLSYNRIVKLAPEDLANLTALRVLDVGGNCRRCDHAPNPCMECPRHFPQL

HPDTFSHLSRLEGLVLKDSSLSWLNASWFRGLGNLRVLDLSENFLYKCITKTKAFQGLTQLRKLNLSFN

YQKRVSFAHLSLAPSFGSLVALKELDMHGIFFRSLDETTLRPLARLPMLQTLRLQMNFINQAQLGIFRAF

PGLRYVDLSDNRISGASELTATMGEADGGEKVWLQPGDLAPAPVDTPSSEDFRPNCSTLNFTLDLSRN

-continued

```
NLVTVQPEMFAQLSHLQCLRLSHNCISQAVNGSQFLPLTGLQVLDLSHNKLDLYHEHSFTELPRLEALD

LSYNSQPFGMQGVGHNFSFVAHLRTLRHLSLAHNNIHSQVSQQLCSTSLRALDFSGNALGHMWAEGD

LYLHFFQGLSGLIWLDLSQNRLHTLLPQTLRNLPKSLQVLRLRDNYLAFFKWWSLHFLPKLEVLDLAG

NQLKALTNGSLPAGTRLRRLDVSCNSISFVAPGFFSKAICELRELNLSANALKTVDHSWFGPLASALQIL

DVSANPLHCACGAAFMDFLLEVQAAVPGLPSRVKCGSPGQLQGLSIFAQDLRLCLDEALSWDCFALSL

LAVALGLGVPMLHHLCGWDLWYCFHLCLAWLPWRGRQSGRDEDALPYDAFVVFDKTQSAVADWV

YNELRGQLEECRGRWALRLCLEERDWLPGKTLFENLWASVYGSRKTLFVLAHTDRVSGLLRASFLLA

QQRLLEDRKDVVVLVILSPDGRRSRYVRLRQRLCRQSVLLWPHQPSGQRSFWAQLGMALTRDNHHFY

NRNFCQGPTAE
```

Granulocyte Macrophage Colony Stimulating Factor (GM-CSF)

Granulocyte-macrophage colony-stimulating factor (GM-CSF) is a protein secreted by macrophages, T cells, mast cells, endothelial cells and fibroblasts. Specifically, GM-CSF is a cytokine that functions as a white blood cell growth factor. GM-CSF stimulates stem cells to produce granulocytes and monocytes. Monocytes exit the blood stream, migrate into tissue, and subsequently mature into macrophages.

Scaffold devices described herein comprise and release GM-CSF polypeptides to attract host DCs to the device. Contemplated GM-CSF polypeptides are isolated from endogenous sources or synthesized in vivo or in vitro. Endogenous GM-CSF polypeptides are isolated from healthy human tissue. Synthetic GM-CSF polypeptides are synthesized in vivo following transfection or transformation of template DNA into a host organism or cell, e.g. a mammal or cultured human cell line. Alternatively, synthetic GM-CSF polypeptides are synthesized in vitro by polymerase chain reaction (PCR) or other art-recognized methods Sambrook, J., Fritsch, E. F., and Maniatis, T., Molecular Cloning: A Laboratory Manual. Cold Spring Harbor Laboratory Press, NY, Vol. 1, 2, 3 (1989), herein incorporated by reference).

GM-CSF polypeptides are modified to increase protein stability in vivo. Alternatively, GM-CSF polypeptides are engineered to be more or less immunogenic. Endogenous mature human GM-CSF polypeptides are glycosylated, reportedly, at amino acid residues 23 (leucine), 27 (asparagine), and 39 (glutamic acid) (see U.S. Pat. No. 5,073,627). GM-CSF polypeptides of the present invention are modified at one or more of these amino acid residues with respect to glycosylation state.

GM-CSF polypeptides are recombinant. Alternatively GM-CSF polypeptides are humanized derivatives of mammalian GM-CSF polypeptides. Exemplary mammalian species from which GM-CSF polypeptides are derived include, but are not limited to, mouse, rat, hamster, guinea pig, ferret, cat, dog, monkey, or primate. In a preferred embodiment, GM-CSF is a recombinant human protein (PeproTech, Catalog #300-03). Alternatively, GM-CSF is a recombinant murine (mouse) protein (PeproTech, Catalog #315-03). Finally, GM-CSF is a humanized derivative of a recombinant mouse protein.

Human Recombinant GM-CSF (PeproTech, Catalog #300-03) is encoded by the following polypeptide sequence (SEQ ID NO: 3):

```
MAPARSPSPS TQPWEHVNAI QEARRLLNLS RDTAAEMNET VEVISEMFDL QEPTCLQTRL

ELYKQGLRGS LTKLKGPLTM MASHYKQHCP PTPETSCATQ IITFESFKEN LKDFLLVIPF

DCWEPVQE
```

Murine Recombinant GM-CSF (PeproTech, Catalog #315-03) is encoded by the following polypeptide sequence (SEQ ID NO: 7):

```
MAPTRSPITV TRPWKHVEAI KEALNLLDDM PVTLNEEVEV VSNEFSFKKL TCVQTRLKIF

EQGLRGNFTK LKGALNMTAS YYQTYCPPTP ETDCETQVTT YADFIDSLKT FLTDIPFECK KPVQK
```

Human Endogenous GM-CSF is encoded by the following mRNA sequence (NCBI Accession No. NM_000758 and SEQ ID NO: 8):

```
  1 acacagagag aaaggctaaa gttctctgga ggatgtggct gcagagcctg ctgctcttgg
 61 gcactgtggc ctgcagcatc tctgcacccg cccgctcgcc cagccccagc acgcagccct
121 gggagcatgt gaatgccatc caggaggccc ggcgtctcct gaacctgagt agagacactg
181 ctgctgagat gaatgaaaca gtagaagtca tctcagaaat gtttgacctc caggagccga
```

```
-continued
241 cctgcctaca gacccgcctg gagctgtaca agcagggcct gcggggcagc ctcaccaagc 301 tcaagggccc cttgaccatg atggccagcc actacaagca gcactgccct ccaaccccgg 361 aaacttcctg tgcaacccag attatcacct ttgaaagttt caaagagaac ctgaaggact 421 ttctgcttgt catccccttt gactgctggg agccagtcca ggagtgagac cggccagatg 481 aggctggcca agccggggag ctgctctctc atgaaacaag agctagaaac tcaggatggt 541 catcttggag ggaccaaggg gtgggccaca gccatggtgg gagtggcctg gacctgccct 601 gggccacact gaccctgata caggcatggc agaagaatgg gaatatttta tactgacaga 661 aatcagtaat atttatatat ttatattttt aaaatattta tttatttatt tatttaagtt 721 catattccat atttattcaa gatgttttac cgtaataatt attattaaaa atatgcttct 781 a
```

Human Endogenous GM-CSF is encoded by the following amino acid sequence (NCBI Accession No. NP_000749.2 and SEQ ID NO: 9):

MWLQSLLLLGTVACSISAPARSPSPSTQPWEHVNAIQEARRLLNLSRDTA

AEMNETVEVISEMFDLQEPTCLQTRLELYKQGLRGSLTICLKGPLTMMAS

HYKQHCPPTPETSCATQIITFESFICENLICDFLLVIPFDCWEPVQE

Cytosine-Guanosine (CpG) Oligonucleotide (CpG-ODN) Sequences

CpG sites are regions of deoxyribonucleic acid (DNA) where a cysteine nucleotide occurs next to a guanine nucleotide in the linear sequence of bases along its length (the "p" represents the phosphate linkage between them and distinguishes them from a cytosine-guanine complementary base pairing). CpG sites play a pivotal role in DNA methylation, which is one of several endogenous mechanisms cells use to silence gene expression. Methylation of CpG sites within promoter elements can lead to gene silencing. In the case of cancer, it is known that tumor suppressor genes are often silences while oncogenes, or cancer-inducing genes, are expressed. Importantly, CpG sites in the promoter regions of tumor suppressor genes (which prevent cancer formation) have been shown to be methylated while CpG sites in the promoter regions of oncogenes are hypomethylated or unmethylated in certain cancers. The TLR-9 receptor binds unmethylated CpG sites in DNA.

The present invention comprises CpG dinucleotides and oligonucleotides. Contemplated CpG oligonucleotides are isolated from endogenous sources or synthesized in vivo or in vitro. Exemplary sources of endogenous CpG oligonucleotides include, but are not limited to, microorganisms, bacteria, fungi, protozoa, viruses, molds, or parasites. Alternatively, endogenous CpG oligonucleotides are isolated from mammalian benign or malignant neoplastic tumors. Synthetic CpG oligonucleotides are synthesized in vivo following transfection or transformation of template DNA into a host organism. Alternatively, Synthetic CpG oligonucleotides are synthesized in vitro by polymerase chain reaction (PCR) or other art-recognized methods (Sambrook, J., Fritsch, E. F., and Maniatis, T., Molecular Cloning: A Laboratory Manual. Cold Spring Harbor Laboratory Press, NY, Vol. 1, 2, 3 (1989), herein incorporated by reference).

CpG oligonucleotides are presented for cellular uptake by dendritic cells. In one embodiment, naked CpG oligonucleotides are used. The term "naked" is used to describe an isolated endogenous or synthetic polynucleotide (or oligonucleotide) that is free of additional substituents. In another embodiment, CpG oligonucleotides are bound to one or more compounds to increase the efficiency of cellular uptake. Alternatively, or in addition, CpG oligonucleotides are, bound to one or more compounds to increase the stability of the oligonucleotide within the scaffold and/or dendritic cell.

CpG oligonucleotides are condensed prior to cellular uptake. In one preferred embodiment, CpG oligonucleotides are condensed using polyethylenimine (PEI), a cationic polymer that increases the efficiency of cellular uptake into dendritic cells.

CpG oligonucleotides of the present invention can be divided into multiple classes. For example, exemplary CpG-ODNs encompassed by compositions, methods and devices of the present invention are stimulatory, neutral, or suppressive. The term "stimulatory" used herein is meant to describe a class of CpG-ODN sequences that activate TLR9. The term "neutral" used herein is meant to describe a class of CpG-ODN sequences that do not activate TLR9. The term "suppressive" used herein is meant to describe a class of CpG-ODN sequences that inhibit TLR9. The term "activate TLR9" describes a process by which TLR9 initiates intracellular signaling.

Simulatory CpG-ODNs can further be divided into three types A, B and C, which differ in their immune-stimulatory activities. Type A stimulatory CpG ODNs are characterized by a phosphodiester central CpG-containing palindromic motif and a phosphorothioate 3' poly-G string. Following activation of TLR9, these CpG ODNs induce high IFN-α production from plasmacytoid dendritic cells (pDC). Type A CpG ODNs weakly stimulate TLR9-dependent NF-κB signaling.

Type B stimulatory CpG ODNs contain a full phosphorothioate backbone with one or more CpG dinucleotides. Following TLR9 activation, these CpG-ODNs strongly activate B cells. In contrast to Type A Cpg-ODNs, Type B CpG-ODNS weakly stimulate IFN-α secretion.

Type C stimulatory CpG ODNs comprise features of Types A and B. Type C CpG-ODNs contain a complete phosphorothioate backbone and a CpG containing palindromic motif. Similar to Type A CpG ODNs, Type C CpG ODNs induce strong IFN-α production from pDC. Similar to Type B CpG ODNs, Type C CpG ODNs induce strong B cell stimulation.

Exemplary stimulatory CpG ODNs comprise, but are not limited to, ODN 1585, ODN 1668, ODN 1826, ODN 2006, ODN 2006-G5, ODN 2216, ODN 2336, ODN 2395, ODN M362 (all InvivoGen). The present invention also encompasses any humanized version of the preceding CpG ODNs. In one preferred embodiment, compositions, methods, and devices of the present invention comprise ODN 1826 (the sequence of which from 5' to 3' is tccatgacgttcctgacgtt, wherein CpG elements are bolded, SEQ ID NO: 10).

Neutral, or control, CpG ODNs that do not stimulate TLR9 are encompassed by the present invention. These ODNs comprise the same sequence as their stimulatory counterparts but contain GpC dinucleotides in place of CpG dinucleotides.

Exemplary neutral, or control, CpG ODNs encompassed by the present invention comprise, but are not limited to, ODN 1585 control, ODN 1668 control, ODN 1826 control, ODN 2006 control, ODN 2216 control, ODN 2336 control, ODN 2395 control, ODN M362 control (all InvivoGen). The present invention also encompasses any humanized version of the preceding CpG ODNs.

Suppressive CpG ODNs that inhibit TLR9 are encompassed by the present invention. Exemplary potent inhibitory sequences are $(TTAGGG)_4$ (ODN TTAGGG, InvivoGen, SEQ ID NO: 11), found in mammalian telomeres and ODN 2088 (InvivoGen), derived from a murine stimulatory CpG ODN by replacement of 3 bases. Suppressive ODNs disrupt the colocalization of CpG ODNs with TLR9 in endosomal vesicles without affecting cellular binding and uptake. Suppressive CpG ODNs encompassed by the present invention are used to fine-tune, attenuate, reverse, or oppose the action of a stimulatory CpG-ODN. Alternatively, or in addition, compositions, methods, or devices of the present invention comprising suppressive CpG ODNs are used to treat autoimmune conditions or prevent immune responses following transplant procedures.

Cancer Antigens

Compositions, methods, and devices of the present invention comprise cancer antigens with means to vaccinate and/or provide protective immunity to a subject to whom such a device was administered. Cancer antigens are used alone or in combination with GM-CSF, CpG-ODN sequences, or immunomodulators. Moreover, cancer antigens are used simultaneously or sequentially with GM-CSF, CpG-ODN sequences, or immunomodulators.

Exemplary cancer antigens encompassed by the compositions, methods, and devices of the present invention include, but are not limited to, tumor lysates extracted from biopsies, irradiated tumor cells, MAGE series of antigens (MAGE-1 is an example), MART-1/melana, tyrosinase, ganglioside, gp100, GD-2,0-acetylated GD-3, GM-2, MUC-1, Sos1, Protein kinase C-binding protein, Reverse transcriptase protein, AKAP protein, VRK1, KIAA1735, T7-1, T11-3, T11-9, Homo Sapiens telomerase ferment (hTRT), Cytokeratin-19 (CYFRA21-1), SQUAMOUS CELL CARCINOMA ANTIGEN 1 (SCCA-1), (PROTEIN T4-A), SQUAMOUS CELL CARCINOMA ANTIGEN 2 (SCCA-2), Ovarian carcinoma antigen CA125 (1A1-3B) (KIAA0049), MUCIN 1 (TUMOR-ASSOCIATED MUCIN), (CARCINOMA-ASSOCIATED MUCIN), (POLYMORPHIC EPITHELIAL MUCIN), (PEM), (PEMT), (EPISIALIN), (TUMOR-ASSOCIATED EPITHELIAL MEMBRANE ANTIGEN), (EMA), (H23AG), (PEANUT-REACTIVE URINARY MUCIN), (PUM), (BREAST CARCINOMA-ASSOCIATED ANTIGEN DF3), CTCL tumor antigen se1-1, CTCL tumor antigen se14-3, CTCL tumor antigen se20-4, CTCL tumor antigen se20-9, CTCL tumor antigen se33-1, CTCL tumor antigen se37-2, CTCL tumor antigen se57-1, CTCL tumor antigen se89-1, Prostate-specific membrane antigen, 5T4 oncofetal trophoblast glycoprotein, Orf73 Kaposi's sarcoma-associated herpesvirus, MAGE-C1 (cancer/testis antigen CT7), MAGE-B1 ANTIGEN (MAGE-XP ANTIGEN) (DAM10), MAGE-B2 ANTIGEN (DAME), MAGE-2 ANTIGEN, MAGE-4-a antigen, MAGE-4-b antigen, Colon cancer antigen NY-CO-45, Lung cancer antigen NY-LU-12 variant A, Cancer associated surface antigen, Adenocarcinoma antigen ART1, Paraneoplastic associated brain-testis-cancer antigen (onconeuronal antigen MA2; paraneoplastic neuronal antigen), Neuro-oncological ventral antigen 2 (NOVA2), Hepatocellular carcinoma antigen gene 520, TUMOR-ASSOCIATED ANTIGEN CO-029, Tumor-associated antigen MAGE-X2, Synovial sarcoma, X breakpoint 2, Squamous cell carcinoma antigen recognized by T cell, Serologically defined colon cancer antigen 1, Serologically defined breast cancer antigen NY-BR-15, Serologically defined breast cancer antigen NY-BR-16, Chromogranin A; parathyroid secretory protein 1, DUPAN-2, CA 19-9, CA 72-4, CA 195, Carcinoembryonic antigen (CEA).

Immunomodulators

Compositions, methods, and devices of the present invention comprise immunomodulators including, but not limited to, TLR ligands, growth factors, and products of dying cells, e.g. heat shock proteins, with means to stimulate dendritic cell activation. Immunomodulators are used alone or in combination with GM-CSF, CpG-ODN sequences, or cancer antigens. Immunomodulators are used simultaneously or sequentially with GM-CSF, CpG-ODN sequences, or cancer antigens.

All known TLR ligands found either on a cell surface or an internal cellular compartment are encompassed by the compositions, methods, and devices of the present invention. Exemplary TLR ligands include, but are not limited to, triacyl lipoproteins (TLR1); lipoproteins, gram positive peptidoglycan, lipteichoic acids, fungi, and viral glycoproteins (TLR2); double-stranded RNA, poly I:C (TLR 3); lipopolysaccharide, viral glycoproteins (TLR 4); flagellin (TLR5); diacyl lipoproteins (TLR6); small synthetic compounds, single-stranded RNA (TLR7 and TLR 8); unmethylated CpG DNA (TLR9); Profilin (TLR11). Also included as TRL ligands are host molecules like fibronectin and heat shock proteins (HSPs). Host TLR ligands are also encompassed by the present invention. The role of TLRs in innate immunity and the signaling molecules used to activate and inhibit them are known in the art (for a review, see Holger K. Frank B., Hessel E., and Coffman R L. Therapeutic targeting of innate immunity with Toll-like receptor agonists and antagonists. Nature Medicine 13, 552-559 (2007), herein incorporated by reference).

All known growth factors are encompassed by the compositions, methods, and devices of the present invention. Exemplary growth factors include, but are not limited to, transforming growth factor beta (TGF-β), granulocyte-colony stimulating factor (G-CSF), granulocyte-macrophage colony stimulating factor (GM-CSF), nerve growth factor (NGF), neurotrophins, Platelet-derived growth factor (PDGF), erythropoietin (EPO), thrombopoietin (TPO), myostatin (GDF-8), growth differentiation factor-9 (GDF9), acidic fibroblast growth factor (aFGF or FGF-1), basic fibroblast growth factor (bFGF or FGF-2), epidermal growth factor (EGF), hepatocyte growth factor (HGF). The present invention encompasses cytokines as well as growth factors for stimulating dendritic cell activation. Exemplary cytokines include, but are not limited to, IL-1, IL-2, IL-3, IL-4, IL-5, IL-6, IL-8, IL-10, IL-12 IL-15, IL-17, IL-18, TNF-α, IFN-γ, and IFN-α.

Indications of cell death and products of dying cells stimulate dendritic cell activation. As such, all products of dying cells are encompassed by the compositions, methods, and devices of the present invention. Exemplary cell death products include, but are not limited to, any intracellular feature of a cell such as organelles, vesicles, cytoskeletal elements, proteins, DNA, and RNA. Of particular interest are heat shock proteins expressed when a cell is under stress and which are released upon cell death. Exemplary heat shock proteins include, but are not limited to, Hsp10, Hsp20, Hsp27, Hsp33, Hsp40, Hsp60, Hsp70, Hsp71, Hsp72, Grp78, Hsx70, Hsp84, Hsp90, Grp94, Hsp100, Hsp104, Hsp110.

Microenvironments and Vaccine Efficiency

The devices/scaffold described herein represent an infection-mimicking microenvironment. Each device constitutes a factory that attracts/accepts, educates/stimulates and sends forth to surrounding bodily tissues activated dendritic cells that are capable of stimulating/enhancing an immune response to a particular antigen. Specifically, the scaffold devices are implanted or coated with pathogenic molecules to mimic and infectious microenvironment to further activate the dendritic cell response.

Appropriately mimicking aspects of infection with material systems dramatically impacts tumor progression when applied as cancer vaccines by continuously recruiting, activating and homing DCs to LNs. The first PLG vaccine, using GM-CSF alone, led to a batch process where host DCs were recruited by GM-CSF to reside at a site of tumor antigen presentation, and were trapped until GM-CSF levels fell and the cells could become activated and disperse (see U.S. Ser. No. 11/638,796; herein incorporated by reference). Temporal variation of the local GM-CSF concentration allowed control over the number of recruited DCs, and the timing of their activation and dispersement. Although the best GM-CSF-based vaccine was able to confer protective immunity in nearly a quarter of the animals tested, approximately 26% of the recruited DCs were activated (~240,000 DCs) and approximately 6% of DCs dispersed to the LNs. High levels of GM-CSF recruited large numbers of DC, but also limited DC activation, leaving potentially therapeutic DCs entrapped within scaffolds. These results motivated the development of an improved system that mimicked bacterial infection by locally presenting CpG-ODNs as an overriding 'danger signal', that opposed GM-CSF inhibition of DC activation and dispersement. These devices described herein represent significant advances by mediating increased and continuous egress of DCs.

CpG-ODN molecules were condensed with PEI to not only promote ODN uptake into DCs and localization to its TLR-9 receptor (FIG. 3), but also to electrostatically immobilize it in PLG matrices to be presented simultaneously with tumor antigens (FIG. 6). In vitro results indicated that PEI-CpG-ODN condensates can decondense within DCs and stimulate TLR signaling that promoted DC activation and dispersement toward the lymph node derived chemokine, CCL19, in the presence of inhibitory levels of GM-CSF (500 ng/ml).

Figure 7B:
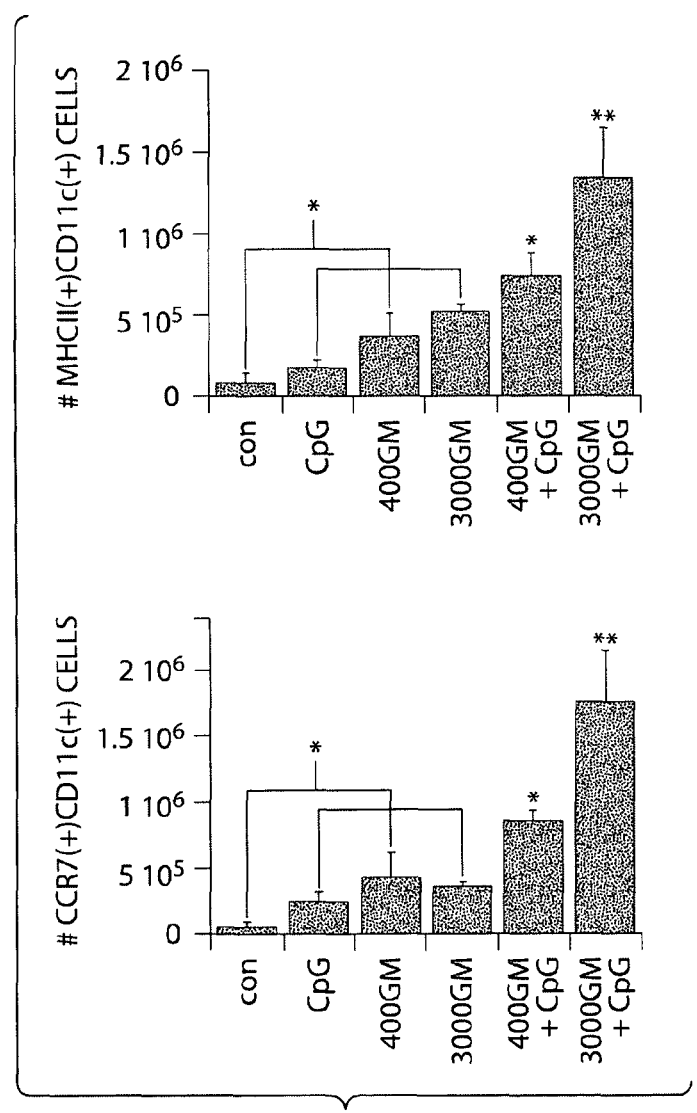
Figure 8A:
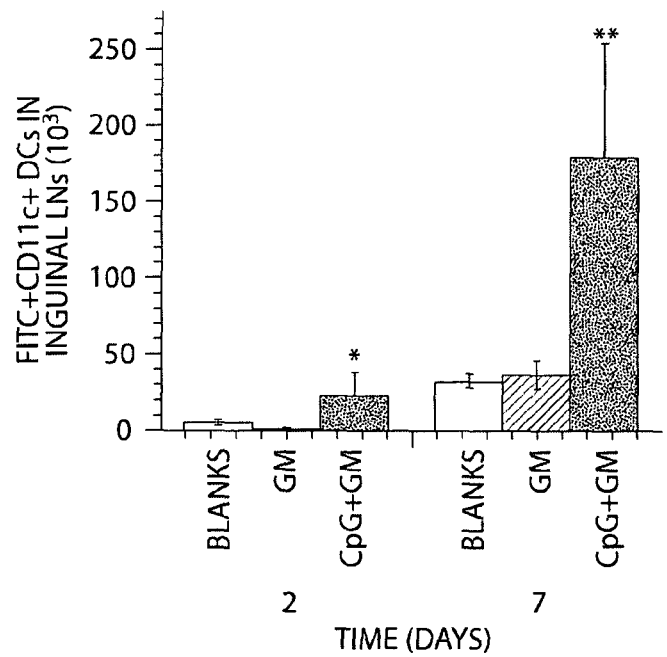
FIGS. 8A-D. Infection mimics continuously disperse programmed DCs in situ.
Figure 8B:
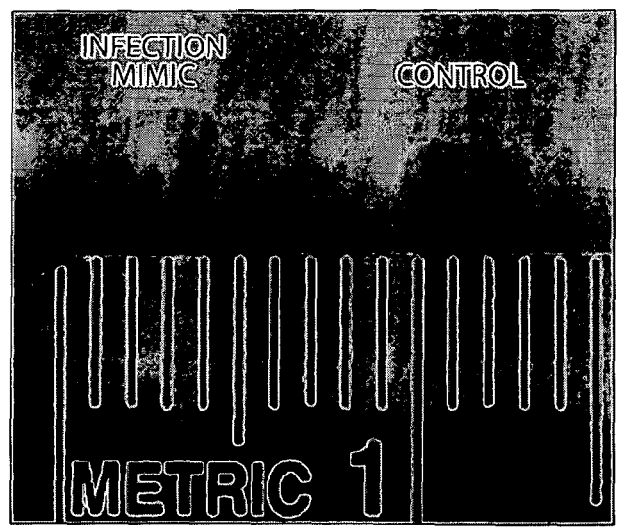
Figure 8C:
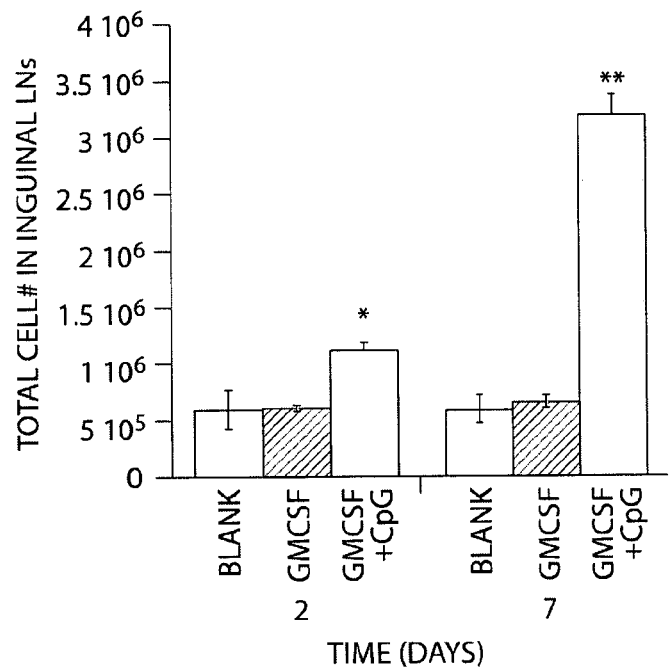
Figure 8D:
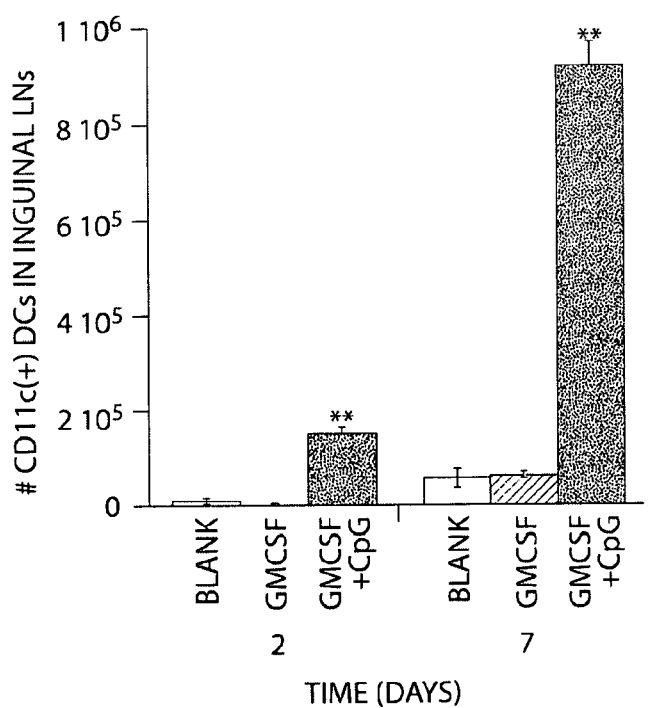

In vivo, appropriately designed infection-mimics mediated a continuous process that shuttled DCs through an infectious-like microenvironment via recruitment with GM-CSF, followed by immediate activation of resident DCS via condensed CpG-ODN presentation, and subsequent release. An in vivo screen of the dose effects of combined CpG-ODN delivery revealed differential effects on DC activation, with an unusual decoupling of CCR7 and MHCII expression, at high CpG-ODN (>50 µg) and GM-CSF (>1 µg) doses, whereas optimal CpG-ODN doses (10-25 µg) induced significant DC activation (44%, and $1.5 \times 10^6$ cells) even when opposed by high GM-CSF levels (3 µg, in vivo). Therefore, optimal CpG-ODN presentation can activate large numbers of DCs recruited by strong GM-CSF pulses in situ, and these numbers exceed the numbers often programmed and transplanted in ex vivo protocols (FIG. 7).

This DC programming process proved to be continuous as DCs were shuttled through an infectious-like microenvironment via recruitment with intense pulses of GM-CSF, followed by the subsequent programming and release of resident DCS via condensed CpG-ODN stimulation. The percentage of DCs that homed to the LNs approximately doubled from 6% to 13% (U.S. Ser. No. 11/638,796 and FIG. 8), which corresponded to 180,000 programmed DCs (~4-fold enhancement compared to devices without CpG-ODN) being dispersed to the lymph nodes, with infection-mimics (FIGS. 7 and 8). Strikingly, the lymph nodes in this condition were markedly enlarged (FIG. 8) and loaded with large numbers of DCs at sacrifice, supporting the conclusion that an infection-mimic was created in those animals.

The ability of these infectious-material systems to continuously control DC trafficking and activation translated to a regulation over the efficacy of the cancer vaccine. As the numbers of material-resident, activated DCs that were programmed and dispersed to the lymph nodes increased, the efficacy increased from 0 to 23 and finally 50%. Host T-cells mediated the immune protection, and a clear relation between the numbers of CD-4 and CD-8 lymphocytes (~50% increase due to infection mimicking) in the tumors that did form (FIG. 10) and vaccine efficacy was found. These results are qualitatively consistent with an ex vivo vaccine developed using irradiated tumor cells engineered to secrete GM-CSF, as that system was previously found to stimulate a potent, specific, and long-lasting anti-tumor immunity (Akira S, Takeda K, Kaisho T. Nature Immunol, 2, 675-80, 2001). In contrast, though, the infection-mimicking material system programmed DCs in situ, and bypassed all ex vivo cell manipulation and transplantation, and provided tight control over the number of DCs recruited, activated and dispersed to the lymph nodes (LNs).

These results indicate the value of finely controlling cell behavior and programming in situ. The mechanism behind vaccine efficacy in these studies was clearly the appropriate control over the number and timing of DC mobilization and programming. Infection-mimics are a useful tool for the development of vaccines with means to create immunity against otherwise lethal infection, cancers and autoimmunity.

Scaffold Compositions and Architecture

Components of the scaffolds are organized in a variety of geometric shapes (e.g., beads, pellets), niches, planar layers (e.g., thin sheets). For example, multicomponent scaffolds are constructed in concentric layers each of which is characterized by different physical qualities (% polymer, % crosslinking of polymer, chemical composition of scaffold, pore size, porosity, and pore architecture, stiffness, toughness, ductility, viscoelasticity, and or composition of bioactive substances such as growth factors, homing/migration factors, differentiation factors. Each niche has a specific effect on a cell population, e.g., promoting or inhibiting a specific cellular function, proliferation, differentiation, elaboration of secreted factors or enzymes, or migration. Cells incubated in the scaffold are educated and induced to migrate out of the scaffold to directly affect a target tissue, e.g., and injured tissue site. For example, stromal vascular cells and smooth muscle cells are useful in sheetlike structures are used for repair of vessel-like structures such as blood vessels or layers of the body cavity. For example, such structures are used to repair abdominal wall injuries or defects such as gastroschisis. Similarly, sheetlike scaffolds seeded with dermal stem cells and/or keratinocytes are used in bandages or wound dressings for regeneration of dermal tissue. The device is placed or transplanted on or next to a target tissue, in a protected location in the body, next to blood vessels, or outside the body as in the case of an external wound dressing. Devices are introduced into or onto a bodily tissue using a variety of known methods and tools, e.g., spoon, tweezers or graspers, hypodermic needle, endoscopic manipulator, endo- or trans-vascular-catheter, stereotaxic needle, snake device, organ-surface-crawling robot (United States Patent Application 20050154376; Ota et al., 2006, Innovations 1:227-231), minimally invasive surgical devices, surgical implantation tools, and transdermal patches. Devices can also be assembled in place, for example by sequentially injecting or inserting matrix materials. Scaffold devices are optionally recharged with cells or with bioactive compounds, e.g., by sequential injection or spraying of substances such as growth factors or differentiation factors.

A scaffold or scaffold device is the physical structure upon which or into which cells associate or attach, and a scaffold composition is the material from which the structure is made. For example, scaffold compositions include biodegradable or permanent materials such as those listed below. The mechanical characteristics of the scaffold vary according to the application or tissue type for which regeneration is sought. It is biodegradable (e.g., collagen, alginates, polysaccharides, polyethylene glycol (PEG), poly(glycolide) (PGA), poly(L-lactide) (PLA), or poly(lactide-co-glycolide) (PLGA) or permanent (e.g., silk). In the case of biodegradable structures, the composition is degraded by physical or chemical action, e.g., level of hydration, heat or ion exchange or by cellular action, e.g., elaboration of enzyme, peptides, or other compounds by nearby or resident cells. The consistency varies from a soft/pliable (e.g., a gel) to glassy, rubbery, brittle, tough, elastic, stiff. The structures contain pores, which are nanoporous, microporous, or macroporous, and the pattern of the pores is optionally homogeneous, heterogenous, aligned, repeating, or random.

Alginates are versatile polysaccharide based polymers that may be formulated for specific applications by controlling the molecular weight, rate of degradation and method of scaffold formation. Coupling reactions can be used to covalently attach bioactive epitopes, such as the cell adhesion sequence RGD to the polymer backbone. Alginate polymers are formed into a variety of scaffold types. Injectable hydrogels can be formed from low MW alginate solutions upon addition of a cross-linking agents, such as calcium ions, while macroporous scaffolds are formed by lyophilization of high MW alginate discs. Differences in scaffold formulation control the kinetics of scaffold degradation. Release rates of morphogens or other bioactive substances from alginate scaffolds is controlled by scaffold formulation to present morphogens in a spatially and temporally controlled manner. This controlled release not only eliminates systemic side effects and the need for multiple injections, but can be used to create a microenvironment that activates host cells at the implant site and transplanted cells seeded onto a scaffold.

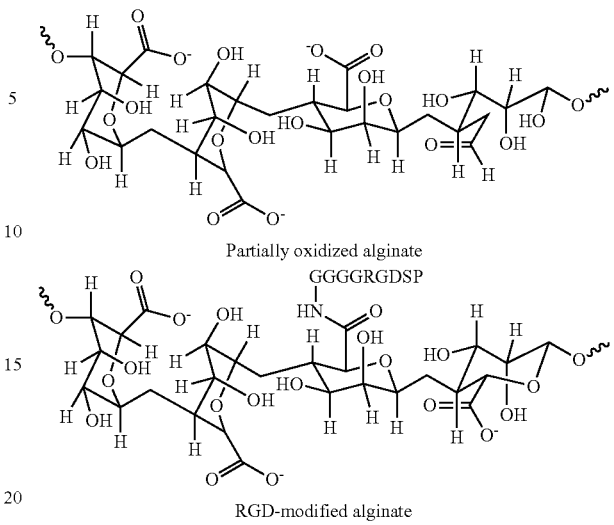

Partially oxidized alginate

RGD-modified alginate

The scaffold comprises a biocompatible polymer matrix that is optionally biodegradable in whole or in part. A hydrogel is one example of a suitable polymer matrix material. Examples of materials which can form hydrogels include polylactic acid, polyglycolic acid, PLGA polymers, alginates and alginate derivatives, gelatin, collagen, agarose, natural and synthetic polysaccharides, polyamino acids such as polypeptides particularly poly(lysine), polyesters such as polyhydroxybutyrate and poly-epsilon-caprolactone, polyanhydrides; polyphosphazines, poly(vinyl alcohols), poly (alkylene oxides) particularly poly(ethylene oxides), poly (allylamines)(PAM), poly(acrylates), modified styrene polymers such as poly(4-aminomethylstyrene), pluronic polyols, polyoxamers, poly(uronic acids), poly(vinylpyrrolidone) and copolymers of the above, including graft copolymers.

The scaffolds are fabricated from a variety of synthetic polymers and naturally-occurring polymers such as, but not limited to, collagen, fibrin, hyaluronic acid, agarose, and laminin-rich gels. One preferred material for the hydrogel is alginate or modified alginate material. Alginate molecules are comprised of (1-4)-linked β-D-mannuronic acid (M units) and a L-guluronic acid (G units) monomers, which can vary in proportion and sequential distribution along the polymer chain. Alginate polysaccharides are polyelectrolyte systems which have a strong affinity for divalent cations (e.g. $Ca^{+2}$, $Mg^{+2}$, $Ba^{+2}$) and form stable hydrogels when exposed to these molecules. See Martinsen A., et al., Biotech. & Bioeng., 33 (1989) 79-89.) For example, calcium cross-linked alginate hydrogels are useful for dental applications, wound dressings chondrocyte transplantation and as a matrix for other cell types.

An exemplary device utilizes an alginate or other polysaccharide of a relatively low molecular weight, preferably of size which, after dissolution, is at the renal threshold for clearance by humans, e.g., the alginate or polysaccharide is reduced to a molecular weight of 1000 to 80,000 daltons. Preferably, the molecular mass is 1000 to 60,000 daltons, particularly preferably 1000 to 50,000 daltons. It is also useful to use an alginate material of high guluronate content since the guluronate units, as opposed to the mannuronate units, provide sites for ionic crosslinking through divalent cations to gel the polymer. U.S. Pat. No. 6,642,363, incorporated herein by reference discloses methods for making and using polymers containing polysaccharides such as alginates or modified alginates that are particularly useful for cell transplantation and tissue engineering applications.

Useful polysaccharides other than alginates include agarose and microbial polysaccharides such as those listed in the table below.

Polysaccharide Scaffold Compositions

| Polymers[a] | Structure |
|---|---|
| Fungal | |
| Pullulan (N) | 1,4-;1,6-α-D-Glucan |
| Scleroglucan (N) | 1,3;1,6-α-D-Glucan |
| Chitin (N) | 1,4-β-D-Acetyl Glucosamine |
| Chitosan (C) | 1,4-β.-D-N-Glucosamine |
| Elsinan (N) | 1,4-;1,3-α-D-Glucan |
| Bacterial | |
| Xanthan gum (A) | 1,4-β.-D-Glucan with D-mannose; D-glucuronic Acid as side groups |
| Curdlan (N) | 1,3-β.-D-Glucan (with branching) |
| Dextran (N) | 1,6-α-D-Glucan with some 1,2;1,3-; 1,4-α-linkages |
| Gellan (A) | 1,4-β.-D-Glucan with rhamose, D-glucuronic acid |
| Levan (N) | 2,6-β-D-Fructan with some β-2,1-branching |
| Emulsan (A) | Lipoheteropolysaccharide |
| Cellulose (N) | 1,4-β-D-Glucan |

[a]N-neutral, A = anionic and C = cationic.

The scaffolds of the invention are porous or non-porous. For example, the scaffolds are nanoporous having a diameter of less than about 10 nm; microporous wherein the diameter of the pores are preferably in the range of about 100 nm-20 µm; or macroporous wherein the diameter of the pores are greater than about 20 µm, more preferably greater than about 100 µm and even more preferably greater than about 400 µm. In one example, the scaffold is macroporous with aligned pores of about 400-500 µm in diameter. The preparation of polymer matrices having the desired pore sizes and pore alignments are described in the Examples. Other methods of preparing porous hydrogel products are known in the art. (U.S. Pat. No. 6,511,650 incorporated herein by reference).

Bioactive Compositions

The device includes one or more bioactive compositions. Bioactive compositions are purified naturally-occurring, synthetically produced, or recombinant compounds, e.g., polypeptides, nucleic acids, small molecules, or other agents. For example, the compositions include GM-CSF, CpG-ODN, and tumor antigens or other antigens. The compositions described herein are purified. Purified compounds are at least 60% by weight (dry weight) the compound of interest. Preferably, the preparation is at least 75%, more preferably at least 90%, and most preferably at least 99%, by weight the compound of interest. Purity is measured by any appropriate standard method, for example, by column chromatography, polyacrylamide gel electrophoresis, or HPLC analysis.

Coupling of the polypeptides to the polymer matrix is accomplished using synthetic methods known to one of ordinary skill in the art. Approaches to coupling of peptides to polymers are discussed in Hirano and Mooney, *Advanced Materials*, p. 17-25 (2004). Other useful bonding chemistries include those discussed in Hermanson, *Bioconjugate Techniques*, p. 152-185 (1996), particularly by use of carbodiimide couplers, DCC and DIC (Woodward's Reagent K). Polypeptides contain a terminal amine group for such carbodiimide bonding. The amide bond formation is preferably catalyzed by 1-ethyl-3-(3-dimethylaminopropyl)carbodiimide (EDC), which is a water soluble enzyme commonly used in peptide synthesis.

Control of Release Kinetics of Bioactive Compositions

The release profile of bioactive compositions such as GM-CSF is controlled using a number of different techniques, e.g., encapsulation, nature of attachment/association with the scaffold, porosity of the scaffold, and particle size of the bioactive compositions.

For example, GM-CSF is encapsulated as one means by which to incorporate GM-CSF into the scaffolds. GM-CSF was first encapsulated into PLG microspheres, and then these GM-CSF loaded microspheres were then in a gas foaming process to develop macroporous PLG scaffolds. The incorporation of GM-CSF into the microspheres causes the GM-CSF to be more deeply embedded into the polymer, which causes the device to sustain the initial pulse of GM-CSF delivery over days 1-5. Other incorporation methods are optionally used to alter or fine tune the duration of the GM-CSF pulse as desired, which would in turn change the kinetics of DC recruitment. For example, foaming PLG particles mixed with lyophilized GM-CSF results in GM-CSF that is associated more with the surface of the polymer scaffold, and the protein diffuses more quickly.

Alternative methods for scaffold fabrication that modify release kinetics include modifying the physical structure of the scaffolds pores, thereby leading to different degradation times and release kinetics (change pore size or total porosity as a percentage of volume), e.g., as described in Riddle et al., Role of poly(lactide-co-glycolide) particle size on gas-foamed scaffolds. J Biomater Sci Polym Ed. 2004; 15(12): 1561-70. Another way to alter release kinetics is to modify the composition, i.e., the raw materials from which the scaffold is made, thereby altering the release properties. For example, different polymers, e.g. alginate, PLA, PGA, or using PLGA are used. Also, use of the polymers with different ratios of glycolic and lactic acid) leads to different release profiles. For example, a variety of PLGs, differing in composition (lactide to glycolide ratio) and molecular weight are used to prepare microspheres (5-50 µm) using known double emulsion (water/oil/water) process, followed by preparation of scaffolds using particulate PLG and PLG microspheres using gas foaming/particulate leaching techniques (Ennett et al., Temporally regulated delivery of VEGF in vitro and in vivo. J Biomed Mater Res A. 2006 October; 79(1). Another technique involves incorporating the protein into different compartments (e.g., encapsulating proteins PLG microspheres or simple mixing and lyophilizing with the polymer before foaming).

Charging and/or Recharging the Device

A bioactive composition such as GM-CSF is incorporated within different layers/compartments of the device, thereby allowing multiple pulses of GM-CSF to be delivered. Each pulse charges (or recharges) the device with an influx of DCs. Scaffolds are fabricated using a variety of methods to create multiple pulses of GM-CSF (or other bioactive agents). For example, such devices are made by incorporating the protein into different compartments (e.g encapsulating proteins PLG microspheres or simple mixing and lyophilizing with the polymer before foaming) thereby creating 2 or more distinct release profiles (i.e. pulses) of the protein (e.g., as described in Richardson et al., Polymeric system for dual growth factor delivery. Nat Biotechnol. 2001 November; 19(11)).

Alternatively, the protein is encapsulated in fast degrading PLG microspheres (e.g. low MW, 50:50 ratio) and slow degrading PLG microspheres (high MW, 85:15 ratio). Then these microspheres are mixed together to be used later to fabricate the scaffolds. Therefore, the protein is encapsulated in both fast a degrading polymer and a slow degrading polymer, thereby resulting in at least 2 distinct releases kinetics and pulses of delivery. This method is utilized to create 3, 4, 5, or more different kinds of microspheres, the ratiometric characteristics of which differ, thereby leading to 3, 4, 5 or more pulses of release of the bioactive composition such as GM-CSF.

Another approach to making a device that delivers more than one pulse is to fabricate a layered scaffold. Layered scaffolds are made by compression molding on different scaffold formulations with another. For example, the raw materials (sucrose+PLG1+Protein) is compressed in a mold and a slightly varied formulation (sucrose+PLG2+Protein) is also compressed in a mold. Then these two layers are compressed together and then foamed, resulting in a bilayered scaffold with distinct spatial control of the concentration of the protein, e.g., as described in Chen et al., Pharm Res. Spatio-temporal VEGF and PDGF delivery patterns blood vessel formation and maturation. 2007 February; 24(2):258-64).

Device Construction

The scaffold structure is constructed out of a number of different rigid, semi-rigid, flexible, gel, self-assembling, liquid crystalline, or fluid compositions such as peptide polymers, polysaccharides, synthetic polymers, hydrogel materials, ceramics (e.g., calcium phosphate or hydroxyapatite), proteins, glycoproteins, proteoglycans, metals and metal alloys. The compositions are assembled into cell scaffold structures using methods known in the art, e.g., injection molding, lyophilization of preformed structures, printing, self-assembly, phase inversion, solvent casting, melt processing, gas foaming, fiber forming/processing, particulate leaching or a combination thereof. The assembled devices are then implanted or administered to the body of an individual to be treated.

The device is assembled in vivo in several ways. The scaffold is made from a gelling material, which is introduced into the body in its ungelled form where it gels in situ. Exemplary methods of delivering device components to a site at which assembly occurs include injection through a needle or other extrusion tool, spraying, painting, or methods of deposit at a tissue site, e.g., delivery using an application device inserted through a cannula. In one example, the ungelled or unformed scaffold material is mixed with bioactive substances and cells prior to introduction into the body or while it is introduced. The resultant in vivo/in situ assembled scaffold contains a mixture of these substances and cells.

In situ assembly of the scaffold occurs as a result of spontaneous association of polymers or from synergistically or chemically catalyzed polymerization. Synergistic or chemical catalysis is initiated by a number of endogenous factors or conditions at or near the assembly site, e.g., body temperature, ions or pH in the body, or by exogenous factors or conditions supplied by the operator to the assembly site, e.g., photons, heat, electrical, sound, or other radiation directed at the ungelled material after it has been introduced. The energy is directed at the scaffold material by a radiation beam or through a heat or light conductor, such as a wire or fiber optic cable or an ultrasonic transducer. Alternatively, a shear-thinning material, such as an amphiphile, is used which re-cross links after the shear force exerted upon it, for example by its passage through a needle, has been relieved.

Suitable hydrogels for both in vivo and ex vivo assembly of scaffold devices are well known in the art and described, e.g., in Lee et al., 2001, Chem. Rev. 7:1869-1879. The peptide amphiphile approach to self-assembly assembly is described, e.g., in Hartgerink et al., 2002, Proc. Natl. Acad. Sci. U.S.A. 99:5133-5138. A method for reversible gellation following shear thinning is exemplied in Lee et al., 2003, Adv. Mat. 15:1828-1832.

A multiple compartment device is assembled in vivo by applying sequential layers of similarly or differentially doped gel or other scaffold material to the target site. For example, the device is formed by sequentially injecting the next, inner layer into the center of the previously injected material using a needle, forming concentric spheroids. Non-concentric compartments are formed by injecting material into different locations in a previously injected layer. A multi-headed injection device extrudes compartments in parallel and simultaneously. The layers are made of similar or different scaffolding compositions differentially doped with bioactive substances and different cell types. Alternatively, compartments self-organize based on their hydrophilic/phobic characteristics or on secondary interactions within each compartment.

Compartmentalized Device

In certain situations, a device containing compartments with distinct chemical and/or physical properties is useful. A compartmentalized device is designed and fabricated using different compositions or concentrations of compositions for each compartment.

Alternatively, the compartments are fabricated individually, and then adhered to each other (e.g., a "sandwich" with an inner compartment surrounded on one or all sides with the second compartment). This latter construction approach is accomplished using the intrinsic adhesiveness of each layer for the other, diffusion and interpenetration of polymer chains in each layer, polymerization or cross-linking of the second layer to the first, use of an adhesive (e.g., fibrin glue), or physical entrapment of one compartment in the other. The compartments self-assemble and interface appropriately, either in vitro or in vivo, depending on the presence of appropriate precursors (e.g., temperature sensitive oligopeptides, ionic strength sensitive oligopeptides, block polymers, cross-linkers and polymer chains (or combinations thereof), and precursors containing cell adhesion molecules that allow cell-controlled assembly).

Alternatively, the compartmentalized device is formed using a printing technology. Successive layers of a scaffold precursor doped with bioactive substances is placed on a substrate then cross linked, for example by self-assembling chemistries. When the cross linking is controlled by chemical-, photo- or heat-catalyzed polymerization, the thickness and pattern of each layer is controlled by a masque, allowing complex three dimensional patterns to be built up when un-cross-linked precursor material is washed away after each catalyzation. (W T Brinkman et al., Photo-cross-linking of type 1 collagen gels in the presence of smooth muscle cells: mechanical properties, cell viability, and function. *Biomacromolecules,* 2003 July-August; 4(4): 890-895; W. Ryu et al., The construction of three-dimensional microfluidic scaffolds of biodegradable polymers by solvent vapor based bonding of micro-molded layers. *Biomaterials,* 2007 February; 28(6): 1174-1184; Wright, Paul K. (2001). 21*st Century manufacturing*. New Jersey: Prentice-Hall Inc.) Complex, multi-compartment layers are also built up using an inkjet device which "paints" different doped-scaffold precursors on different areas of the substrate. Julie Phillippi (Carnegie Mellon University) presentation at the annual meeting of the American Society for Cell Biology on Dec. 10, 2006; Print me a heart and a set of arteries, Aldhouse P., New Scientist 13 Apr. 2006 Issue 2547 p 19; Replacement organs, hot off the press, C. Choi, New Scientist, 25 Jan. 2003, v2379. These layers are built-up into complex, three dimensional compartments. The device is also built using any of the following methods: Jetted Photopolymer, Selective Laser Sintering, Laminated Object Manufacturing, Fused Deposition Modeling, Single Jet Inkjet, Three Dimensional Printing, or Laminated Object Manufacturing.

The release profiles of bioactive substances from scaffold devices is controlled by both factor diffusion and polymer degradation, the dose of the factor loaded in the system, and the composition of the polymer. Similarly, the range of action (tissue distribution) and duration of action, or spatiotemporal gradients of the released factors are regulated by these variables. The diffusion and degradation of the factors in the tissue of interest is optionally regulated by chemically modifying the factors (e.g., PEGylating growth factors). In both cases, the time frame of release determines the time over which effective cell delivery by the device is desired.

The bioactive substances are added to the scaffold compositions using known methods including surface absorption, physical immobilization, e.g., using a phase change to entrap the substance in the scaffold material. For example, a growth factor is mixed with the scaffold composition while it is in an aqueous or liquid phase, and after a change in environmental conditions (e.g., pH, temperature, ion concentration), the liquid gels or solidifies thereby entrapping the bioactive substance. Alternatively, covalent coupling, e.g., using alkylating or acylating agents, is used to provide a stable, long term presentation of a bioactive substance on the scaffold in a defined conformation. Exemplary reagents for covalent coupling of such substances are provided in the table below.

| Methods to covalently couple peptides/proteins to polymers | | |
|---|---|---|
| Functional Group of Polymer | Coupling reagents and cross-linker | Reacting groups on proteins/peptides |
| —OH | Cyanogen bromide (CNBr) Cyanuric chloride 4-(4,6-Dimethoxy-1,3,5-triazin-2-yl)-4-methyl-morpholinium chloride (DMT-MM) | —NH$_2$ |
| —NH$_2$ | Diisocyanate compounds Diisothoncyanate compounds Glutaraldehyde Succinic anhydride | —NH$_2$ —OH |
| —NH$_2$ | Nitrous Acid Hydrazine + nitrous acid | —NH$_2$ —SH —Ph—OH |
| —NH$_2$ | Carbodiimide compounds (e.g., EDC, DCC)[a] DMT-MM | —COOH |
| —COOH | Thionyl chloride N-hydroxysuccinimide N-hydroxysulfosuccinimide + EDC | —NH$_2$ |
| —SH | Disulfide compound | —SH |

[a]EDC: 1-ethyl-3-(3-dimethylaminopropyl) carbodiimide hydrochloride; DCC: dicyclohexylcarbodiimide Bioactive substances suitable for use in the present invention include, but are not limited to: interferons, interleukins, chemokines, cytokines, colony stimulating factors, chemotactic factors, granulocyte/macrophage colony stimulating factor (GMCSF). Splice variants of any of the above mentioned proteins, and small molecule agonists or antagonists thereof that may be used advantageously to activate dendritic cells are also contemplated herein.

Examples of cytokines as mentioned above include, but are not limited to IL-1, IL-2, IL-3, IL-4, IL-5, IL-6, IL-7, IL-8, IL-10, IL-12, IL-15, IL-17, IL-18, granulocyte-macrophage colony stimulating factor (GM-CSF), granulocyte colony stimulating factor (G-CSF), interferon-γ (γ-IFN), IFN-α, tumor necrosis factor (TNF), TGF-β, FLT-3 ligand, and CD40 ligand.

Scaffolds of the invention optionally comprise at least one non-viral gene therapy vector such that either the transplanted cells or host cells in the vicinity of the implant would take up and express gene that lead to local availability of the desired factor for a desirable time frame. Such non-viral vectors include, but are not limited to, cationic lipids, polymers, targeting proteins, and calcium phosphate.

Scaffold Fabrication.

A 85:15, 120 kD copolymer of D,L-lactide and glycolide (PLG) (Alkermes, Cambridge, Mass.) was utilized in a gas-foaming process to form scaffolds (Cohen S., Yoshioka T., Lucarelli, M., Hwang L. H., and Langer R. Pharm. Res. 8, 713-720 (1991); herein incorporated by reference). PLG microspheres encapsulating GM-CSF were made using standard double emulsion (Harris, L. D., Kim, B. S., and Mooney, D. J. J. Biomed. Mater. Res. 42, 396-402 (1998); herein incorporated by reference). 16 mg of PLG microspheres were then mixed with 150 mg of the porogens, NaCl or sucrose (sieved to a particle size between 250 μm and 425 μm), and compression molded. The resulting disc was allowed to equilibrate within a high-pressure $CO_2$ environment, and a rapid reduction in pressure causes the polymer particles to expand and fuse into an interconnected structure. The NaCl was leached from the scaffolds by immersion in water yielding scaffolds that were 90% porous. To incorporate tumor lysates into PLG scaffolds, biopsies of B16-F10 tumors, that had grown subcutaneously in the backs of C57BL/6J mice (Jackson Laboratory, Bar Harbor Me.), were digested in collagenase (250 U/ml) (Worthington, Lakewood, N.J.) and suspended at a concentration equivalent to $10^7$ cells per ml after filtration through 40 μm cell strainers. The tumor cell suspension was subjected to 4 cycles of rapid freeze in liquid nitrogen and thaw (37° C.) and then centrifuged at 400 rpm for 10 min. The supernatant (1 ml) containing tumor lysates was collected and lyophilized with the PLG microspheres and the resulting mixture was used to make PLG scaffold-based cancer vaccines. To incorporate CpG-ODNs into PLG scaffolds, PEI-CpG-ODN condensate solutions were vortexed with 60 μl of 50% (wt/vol) sucrose solution, lyophilized and mixed with dry sucrose to a final weight of 150 mg. The sucrose containing PEI-CpG-ODN condensate was then mixed with blank, GM-CSF and/or tumor lysate loaded PLG microspheres to make PLG cancer vaccines.

Scaffold compositions of the present invention comprise GM-CSF and CpG-ODN sequences. A range of concentrations of each element are contemplated. In a preferred embodiment, the scaffold composition comprises PLG. With respect to GM-CSF, per 40 mg polymeric scaffold composition, 0-100 μg of GM-CSF polypeptide is incorporated into or coated onto said scaffold composition. Alternatively, doses comprising 0-50 μg, 0-25 μg, 0-10 μg, 0-5 μg, and 0-3 μg of GM-CSF are incorporated into the scaffold composition. In a preferred embodiment, 0-3 μg of GM-CSF are incorporated into the scaffold composition. With respect to CpG-ODN sequences, or PEI-CpG-ODN condensates, per 40 mg polymeric scaffold composition, 0-1000 μg of PEI- CpG-ODN is incorporated into or coated onto said scaffold composition. Alternatively, doses comprising 0-500 μg, 0-250 μg, 0-100 μg, 0-50 μg, 0-25 μg, 0-10 μg, and 0-5 μg of PEI-CpG-ODN are incorporated into the scaffold composition. In a preferred embodiment, 0-50 μg of PEI-CpG-ODN are incorporated into the scaffold composition.

CpG-ODN Incorporation and In Vitro Release Studies

To determine the incorporation efficiency of CpG-ODN incorporation, PLG scaffolds were prepared with 50 ug of CpG-ODN and digested in 1 ml of chloroform (Sigma Aldrich, and washed with 2 mls of aqueous buffer. The aqueous phase was isolated and the amount of CpG-ODN incorporated was determined by absorbance readings (260/280 and 260/230 ratios calculated at 0.2 mm pathlength) using a Nanodrop instrument, ND1000 (Nanodrop technologies, Wilmington, Del.). Similarly, to determine CpG-ODN release kinetics CpG-ODN loaded scaffolds were placed in 1 ml of Phosphate Buffer Solution (PBS) in an incubator (37° C.). At various timepoints, the PBS release media was collected and replaced with fresh media. The total amount of CpG-ODN incorporated into PLG scaffolds and released into PBS over time was analyzed and recorded.

In Vitro DC Migration Assays and DC Activation

A DC line, JAWSII (ATCC, Manassas, Va.) was used for in vitro experiments and was maintained in α-MEM (Invitrogen, Carlsbad, Calif.) supplemented with 20% FBS (Invitrogen, Carlsbad, Calif.) and 5 ng/ml of GM-CSF. To determine the in vitro effects of CpG-rich oligonucleotides (CpG-ODN) on DC activation, JAWSII cells were cultured with 5 μg/ml of CpG-ODN 1826, 5'-tcc atg acg ttc ctg acg tt-3', (Invivogen, San Diego, Calif.) for 24 hours, and in the presence of 0, 50 or 500 ng/ml GM-CSF for 12 hours. To assess the effects of condensing CpG-ODN on DC activation, CpG ODN was condensed with PEI molecules by dropping ODN-1826 solutions into PEI solution, while vortexing the mixture (Huang Y C, Riddle F, Rice K G, and Mooney D J. Hum Gene Ther. 5, 609-17. (2005); herein incorporated by reference). The charge ratio between PEI and CpG-ODN (NH3+:PO4−) was kept constant at 7 during condensation. As a positive control for DC activation, DCs were also cultured with the stimulatory factors, TNF-α (10 ng/ml) (Peprotech, Rocky Hill, N.J.) and LPS (10 ng/ml) (Sigma-Aldrich, St. Louis, Mo.). The DCs were then harvested and stained with primary antibodies (BD Pharmingen, San Diego, Calif.): PE-conjugated CD86 (B7, costimulatory molecule), FITC-conjugated CCR7, and FITC-conjugated MHCII. Cells were analyzed by FACS and gated according to positive FITC, and PE using isotype controls, and the percentage of cells staining positive for each surface antigen was recorded.

Migration assays were performed with 6.5 mm transwell dishes (Costar, Cambridge, Mass.) with a pore size of 5 μm. To test whether CpG-ODN stimulation may affect DC chemotaxis towards CCL19 (Peprotech, Rocky Hill, N.J.) in the presence of GM-CSF, 5×10⁵ DCs stimulated with either 5 μg/ml of CpG-ODN or PEI-CPG-ODN (Charge Ratio of 7), and 0, 50 and 500 ng/ml GM-CSF were placed in the top wells and 300 ng/ml of CCL19 was placed in the bottom well. After 12 hours the cells that migrated into the bottom wells of the chamber were harvested and counted using a coulter counter. Dispersement of DCs from PEI-CpG-ODN loaded PLG matrices toward CCL19 was assessed by incorporating 5, 50 and 500 μg of condensates into PLG scaffolds (13 mm diameter, 2 mm thick that were quartered) seeded with 1×10⁶ DCs and fixed onto transwells using bovine collagen (BD Biosciences, San Jose, Calif.). To test the effects of CpG stimulation in the presence of GM-CSF, 500 ng/ml of GM-CSF was supplemented into the media of the top wells with scaffolds containing 25 μg of PEI-CpG-ODN. At various timepoints, the cells that migrated into the bottom wells of the chamber were harvested and counted using a coulter counter.

In Vivo DC Migration and Activation Assays

Blank scaffolds and scaffolds containing GM-CSF with or without 10 μg PEI-ODN control (5'-tcc atg agc ttc ctg agc tt-3') or 10 μg PEI-CpG-ODN condensate loaded scaffolds were implanted into subcutaneous pockets on the back of 7-9 week old male C57BL/6J mice. For histological examination scaffolds were excised and fixed in Z-fix solution, embedded in paraffin, and stained with hematoxylin and eosin. To analyze DC recruitment, scaffolds were excised and the ingrown tissue was digested into single cell suspensions using a collagenase solution (Worthingtion, 250 U/ml) that was agitated at 37° C. for 45 minutes. The cell suspensions were then poured through a 40 μm cell strainer to isolate cells from scaffold particles and the cells were pelleted and washed with cold PBS and counted using a Z2 coulter counter (Beckman Coulter). The resultant cell populations were then stained with primary antibodies (BD Pharmingen, San Diego, Calif.) conjugated to fluorescent markers to allow for analysis by flow cytometry. APC-conjugated CD11c (dendritic cell marker) and PE-conjugated CD86 (B7, costimulatory molecule) stains were conducted for DC recruitment analysis, and APC-conjugated CD11c, FITC-conjugated CCR7, and PE-conjugated MHCII stains were conducted for DC programming analysis. Cells were gated according to positive FITC, APC and PE using isotype controls, and the percentage of cells staining positive for each surface antigen was recorded. To track in vivo DC emigration from scaffolds toward the inguinal lymph nodes, 250 μg of lyophilized fluoroscein isothiocyanate (FITC) (Molecular Probes, Carlsbad, Calif.) was incorporated into scaffolds by mixing with PLG microspheres before scaffold processing, and FITC was also applied by incubating scaffolds with 330 ul of 3% FITC solution for 30 min. FITC painted scaffolds were then implanted subcutaneously into the left flank of C57BL/6J mice and the inguinal lymph nodes (LNs) were harvested at various time-points after scaffold implantation. Cell suspensions from LNs were prepared by digestion in collagenase for 30 min and pressing of the tissue through 70 μm cell strainers, and examined for CD11c(+)FITC(+) cell numbers by flow cytometry.

Tumor Growth Assays

PLG scaffolds with melanoma tumor lysates and various dosages of GM-CSF and/or 10 μg PEI-CpG-ODN condensates were implanted subcutaneously into the lower left flank of C57BL/6J mice. Animals were challenged 14 days later with a subcutaneous injection of 10⁵ B16-F10 melanoma cells (ATCC, Manassas, N.J.) in the back of the neck. Animals were monitored for the onset of tumor growth (approximately 1 mm³) and sacrificed for humane reasons when tumors grew to 20-25 mm (longest diameter). For histological examination, tumors were biopsied at days 20-25 after injection and fixed in Z-fix (Anatech, Battle Creek, Mich.) and stained for hematoxylin and eosin. To examine tumor tissue for T-cell infiltration, immunoperoxidase staining was performed using the avidin-biotin-peroxidase Vectastain Elite ABC kit (Vector Laboratories). The primary antibodies used were GK 1.5 (CD4), and 53-6.72 (CD8) and staining was developed using DAB+ substrate chromogen (DAKO, Carpinteria, Calif.). Sections from tumor samples (n=3 or 4) were visualized at 40× and 100× with a Nikon light microscope (Indianapolis, Ind.) and positively stained T-cells were counted manually. PLG cancer vaccines were also compared to a common cell-based vaccine using B16-F10 melanoma cells that were genetically modified to express GM-CSF, and subsequently irradiated (3500 rad) as described previously (Dranoff G., et al. Proc. Natl. Acad. Sci. USA. 90, 3539-3543 (1993); herein incorporated by reference). The irradiated tumor cells ($5 \times 10^5$ cells) were then injected subcutaneously into C57BL/6J mice that were challenged 14 days later with $10^5$ B16-F10 melanoma cells.

Statistical Analysis

All values in the present study were expressed as mean±S.D. The significant differences between the groups were analyzed by a Student's t test and a P value of less than 0.05 was considered significant.

Vaccine Device

The biocompatible scaffolds are useful as delivery vehicles for cancer vaccines. The cancer vaccine stimulates an endogenous immune response against cancer cells. Currently produced vaccines predominantly activate the humoral immune system (i.e., the antibody dependent immune response). Other vaccines currently in development are focused on activating the cell-mediated immune system including cytotoxic T lymphocytes which are capable of killing tumor cells. Cancer vaccines generally enhance the presentation of cancer antigens to both antigen presenting cells (e.g., macrophages and dendritic cells) and/or to other immune cells such as T cells, B cells, and NK cells. Although cancer vaccines may take one of several forms, their purpose is to deliver cancer antigens and/or cancer associated antigens to antigen presenting cells (APC) in order to facilitate the endogenous processing of such antigens by APC and the ultimate presentation of antigen presentation on the cell surface in the context of MHC class I molecules. One form of cancer vaccine is a whole cell vaccine which is a preparation of cancer cells which have been removed from a subject, treated ex vivo and then reintroduced as whole cells in the subject. These treatments optionally involve cytokine exposure to activate the cells, genetic manipulation to overexpress cytokines from the cells, or priming with tumor specific antigens or cocktails of antigens, and expansion in culture. Dendritic cell vaccines activate antigen presenting cells directly, and their proliferation, activation and migration to lymph nodes is regulated by scaffold compositions to enhance their ability to elicit an immune response. Types of cancers to be treated include central nervous system (CNS) cancers, CNS Germ Cell tumor, lung cancer, Leukemia, Multiple Myeloma, Renal Cancer, Malignant Glioma, Medulloblastoma, and Melanoma.

For the purpose of eliciting an antigen-specific immune response, a scaffold device is implanted into a mammal. The device is tailored to activate immune cells and prime the cells with a specific antigen thereby enhancing immune defenses and destruction of undesired tissues and targeted microorganisms such as bacterial or viral pathogens. The device attracts appropriate immune cells, such as macrophages, T cells, B cells, NK cells, and dendritic cells, by containing and/or releasing signaling substances such as GM-CSF. These signaling substances are incorporated in the scaffold composition in such a way as to control their release spatially and temporally using the same techniques used to integrate other bioactive, compounds in the scaffold composition.

Once the immune cells are inside the device, the device programs the immune cells to attack or cause other aspects of the immune system to attack undesired tissues (e.g., cancer, adipose deposits, or virus-infected or otherwise diseased cells) or microorganisms. Immune cell activation is accomplished by exposing the resident immune cells to preparations of target-specific compositions, e.g., ligands found on the surface of the undesired tissues or organisms, such as cancer cell surface markers, viral proteins, oligonucleotides, peptide sequences or other specific antigens. For example, useful cancer cell-specific antigens and other tissue or organism-specific proteins are listed in the table below.

The device optionally contains multiple ligands or antigens in order to create a multivalent vaccine. The compositions are embedded in or coated on the surface of one or more compartments of the scaffold composition such that immune cells migrating through the device are exposed to the compositions in their traverse through the device. Antigens or other immune stimulatory molecules are exposed or become exposed to the cells as the scaffold composition degrades. The device may also contain vaccine adjuvants that program the immune cells to recognize ligands and enhance antigen presentation. Exemplary vaccine adjuvants include chemokines/cytokines, CpG rich oligonucleotides. or antibodies that are exposed concurrently with target cell-specific antigens or ligands.

The device attracts immune cells to migrate into a scaffold where they are educated in an antigen-specific manner and activated. The programmed immune cells are then induced to egress towards lymph nodes in a number of ways. The recruitment composition and deployment signal/composition, e.g., a lymph node migration inducing substance, is released in one or more bursts, programmed by the method of incorporation and/or release from the scaffold material, or controlled by the sequential degradation of scaffold compartments which contain the attractant. When a burst dissipates, the cells migrate away. Compartments containing repulsive substances are designed to degrade and release the repulsive substance in one or more bursts or steadily over time. Relative concentration of the repulsive substances cause the immune cells to migrate out of the device. Alternatively, cells which have been placed in or have migrated into the device are programmed to release repulsive substances or to change their own behavior. For example, localized gene therapy is carried out by cell exposure to plasmid DNA attached to the scaffold. Useful repulsive substances include chemokines and cytokines. Alternatively, the device may cause immune cells to egress by degrading and releasing them.

Target disease states, stimulatory molecules and antigens useful in vaccine device construction are listed below.

Bioactive Factors to Promote Immune Responses a. Interleukins: IL-1, IL-2, IL-3, IL-4, IL-5, IL-6, IL-8, IL-10, IL-12 IL-15, IL-17, IL-18 etc.
b. TNF-α
c. IFN-γ
d. IFN-α
e. GM-CSF
f. G-CSF
g. Ftl-3 ligand
h. MIP-3β (CCL19)
i. CCL21
j. M-CSF
k. MIF
l. CD40L
m. CD3
n. ICAM
o. Anti CTLA-4 antibodies
p. TGF-β
q. CPG rich DNA or oligonucleotides r. Sugar moieties associated with Bacteria: Lipopolysacharides (LPS) is an example
s. Fas ligand
t. Trail
u. Lymphotactin
v. Mannan (M-FP)
w. Heat Shock Proteins (apg-2, Hsp70 and Hsp 90 are examples)
Diseases and Antigens—Vaccination Targets
a. Cancer: antigens and their sources
i. Tumor lysates extracted from biopsies
ii. Irradiated tumor cells
iii. Melanoma
1. MAGE series of antigens (MAGE-1 is an example)
2. MART-1/melana
3. Tyrosinase
4. ganglioside
5. gp100
6. GD-2
7. O-acetylated GD-3
8. GM-2
iv. Breast cancer
1. MUC-1
2. Sos1
3. Protein kinase C-binding protein
4. Reverse trascriptase protein
5. AKAP protein
6. VRK1
7. KIAA1735
8. T7-1, T11-3, T11-9
v. Other general and specific cancer antigens
1. *Homo Sapiens* telomerase ferment (hTRT)
2. Cytokeratin-19 (CYFRA21-1)
3. SQUAMOUS CELL CARCINOMA ANTIGEN 1 (SCCA-1), (PROTEIN T4-A)
4. SQUAMOUS CELL CARCINOMA ANTIGEN 2 (SCCA-2)
5. Ovarian carcinoma antigen CA125 (1A1-3B) (KIAA0049)
6. MUCIN 1 (TUMOR-ASSOCIATED MUCIN), (CARCINOMA-ASSOCIATED MUCIN), (POLYMORPHIC EPITHELIAL MUCIN), (PEM), (PEMT), (EPISIALIN), (TUMOR-ASSOCIATED EPITHELIAL MEMBRANE ANTIGEN), (EMA), (H23AG), (PEANUT-REACTIVE URINARY MUCIN), (PUM), (BREAST CARCINOMA-ASSOCIATED ANTIGEN DF3)
7. CTCL tumor antigen se1-1
8. CTCL tumor antigen se14-3
9. CTCL tumor antigen se20-4
10. CTCL tumor antigen se20-9
11. CTCL tumor antigen se33-1
12. CTCL tumor antigen se37-2
13. CTCL tumor antigen se57-1
14. CTCL tumor antigen se89-1
15. Prostate-specific membrane antigen
16. 5T4 oncofetal trophoblast glycoprotein
17. Orf73 Kaposi's sarcoma-associated herpesvirus
18. MAGE-C1 (cancer/testis antigen CT7)
19. MAGE-B1 ANTIGEN (MAGE-XP ANTIGEN) (DAM10)
20. MAGE-B2 ANTIGEN (DAM6)
21. MAGE-2 ANTIGEN
22. MAGE-4-a antigen
23. MAGE-4-b antigen
24. Colon cancer antigen NY-CO-45
25. Lung cancer antigen NY-LU-12 variant A
26. Cancer associated surface antigen
27. Adenocarcinoma antigen ART1
28. Paraneoplastic associated brain-testis-cancer antigen (onconeuronal antigen MA2; paraneoplastic neuronal antigen)
29. Neuro-oncological ventral antigen 2 (NOVA2)
30. Hepatocellular carcinoma antigen gene 520
31. TUMOR-ASSOCIATED ANTIGEN CO-029
32. Tumor-associated antigen MAGE-X2
33. Synovial sarcoma, X breakpoint 2
34. Squamous cell carcinoma antigen recognized by T cell
35. Serologically defined colon cancer antigen 1
36. Serologically defined breast cancer antigen NY-BR-15
37. Serologically defined breast cancer antigen NY-BR-16
38. Chromogranin A; parathyroid secretory protein 1
39. DUPAN-2
40. CA 19-9
41. CA 72-4
42. CA 195
43. Carcinoembryonic antigen (CEA)
b. AIDS (HIV associated antigens)
i. Gp120
ii. SIV229
iii. SIVE660
iv. SHIV89.6P
v. E92
vi. HCl
vii. OKM5
viii. FVIIIRAg
ix. HLA-DR (Ia) antigens
x. OKM1
xi. LFA-3
c. General infectious diseases and associated antigens
i. Tuberculosis
1. *Mycobacterium tuberculosis* antigen 5
2. *Mycobacterium tuberculosis* antigen 85
3. ESAT-6
4. CFP-10
5. Rv3871
6. GLU-S
ii. Malaria
1. CRA
2. RAP-2
3. MSP-2
4. AMA-1
iii. Possible mutant influenza and meningitis strains
d. Neuro protection—protect against neurological diseases (e.g., Alzheimer's, Parkinsons, Prion disease)
1. Classes of self CNS antigens
2. human alpha-synuclein (Parkinson's)
3. beta amyloid plaques (Alzheimer's)
e. Autoimmune Diseases (multiple sclerosis, Rheumatoid arthritis etc)
i. Disease linked MHC antigens
ii. Different classes of Self antigens
iii. Insulin
iv. Insulin peptide B9-23
v. glutamic acid
vi. decarboxylase 65 (GAD 65)
vii. HSP 60
Disease linked T-cell receptor (TCR)

EXAMPLES

Example 1: PLG Devices Loaded with GM-CSF

PLG matrices loaded with 3 µg of GM-CSF were implanted into the subcutaneous pockets of C57BL/6J mice.

Figure 11A:
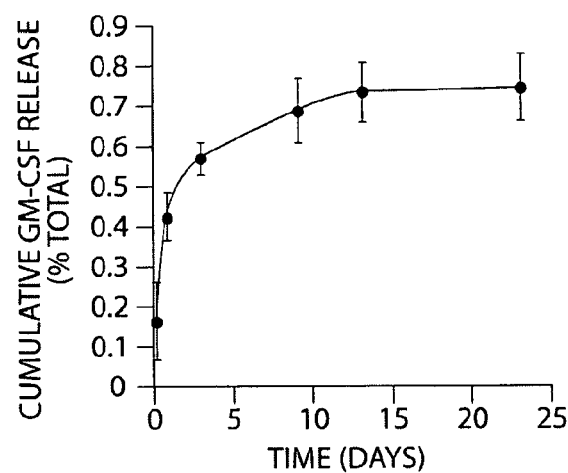
FIGS. 11A-F. In vivo control of DC recruitment and programming.

The macroporous PLG matrix presents GM-CSF, danger signals, and cancer antigens in a defined spatiotemporal manner in vivo, and serves as a residence for recruited DCs as they are programmed. These matrices released approximately 60% of their bioactive GM-CSF load within the first 5 days, followed by slow and sustained release of bioactive GM-CSF over the next 10 days (FIG. 11A) to effectively recruit resident DCs.

The matrices were made as follows. A 85:15, 120 kD copolymer of D,L-lactide and glycolide (PLG) (Alkermes, Cambridge, Mass.) was utilized in a gas-foaming process to form macroporous PLG matrices (Harris, L. D., Kim, B. S., and Mooney, D. J. Open pore biodegradable matrices formed with gas foaming. J. Biomed. Mater. Res. 42, 396-402 (1998)). GM-CSF was encapsulated (54% efficiency) into PLG scaffolds using a high pressure $CO_2$ foaming process. PLG microspheres encapsulating GM-CSF were made using standard double emulsion (Cohen S., Yoshioka T., Lucarelli, M., Hwang L. H., and Langer R. Controlled delivery systems for proteins based on poly (lactic/glycolic acid) microspheres. Pharm. Res. 8, 713-720 (1991)). To incorporate tumor lysates, biopsies of B16-F10 tumors that had grown subcutaneously in the backs of C57BL/6J mice (Jackson Laboratory, Bar Harbor Me.), were digested in collagenase (250 U/ml) (Worthington, Lakewood, N.J.), and subjected to 4 cycles of rapid freeze in liquid nitrogen and thaw (37° C.) and then centrifuged at 400 rpm for 10 min. The supernatant containing tumor lysates was collected and lyophilized with the PLG microspheres and the resulting mixture was used to make PLG scaffold-based cancer vaccines. To incorporate CpG-ODNs into PLG scaffolds, CpG-ODN 1826, 5'-tcc atg acg ttc ctg acg tt-3', (Invivogen, San Diego, Calif.) was first condensed with poly(ethylenimine) (PEI, Mw ~25,000 g mol-1, Sigma Aldrich) molecules by dropping ODN-1826 solutions into PEI solution, while vortexing the mixture. The charge ratio between PEI and CpG-ODN (NH3+:PO4−) was kept constant at 7 during condensation. PEI-CpG-ODN condensate solutions were then vortexed with 60 μl of 50% (wt/vol) sucrose solution, lyophilized and mixed with dry sucrose to a final weight of 150 mg. The sucrose containing condensates was then mixed with blank, GM-CSF and/or tumor lysate loaded PLG microspheres to make PLG cancer vaccines.

Figure 11B:
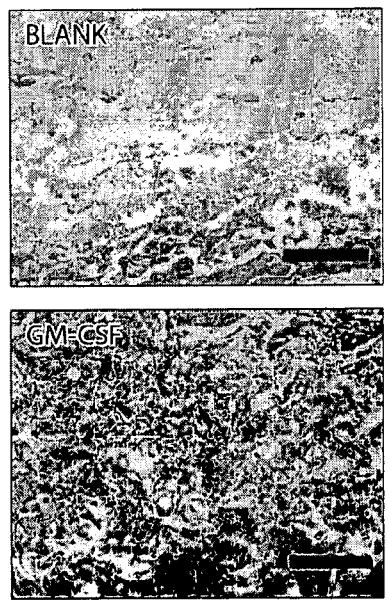
Figure 11C:
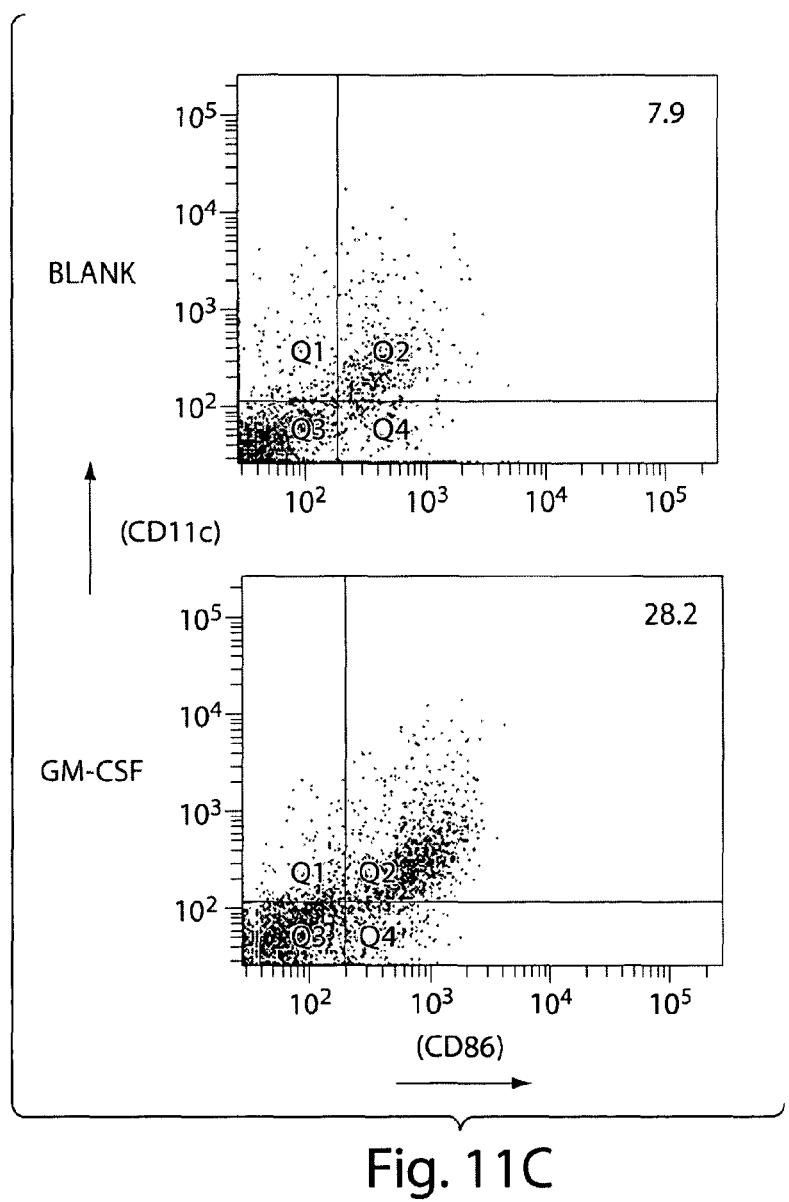
Figure 11D:
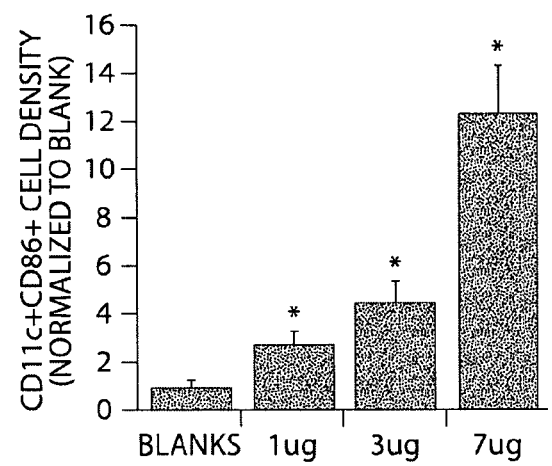

Following administration to the animals, histological analysis was carried out at day 14. The analysis revealed that the total cellular infiltration into scaffolds was significantly enhanced compared to control (no incorporated GM-CSF) (FIG. 11B). Analysis for DCs specifically (cells positive for cell surface antigens CD11c and CD86) showed that GM-CSF increased not just the total resident cell number, but also the percentage of cells that were DCs (FIG. 11C). The number of DCs residing in the material as a result of GM-CSF delivery was approximately the same or better than the number of DCs that are commonly programmed and administered by ex vivo protocols (~$10^6$ cells), and enhanced DC numbers were sustained in the material over time. The effects of GM-CSF on in vivo DC recruitment were time and dose-dependent (FIG. 11D).

Figure 11E:
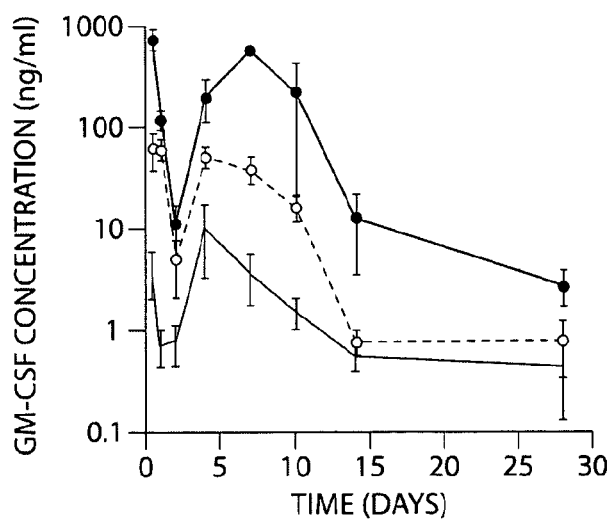

The dose of GM-CSF delivered from the PLG scaffolds was altered to provide distinct in vivo concentration profiles in the surrounding tissue, and regulate DC maturation and dispersion of resident DCs (FIG. 11E). Implantation of scaffolds with no GM-CSF led to moderate local levels immediately after implantation that subsequently fell to low levels by day 1-2, and then peaked again at day 5, likely due to the inflammatory response to the surgery and implanted PLG. Delivery of GM-CSF from the PLG scaffolds led to a similar GM-CSF concentration profile over time, but at much higher local concentrations. By approximately doubling the initial dose of GM-CSF, the system attained an order of magnitude difference in the peak levels of GM-CSF in vivo, likely due to endogenous GM-CSF production by resident DCs and leukocytes. The secondary peak for GM-CSF was found at day 5 for the 3000 ng dose, and at day 7 for the 7000 ng dose (FIG. 11E). Regardless of whether 3000 or 7000 ng doses of GM-CSF were utilized, the activation state of DCs peaked when GM-CSF levels began to subside (at days 10 and 28, respectively) and enter into the optimal concentration range for DC programming.

Figure 11F:
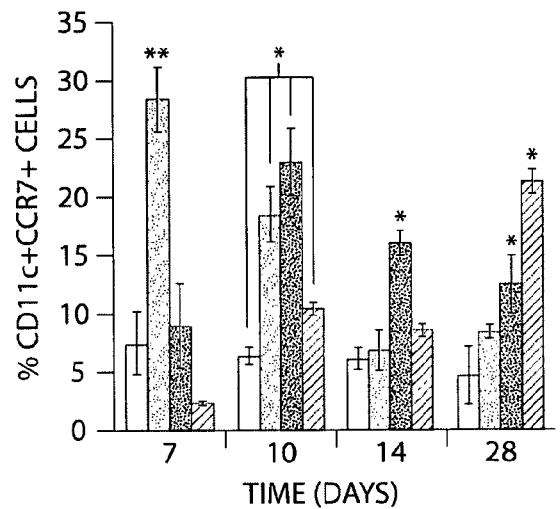

The ability of the pulse of GM-CSF to recruit and subsequently release a batch of activated DCs to home to the lymph nodes was then tested. Fluorescein isocyanate (FITC) was incorporated into and painted onto PLG scaffolds, as DCs recruited to the scaffold ingest this label. The label can be later used to identify these cells following their trafficking to the inguinal lymph nodes. At day 2, the 3000 ng dose of GM-CSF led to an inhibition of lymph node homing, likely due to the high initial levels of GM-CSF that entrap DCs at the scaffold site (FIG. 11F). However, as GM-CSF levels subsided, a batch of the recruited, FITC-positive DCs were released from the matrices, resulting in a superior and a sustained DC presence in the lymph nodes.

As temporally controlling the local GM-CSF concentration in turn controls recruitment, and dispersion of a batch of DCs, the utility of these cells as a cancer vaccine was evaluated by immobilizing melanoma tumor lysates into the matrices to load resident DCs with tumor antigens. These PLG cancer vaccines were implanted into C57BL/6J mice, and 14 days later these mice were injected with highly aggressive and metastatic B16-F10 melanoma cells. All mice implanted solely with blank PLG scaffolds had appreciable tumors within 18 days and had to be euthanized by day 23, due to the aggressiveness of these cells. Delivery of antigen alone from the PLG scaffolds slightly improved the fate of the mice, as some mice in this group survived until day 40. Surprisingly, co-delivery of GM-CSF with antigen dramatically decreased tumor formation, and the optimal GM-CSF dose delayed tumor formation by approximately 40 days in 50% of the animals, and cured 23% of animals. Moreover, localized tumor antigen presentation in combination with optimal GM-CSF exposure (400 ng) increased the average time before tumor formation by 3-fold as compared to antigen alone, and by nearly 2-fold over non-optimal GM-CSF exposure.

Analysis of T-cell infiltration into tumor tissue by immunohistochemistry was next performed to determine if programmed DCs were capable of inducing T-cell activation and homing to tumors. Vaccination with antigen alone resulted in CD4(+) T-cell infiltrates. Notably, recruiting and programming a batch of DCs in situ with appropriate GM-CSF presentation resulted in a 2-fold increase in CD8 (+) cytotoxic T-cell numbers over blank controls. The vaccine's efficacy was attenuated in CD8 and CD4 T-cell knock-out mice, attesting to the specific role of CD4 and CD8 T-cells in the immune protection.

A continuous process of in situ DC programming is achieved by presenting additional cues that released the DCs from GM-CSF inhibition once they reside in the matrices. In particular, the presentation of synthetic CpG-ODN with exogenous GM-CSF provides a mimic of bacterial infections, in which cells recruited by inflammatory cytokines are stimulated by local toll-like receptor activating "danger signals", such as CpG-ODN present in bacteria. CpG-ODN was immobilized to the PLG matrices by first condensing nucleotides with polyethylenimine (PEI) to form cationic nanoparticles. Following foaming of a combination of CpG-ODN and PLG particles, the CpG-ODN was largely retained in the matrices (>80% over 25 days) due to electrostatic interactions with the anionic PLG material. The CpG-ODN immobilization allows for host DCs, recruited by GM-CSF, to uptake these nucleotides locally as they reside in the matrices. Surprisingly, this approach resulted in approximately 2.5 and 4.5 fold increases in the numbers of activated DCs (positive for MHCII and CCR7) in the scaffolds, respectively, over GM-CSF or CpG-ODN delivery alone. CpG-ODN presentation enhanced DC activation in the presence of inhibitory GM-CSF levels (>40 ng/ml) in situ, indicating a more continuous process of DC recruitment and activation. This infection-mimicking system reliably generated activated DCs'. The magnitude of the immune response with this infection-mimic was confirmed grossly, as the lymph nodes of these animals were markedly enlarged. Most importantly, a 6-fold increase in the number of DCs that were first recruited to the matrices and subsequently dispersed to the lymph nodes was achieved with this system.

The ability of continuous DC recruitment, and programming to generate an immune response was next tested in the melanoma model. The vaccine provided significant protection, and the level of protection correlated with the CpG dose. Animal survival increased from 23% to 50% and finally 90% at CpG doses of 0 µg, 10 µg and 100 µg, respectively. This material infection-mimic induced equivalent or better immune protection than that obtained with existing cell-based therapy. Materials presenting CpG-ODN with lysates alone had only a 20% survival, indicating the benefit of recruiting DCs with GM-CSF. The benefit of providing a residence for recruited DCs while they are programmed was demonstrated by the failure of vaccine formulations consisting of bolus injections of tumor lysates, CpG-ODN, with and without 3000 ng of GM-CSF. Moreover, injecting GM-CSF loaded PLG microspheres to provide sustained GM-CSF delivery without providing a residence for recruited cells, with bolus CpG-ODN and tumor lysate delivery resulted in little immune protection and animals did not survive over 35 days.

To further examine the mechanism of immune protection with this material system, the subsets of DCs and the endogenous production of cytokines by these cells in materials presenting GM-CSF and CpG-ODN alone or together were analyzed, along with the specificity of the immune response. The delivery of GM-CSF alone enhanced the recruitment of CD11c(+)CD11b(+) myeloid DCs, whereas CpG-ODN delivery alone had little effect on the overall numbers of this subset. CpG-ODN delivery did, though, increase the number of plasmacytoid DCs at the site, which have been described to predominantly secrete Thelper(Th)-1 cytokines, especially type 1 interferons and interleukin(IL)-12 that can promote CD8(+), cytotoxic T cell immunity in response to CpG-ODN presentation with antigen. Accordingly, CpG signaling not only upregulated the expression of activation markers on resident DCs, but also induced IFN-γ and IL-12 production at the vaccine site, as expected from the increased presence of plasmacytoid DCs. Moreover, analysis of T cell infiltrates into tumors that formed in the subset of animals that were not completely protected (infection mimics; 10 µg CpG-ODN dose) revealed that, even in these animals, DC programming with CpG-ODN resulted in an almost 3-fold increase in CD8(+) T-cell infiltration over controls. Further, tyrosinase-related protein (TRP)-2 is a main antigenic target of the immune response elicited by melanoma vaccines in both mice (including B16 whole cell vaccines) and humans, and staining cells isolated from spleens with MHC class I/TRP2 peptide pentamers revealed a dramatic expansion of TRP2-specific CD8 T cells in vaccinated mice. These antigen-specific T cells are involved in the killing of tumor cells, and facilitated immune protection after vaccination. Additionally, 33% of surviving mice developed patches of skin and hair depigmentation starting at the sites of tumor inoculation (back of neck). Depigmentation, which likely involves T cell responses to melanocyte antigens, has been correlated to improved clinical responses in human melanoma patients, and, in these studies, was only observed in mice treated with infection mimics.

These results indicate that mimicking aspects of infection with polymeric material systems dramatically impacts tumor progression by effectively recruiting, activating and homing DCs to lymph nodes. The first approach utilized a pulse of GM-CSF alone to recruit DCs to the tumor-antigen presenting material. The DCs subsequently resided within the material and were trapped until GM-CSF levels fell and cells could become activated and disperse. The specific concentration and duration of GM-CSF are critical to its effects. A continuous process was subsequently developed to shuttle DCs through an infectious-like microenvironment via recruitment with GM-CSF, followed by activation of resident DCs via CpG-ODN presentation, and subsequent release. The presentation of PEI condensed CpG-ODN from the material dramatically increased not only the numbers of activated, host DCs residing in the material, but also the percentage and total numbers of programmed DCs that emigrated to the lymph nodes. Further, CpG-ODN signaling selected for specific DC subsets and DC functions associated with protective immune responses.

The system's quantitative control over DC trafficking and activation translated to a regulation over the efficacy of the cancer vaccine. As the numbers of DCs that were programmed and dispersed to the lymph nodes increased, the survival increased from 0 to 25 and finally 90%. T-cells mediated immune protection, as a clear relation between the numbers of T cells in the tumors that did form and vaccine efficacy was found, and infection mimics induced the generation of melanoma-antigen specific T cells. The matrix structure was necessary to produce long-lasting immunity, as vaccines delivered in bolus form and sustained release without provision of a cell residence failed to produce significant protective immunity. Although reports concluded that either cell transplantation or multiple systemic injections are necessary to promote protective immunity in clinically relevant tumor models, the data indicate that devices comprising functional polymeric residence materials provide significant and specific immune protection that is equal to or superior to previous systems, even with single application at vastly reduced total drug doses (e.g., 3 µg in the scaffold system vs. 100's µg total dose in repeated, systemic injections).

These data have significant clinical relevance, as the material system programmed DCs in situ, and not only bypassed the complication and cost of ex vivo cell manipulation and transplantation, but also provided tight control over the number of DCs recruited, activated and dispersed to the lymph nodes. Patients are treated with and the devices provide an alternative to current cancer vaccines, or are used in concert with those and other approaches.

The system is applicable to other situations in which one desires to promote a destructive immune response (e.g., eradicate infectious diseases) or to promote tolerance (e.g., subvert autoimmune disease). The use of polymers as a temporary residence for in situ cell programming is a powerful alternative to current cell therapies that depend on ex vivo cell manipulation (e.g., stem cell therapies).

Figure 2A:
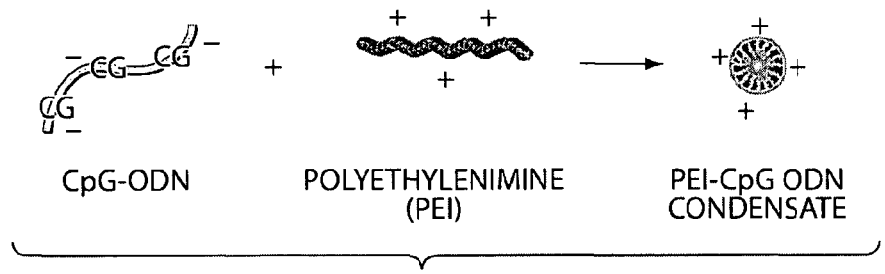
FIGS. 2A-C.
Figure 2B:
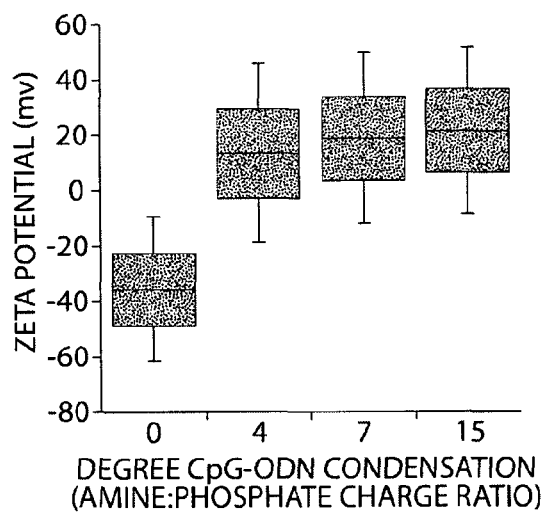
Figure 2C:
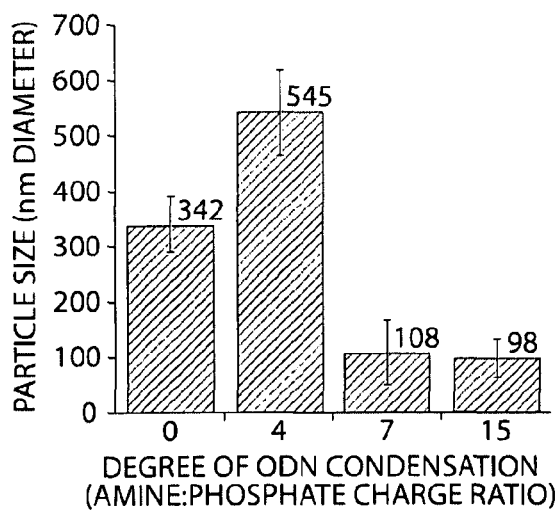

Example 2: Condensation of Synthetic CpG-ODN Molecules Increases Cellular Uptake Synthetic CpG-ODN molecules were condensed with PEI, which resulted in positively charged, small PEI-CpG-ODN condensates that facilitates cellular internalization via promoting association with the cell membrane and enhancing transmembrane transport (FIG. 2). ODN Condensation at charge ratios of 7 and 15, between the amine groups of PEI and the phosphate groups of ODNs, resulted in optimal particle sizes and positive charge (FIGS. 2B and C), but a charge ratio of 7 was utilized in experiments due to PEI toxicity at high doses.

Figure 3A:
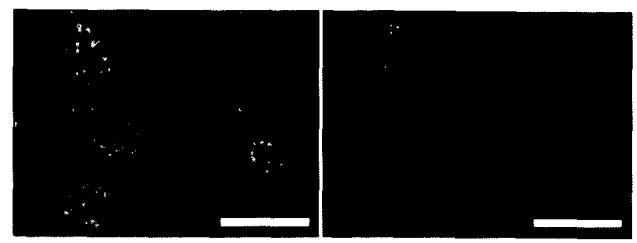
FIGS. 3A-D. FIGS. A-C show in vitro uptake of CpG-ODN by JAWSII DCs.
Figure 3B:
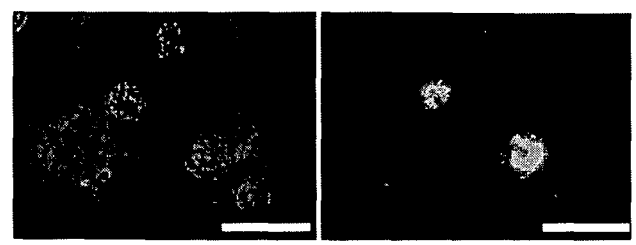
Figure 3C:
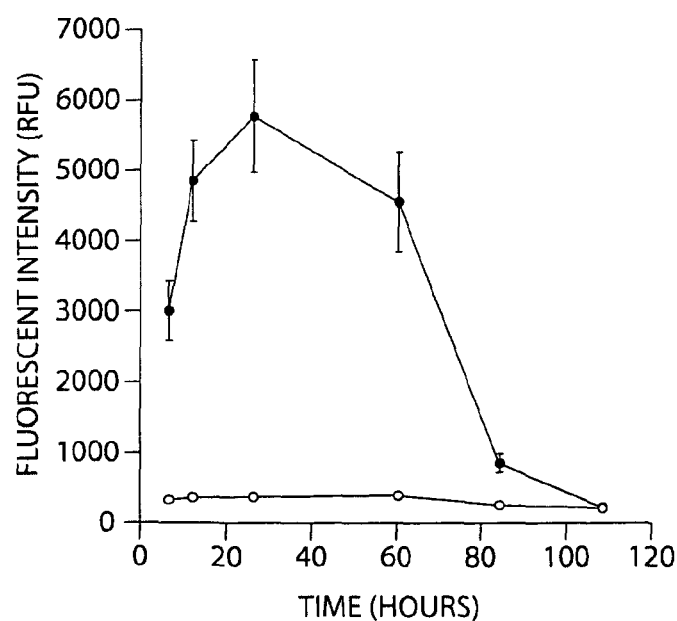
Figure 3D:
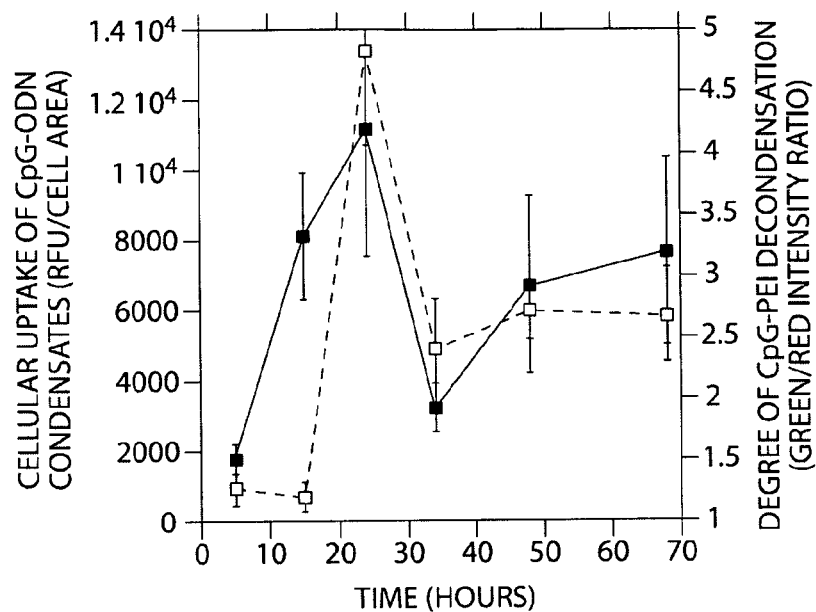

PEI condensation of CpG-ODN dramatically enhanced nucleotide uptake into DCs in vitro (FIG. 3A-C). Quantification of CpG-ODN uptake into DCs revealed orders of magnitude differences (up to ~100-fold) between ODN condensates and naked ODN, which were maintained for extended time periods (>80 hrs) in vitro (FIG. 3C). The complexes subsequently decondense (FIG. 3D) allowing for CpG-ODN localization to its intercellular receptor, TLR-9, which has been previously demonstrated to be present in endosomes.

Example 3: CpG-ODN Induced DC Activation and DC Mobilization

Figure 4A:
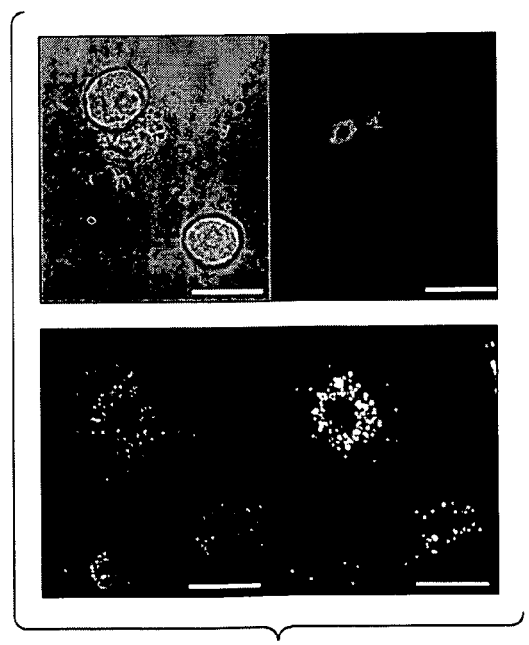
FIGS. 4A-D. (A) Imaging DC activation.
Figure 4B:
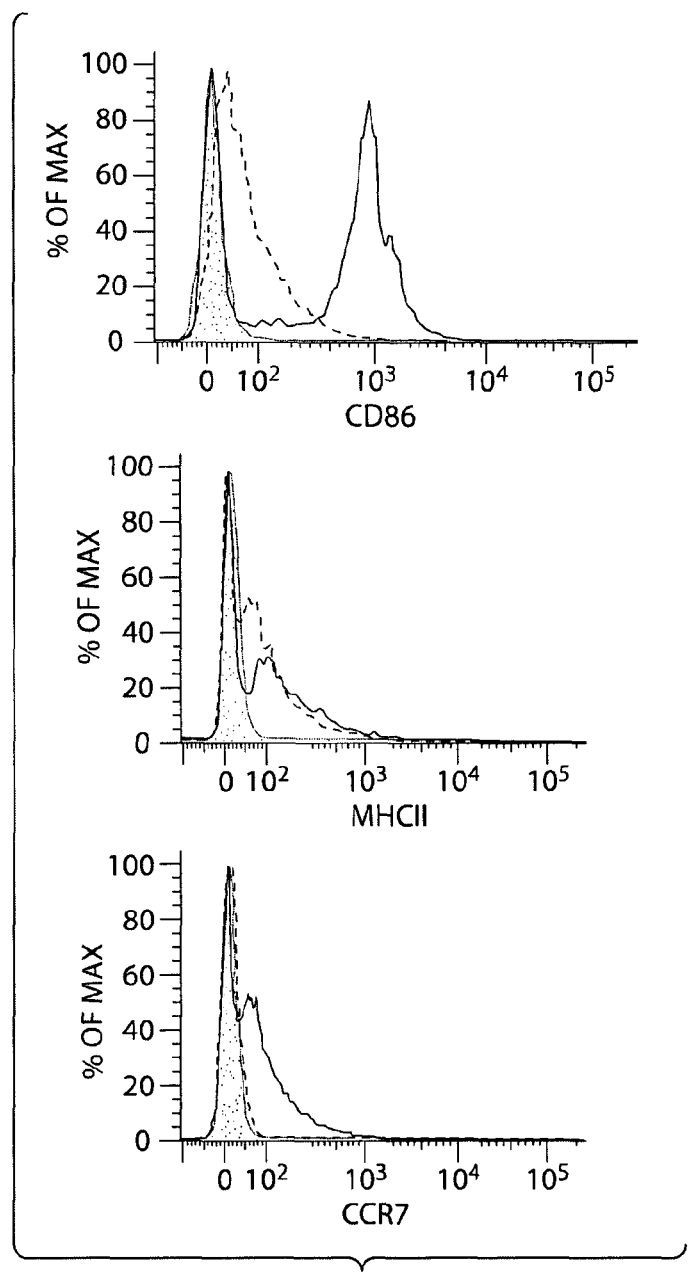
Figures 4C, 4D:
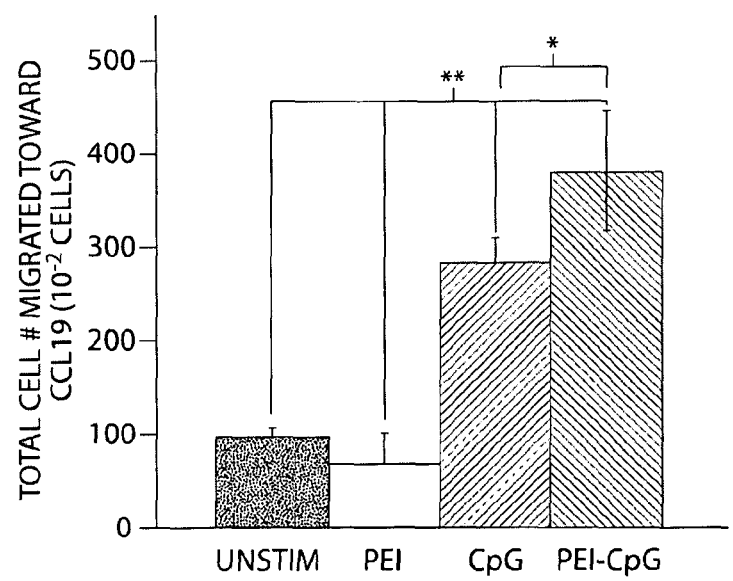

Because effective CpG stimulation of DCs requires intercellular localization, the effects of PEI-condensation were evaluated on DC activation. DCs stimulated with PEI-CpG-ODN in vitro exhibited enhanced levels of CD86, MHCII and CCR7 expression, in comparison to those stimulated with naked CpG-ODN, which correlated strongly with DC uptake of condensates (FIGS. 4A and B). DCs exhibited an activated morphology, upon cellular uptake of PEI-CpG-ODN including the development of fine needle-like dendrites and large membrane expansion, which allows mature DCs to "wrap-up" T-cells promoting strong cell-cell interactions. The activation states of PEI-CpG-ODN stimulated DCs mirrored or surpassed that of positive controls stimulated with TNF-α and LPS (FIG. 3C) and PEI-CpG-ODN condensates promoted a 3-fold increase in DC migration toward CCL19 in vitro, over unstimulated DCs (FIG. 4D).

Figure 5A:
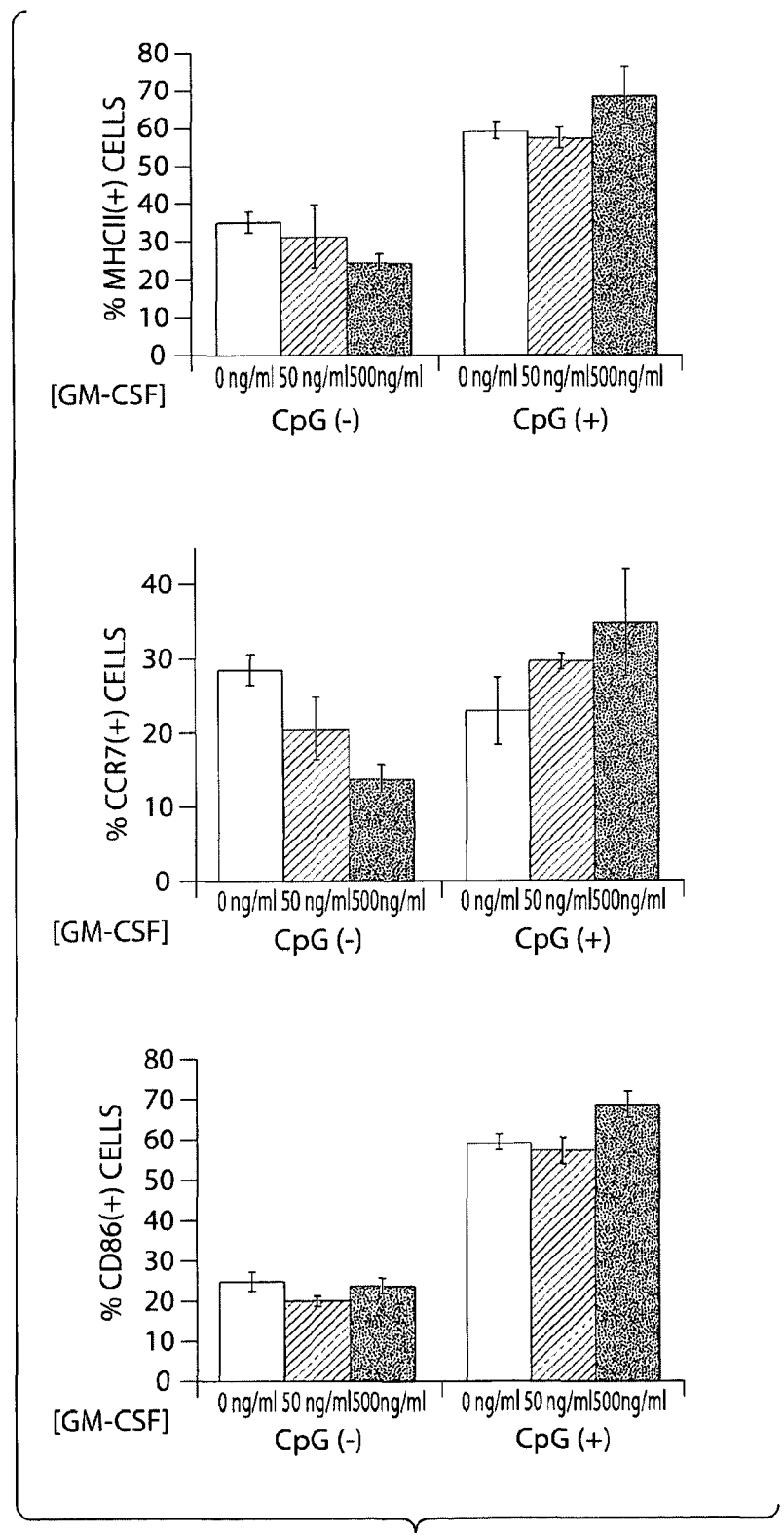
FIGS. 5A-B.
Figure 5B:
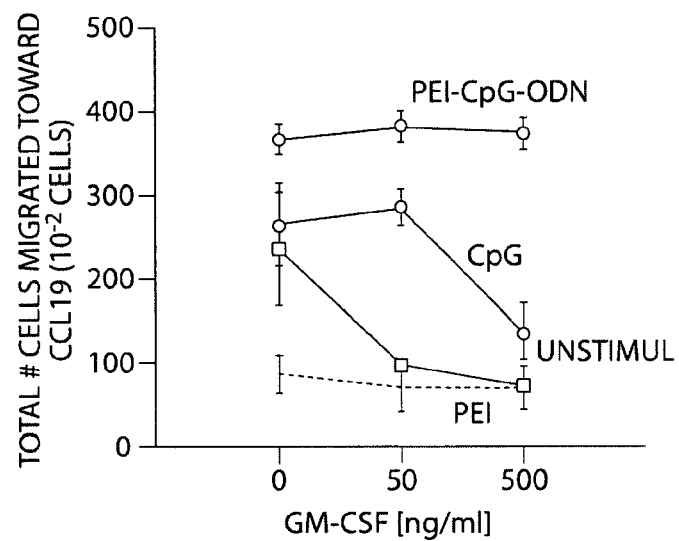

PEI-CpG-ODN condensates also released DCs from GM-CSF inhibition, as significant DC activation was noted in cells exposed to both condensed oligonucleotides and high levels of GM-CSF (FIG. 5A). Additionally, PEI-CpG-ODN stimulation also promoted DC migration away from high GM-CSF sources (500 ng/ml) toward CCL19 (FIG. 5B).

Figure 6A:
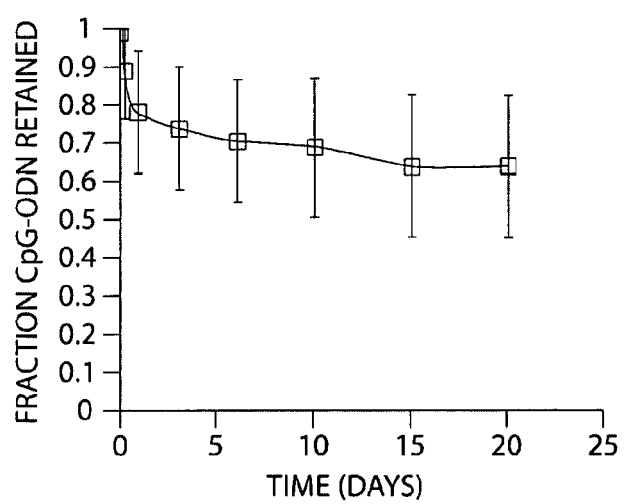
FIGS. 6A-C.
Figure 6B:
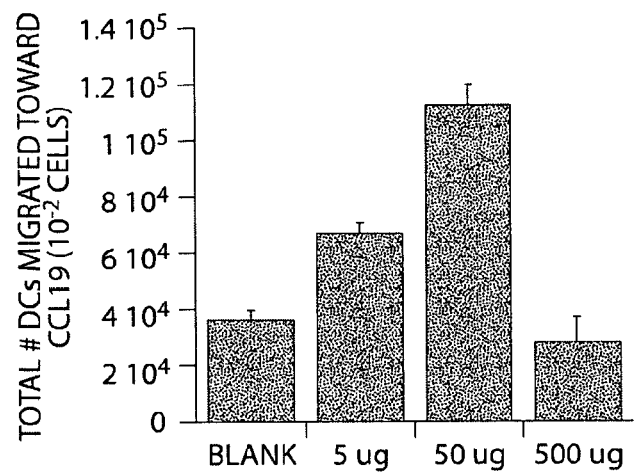
Figure 6C:
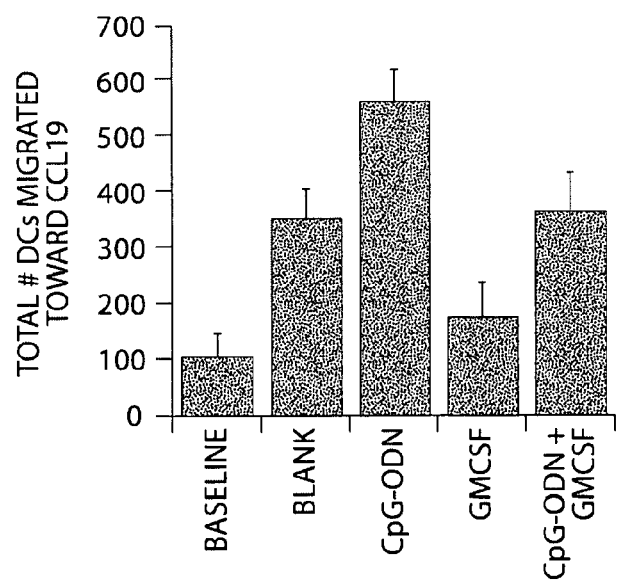

A PLG system was developed that effectively immobilized and presented PEI-CpG-ODN condensates (FIG. 6A) to resident DCs to stimulate DC activation and mobilization. Local PEI-CpG-ODN presentation promoted DC mobilization in vitro (FIG. 6). Interestingly, there is an optimal dose range, 5-50 µg, of PEI-CpG-ODN that enhanced DC emigration from PLG matrices toward CCL19, but high doses (500 µg) had no effect on DC migration (FIGS. 6B and C). A 25 µg of PEI-CpG-ODN also counteracted the suppressive effects that high GM-CSF levels had on DC migration, in this model (FIG. 6C). These results indicate that appropriate CpG-ODN presentation provides an avenue to continuously program and disperse host DCs that are recruited and otherwise trapped by high levels of GM-CSF in situ.

Example 4: Infection-Mimics Continuously Program and Disperse DCs In Vivo

An infection-mimicking system to continuously recruit and program DCs was created by simultaneous release of GM-CSF to attract host DCs to PLG matrices, while the PEI-CpG-ODN condensates were largely retained in the matrix (>80% over 25 days) (FIG. 6), likely via electrostatic interactions as has been shown for plasmid DNA, allowing for recruited DCs to uptake the complexes locally. Strikingly, when optimized, this approach resulted in approximately 2.5 and 4.5 fold increases in the numbers of MHCII and CCR7 expressing DCs resident in the matrices in situ, respectively (over GM-CSF or CpG-ODN delivery alone) (FIGS. 7A and B). Interestingly, high doses of PEI-CpG-ODN (>50 µg) resulted in relatively low MHCII expression and enhanced CCR7 expression, indicating differential regulation of DC function in comparison to low doses (FIG. 7A). Optimum CpG-ODN signaling (~10-25 µg) enhanced DC activation in the presence of inhibitory GM-CSF levels (>40 ng/ml) in situ, and this infection-mimicking system generated the numbers of activated DCs ($>10^6$) (FIGS. 7A and B) commonly administered in ex vivo protocols.

Most importantly, a 6-fold increase in the number of DCs that were first recruited to the matrices and subsequently dispersed to the lymph nodes was achieved with this system (FIG. 8 A). The magnitude of the immune response with infection-mimics could even be appreciated grossly, as the lymph nodes of these animals were markedly enlarged (FIGS. 8B and C). As characterized by infectious responses, these swollen lymph nodes contained greater numbers of immune cells including DCs (FIGS. 8C and D).

Figure 9:
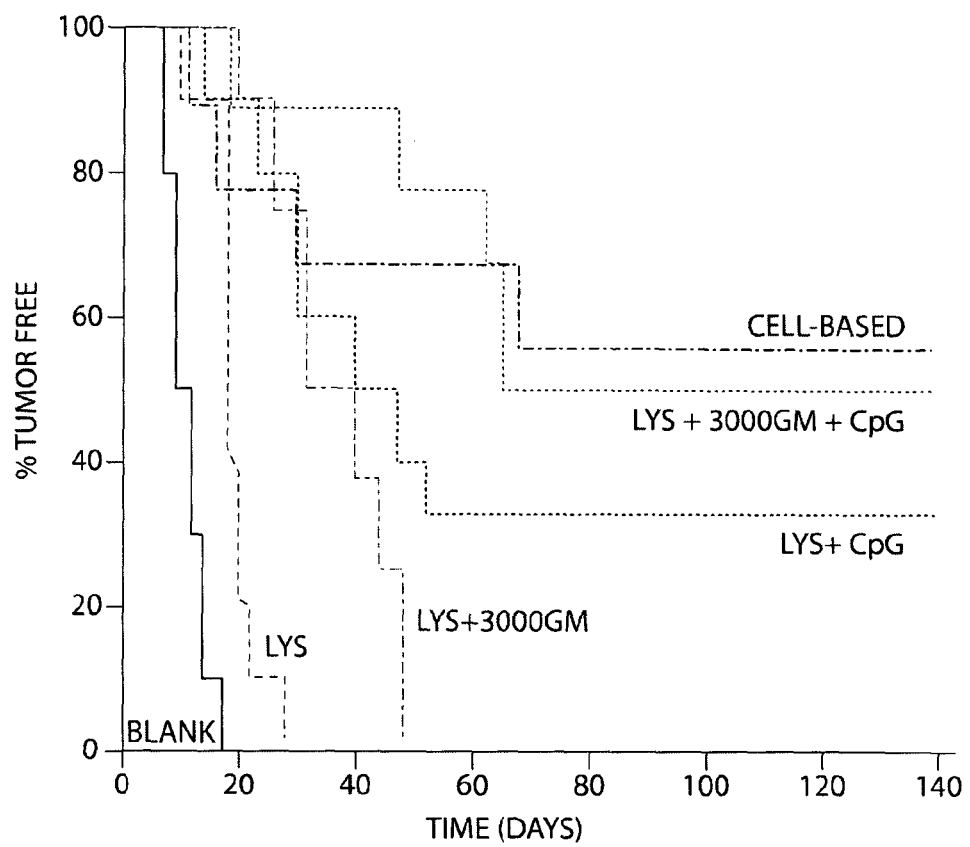
FIG. 9 is a bar graph showing infection-mimicking microenvironment confers potent anti-tumor immunity. The time to tumor occurrence after PLG cancer vaccines were implanted into mice. A comparison between blank PLG scaffolds (Blank), scaffolds loaded with antigen alone (Lys), antigen+3000 ng GM-CSF (Lys+3000 ng GMCSF), antigen+PEI-CpG-ODN condensate (Lys+CpG) and the combination of antigen, 3000 ng GM-CSF and PEI-CpG-ODN (Lys+3000 ng+PEI-CpG-ODN). Animals were also immunized using a cell-based vaccine (cell-based) using irradiated B16-F10 melanoma cells that had been genetically modified to produce GM-CSF, for comparison. At Day 14 after vaccination, C57BL/6J mice were challenged with $10^5$ B16-F10 melanoma tumor cells and monitored for the onset of tumor occurrence (n=9 or 10).

Example 5: Infection-Mimicking Microenvironment Confers Potent Anti-Tumor Immunity The ability of continuous DC recruitment, and programming to generate an immune response was next tested in the melanoma model. This vaccine provided significant protection, as 50% of the animals did not form tumors over an 80 day time frame (FIG. 9), and this result was remarkably similar to that obtained with a widely investigated cell-based therapy (FIG. 9). Animals receiving lys+CpG were 37.5% tumor free 140 days after treatment and achieved protective immunity.

Figure 10A:
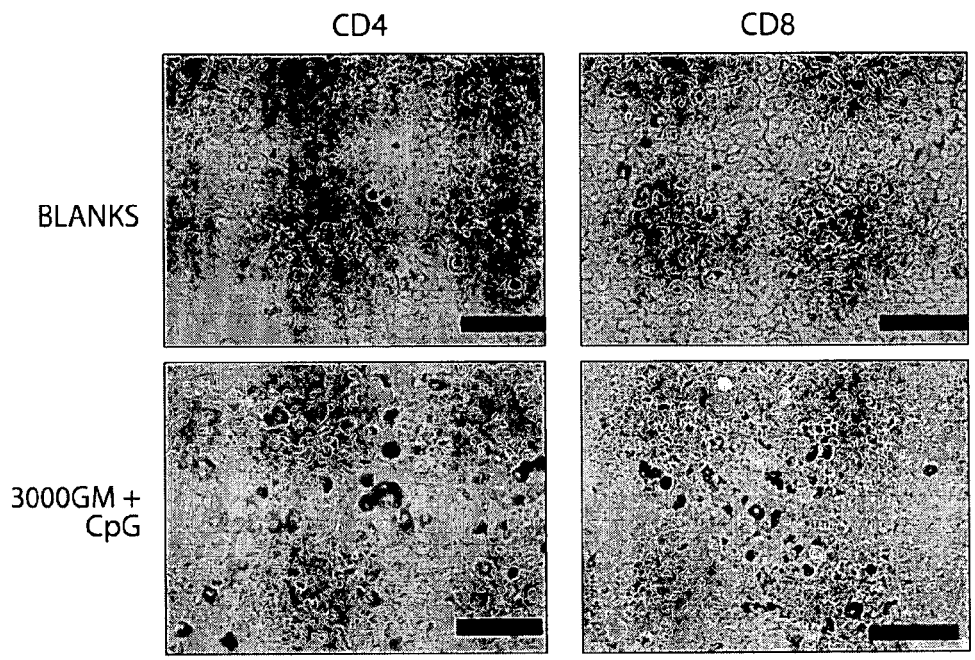
FIGS. 10A-B. Vaccination efficacy of Infection mimics dependent on T cell responses.
Figure 10B:
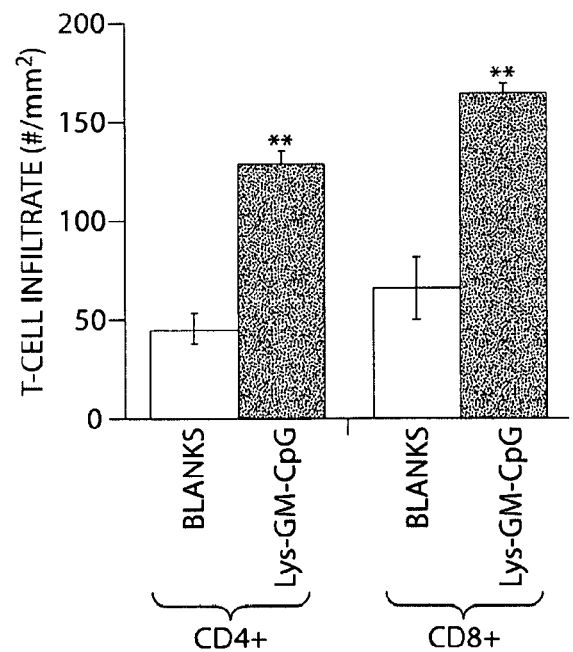

Furthermore, analysis of T-cell infiltrates into tissue of tumors that formed in the subset of animals that were not completely protected revealed that, even in these animals, DC programming with CpG-ODN resulted in an almost 3-fold increase in CD8(+) T-cell infiltration over controls (FIG. 10). Thus, all animals receiving the Lys-GM-CpG treatment demonstrated a therapeutic benefit.

Example 6: Tumor Protection is Regulated by CpG-ODN Presentation and Plasmacytoid DC (pDC) Enrichment Hematopoetic precursor cells of both the myeloid and lymphoid lineage have the capacity to differentiate into two main categories of DCs, plasmacytoid DCs (pDCs) and conventional DCs (cDCs), each of which are equipped with specific defense mechanisms capable of propagating specific responses to invading pathogens. This plasticity likely allows for the recruitment and generation of the DC subset(s) most proficient at eliciting the desired immune response. cDCs include $CD11c^+CD11b^+$ and $CD11c^+CD8\alpha^+$ cells exhibiting classical DC morphology with the long, protruding dendrites that make them especially adept at antigen processing and antigen presentation to T cells. pDCs are round non-dendritic cell capable of producing large amounts of type-1 interferons in response to 'danger signals', such as unmethylated CpG dinucleotide sequences in bacterial or viral DNA.

pDC derived type 1 interferons (IFN) link innate and adaptive immunity to viral infection by triggering antigen cross presentation to CD8+ T cells and interleukin production (e.g. IL-12) by cDCs that facilitate the clonal expansion of cytotoxic T cells. Type 1 IFNs also act to directly induce naïve T cell differentiation to T helper 1 cells. In addition to producing potent IFNs, pDCs stimulated by inflammatory stimuli and microbial infection differentiate into a dendritic form capable of processing and presenting antigen to prime T cell responses. pDCs and cDCs cooperate to perform specialized functions that initiate distinct cellular and molecular events leading to protective immunity.

Many cell-based vaccines for cancer fail to incorporate the different components of the DC network. Cancer vaccines are frequently developed using easily accessible, patient-derived blood monocytes that are transformed into DCs ex vivo using cytokine mixtures and pulsed with tumor antigens to promote antigen presentation. These antigen-loaded DCs are then injected back into cancer patients with the goal of inducing anti-tumor immune responses mediated primarily by Th1 cells and CTLs. While initial trials utilizing ex vivo DC vaccines in advanced cancer patients have resulted in antigen-specific T-cell expansion and the production of protective cytokines, many vaccines have failed to show survival advantage over traditional treatments (e.g., chemotherapy) and have failed to gain FDA approval. These cell-based vaccines provide no control over the in vivo function of the transplanted DCs and only incorporates one DC type into the vaccine, which may not be the most potent. Therefore, the rate-limiting step is likely the inability to fully recapitulate ex vivo the development of immunocompetent DCs, in particular the processes of DC activation and specialization during the generation of immune responses. The devices and methods described herein overcome the shortcomings of such earlier approaches, and therefore, haver several advantages over earlier systems.

The devices comprise an implantable, synthetic extra-cellular matrix (ECM) that controls the in situ recruitment and generation of a heterogenous DC network to produce protective immune responses to tumors. GM-CSF was incorporated into polylactide-co-glycolide (an FDA approved biomaterial) matrices to recruit DC precursors and DCs, as the cytokine is released from the material into the surrounding tissue. These macroporous matrices present immobilized tumor antigens and CpG-rich oligonucleotides as danger signals, capable of programming DC development and maturation as cells reside within the material. The distribution of the DC subsets generated at the vaccine site is regulated by modifying cancer-antigen presentation by the material and the dosages of danger signals, which significantly affected the magnitude of the protective immune response to tumors when tested in an art recognized B16-F10 tumor model.

Matrices were made to release a pulse of GM-CSF to recruit DCs, and were loaded with 0, 3000, and 7000 ng of GM-CSF, and implanted into the subcutaneous pockets of C57BL/6J mice. A GM-CSF gradient formed in the surrounding tissue, which peaked at 12 hours post-implantation as the GM-CSF concentration reached 100 μg/ml and 30 μg/ml (>30 fold difference over no incorporated GM-CSF) at distances of 1-3 mm and 3-5 mm, respectively, from the implant site. Elevated GM-CSF levels were maintained for extended periods (approximately 10 days) while the factor was released from the PLG to the neighboring tissue. Histological analysis at day 14 post-implantation of PLG matrices loaded with 3000 ng of GM-CSF revealed enhanced cellular infiltration over blank controls, and FACS analysis for the CD11c(+) DC population showed that GM-CSF delivery recruited significantly more DCs (~8 fold increase) than blank controls. The total number of DCs recruited and their expression of the co-stimulatory molecule CD86 increased with GM-CSF delivery in a dose dependent manner.

PLG matrices were then modified to immobilize TLR-activating, PEI-condensed CpG-ODN molecules and present them as danger signals to DC populations recruited by GM-CSF. Provision of condensed CpG-ODN signaling with GM-CSF dramatically enhanced cellular infiltration into PLG matrices, as revealed by histological analysis at Day 10 post-implantation. Importantly, CpG-ODN presentation from PLG matrices regulated the local presence of specific DC subsets and the resulting production of protective cytokines. Stimulation of the DC infiltrate recruited by GM-CSF with CpG-ODN enriched the PLG matrix with CD11c(+) PDCA-1(+) plasmacytoid DCs (pDCs), a DC subset exhibiting enhanced type 1 IFN production that are associated with t-helper 1 (Th1) immunity.

CpG-ODN leads to preferential recruitment and expansion of pDCs to the tumor site. The dose of CpG-ODN is controlled to regulate the numbers of resident pDCs, which increased from 190,000, to 520,000, to 1,100,000 cells at doses of 0, 10 and 100 μg of CpG-ODN, respectively. GM-CSF delivery alone significantly enhanced the numbers of CD11c(+)CD11b(+) cDCs recruited to the matrices, but co-presentation of CpG-ODN had little effect on either mDC populations or Cd11c(+)CD8(+) DCs. High doses of CpG-ODN promoted the local production of IFN-α (~1010 pg/ml), IFN-γ (~600 pg/ml) and, to a lesser degree, IL-12 (150 pg/ml) at the implant site, which correlated with the increased pDC numbers at this condition. The recruitment of DCs by GM-CSF was required for CpG-ODN signaling to have a significant effect, in terms of expansion of pDC populations and production of Th1 cytokines. These results indicate that controlled GM-CSF and CpG-ODN danger signaling from synthetic extra-cellular matrices can effectively regulate resident pDC and CD11c(+)CD11b(+) cDC numbers along with the production of Th1 cytokines.

Figure 12A:
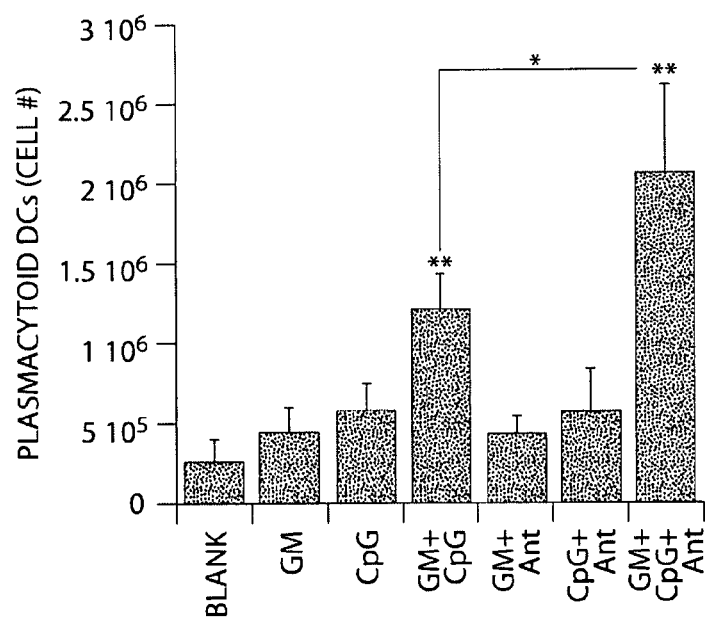
FIGS. 12 A-G. Antigen co-presentation with CpG-ODN to DCs infiltrating PLG matrices enhances local CD8+ cDC numbers, IL-12 production and total CD8(+) cell numbers. The number of (FIG. 12A) plasmacytoid DCs, (B) CD11c (+)CD11b(+) cDCs, and (FIG. 12C) CD11c(+)CD8(+) cDCs at day 10 post-implantation in blank matrices (Blanks) and in response, to doses of 3000 ng GM-CSF (GM) or 100 µg CpG-ODN (CpG) alone or in combination (CpG+GM) or co-presented with tumor lysates (GM+Ant, CpG+Ant and CpG+GM+Ant). The in vivo concentration of (FIG. 12D) IFN-αc (E) IFN-γ and (FIG. 12F) IL-12 at day 10 post-implantation in blank matrices (Blanks) and in response to doses of 3000 ng GM-CSF (GM) or 100 µg CpG-ODN (CpG) alone or in combination (CpG+GM) or co-presented with tumor lysates (GM+Ant, CpG+Ant and CpG+GM+Ant).
(FIG. 12G). FACS histograms of CD8(+) cells infiltrating Blank PLG matrices (-) and matrices loaded with 3000 ng GM-CSF and 100 µg CpG-ODN alone (- - -) or with tumor antigens (tinted line). Values in A-F represent mean and standard deviation (n=4 or 5). * P<0.05 ** P<0.01.
Figure 12B:
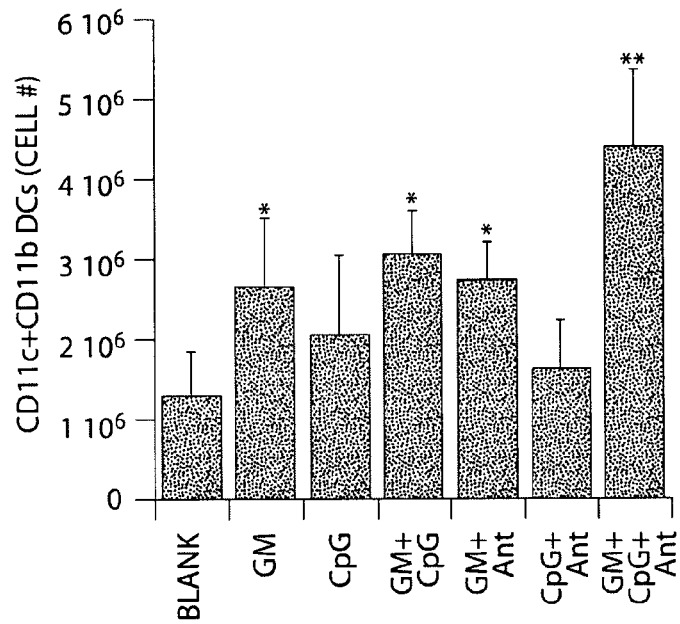
Figure 12C:
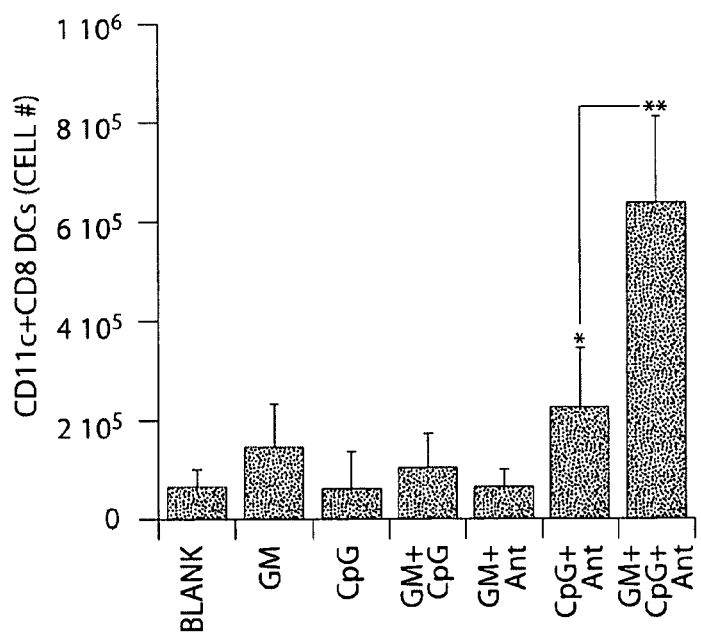
Figure 12D:
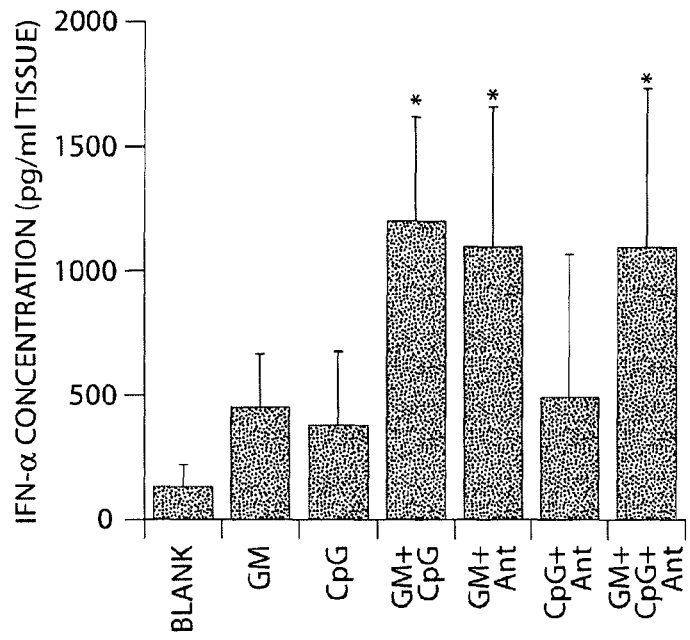
Figure 12E:
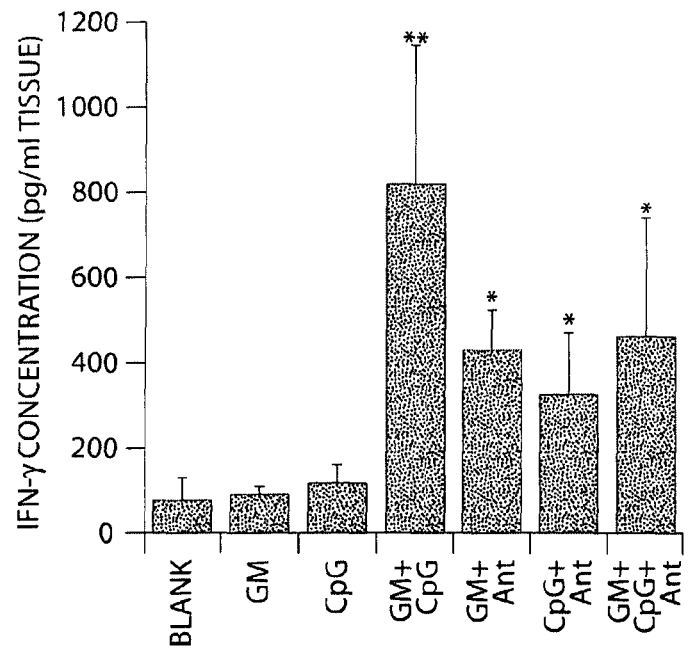
Figure 12F:
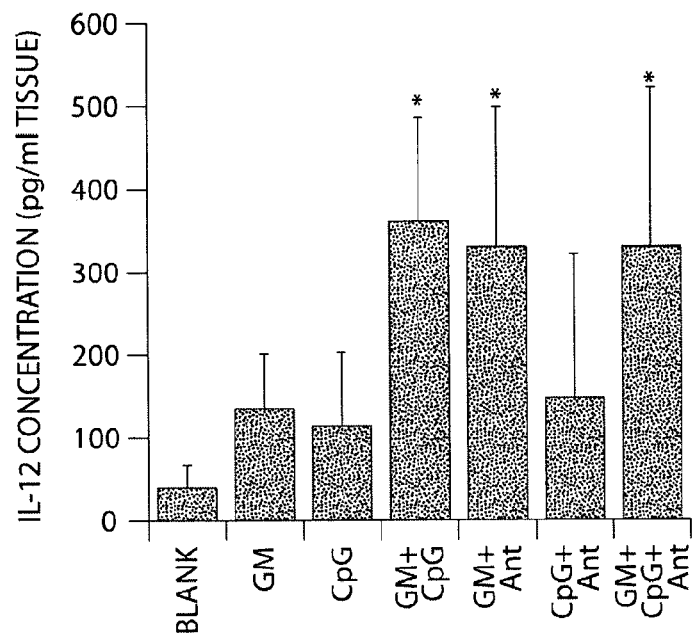
Figure 12G:
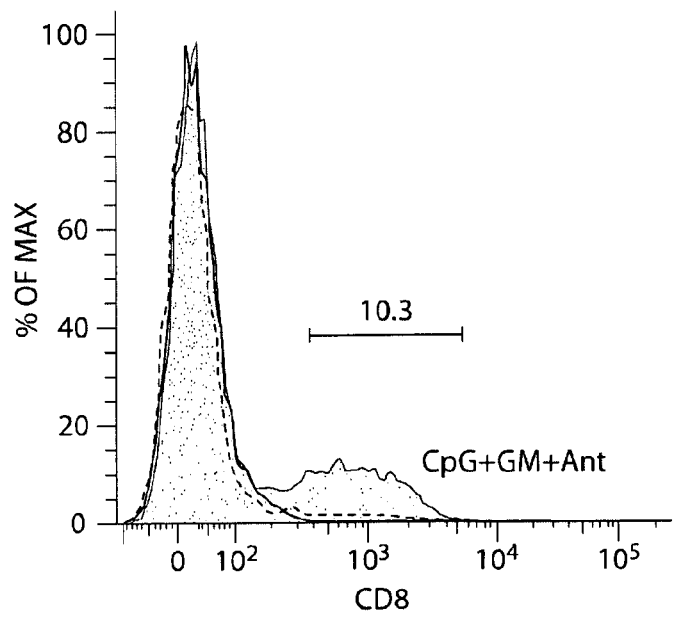

Studies were carried out to determine whether co-presenting cancer antigens with CpG-ODNs to matrix-resident DCs would promote further DC development, activation and antigen sensitization, leading to protective tumor immunity and cytotoxic T cell responses. Antigen-presenting matrices were fabricated by encapsulating B16-F10 melanoma tumor lysates into the PLG matrices. Controlled antigen presentation in combination with GM-CSF and CpG signaling enhanced the numbers of resident pDCs at Day 10 post-implantation by 2-fold over matrices without antigen, and by 10-fold over blank controls (FIG. 12A). No significant difference in pDC numbers was observed with antigen presentation in combination with GM-CSF or CpG signaling alone, indicating the benefit of both GM-CSF-mediated recruitment and CpG-ODN activation of matrix-resident DCs. The CD11c(+)CD11b(+) DC population at the vaccine site depended on GM-CSF delivery alone (FIG. 12B), as antigen or CpG signaling alone or in combination had no significant effect on the recruitment and expansion of these cDCs (FIG. 12B). Antigen and CpG-ODN presenting matrices led to the presence of 200,000 CD11c(+)CD8(+) cDCs, which increased to approximately 670,000 (9-fold increase over blank matrices) with GM-CSF-mediated recruitment (FIG. 12C). Analysis of the endogenous production of IFNs and IL-12 revealed that antigen stimulation in combination with GM-CSF promoted endogenous IFN-α and IFN-γ production that was similar to CpG-ODN induction (FIG. 12D-E). Additionally, the in situ production of the T-cell growth factor, IL-12, at matrices presenting both antigen and CpG-ODN to cell populations recruited by GM-CSF was approximately 4-fold higher than blank matrices at least 2-fold higher all other matrix formulations (FIG. 3F). Remarkably, a significant percentage (10.3%) of the total cells at the site of antigen presenting matrices were CD8(+) (cDC subset and cytotoxic T-cells) (FIG. 12G), which was in correlation with both the number of CD11c(+)CD8(+) cDCs and the concentration of IL-12 (FIGS. 12C, F,G). These results indicate that immune responses sensitive to cancer antigen presentation were generated by manipulating both the number and function of specific DC subsets in situ, including CD8(+)DCs, which was accompanied by CD8+ T cell activity.

Figure 13A:
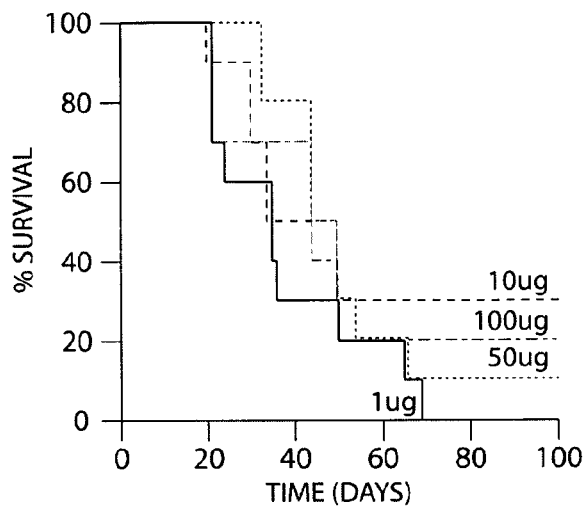
FIGS. 13A-F. Tumor protection regulated by CpG-ODN presentation and plasmacytoid DC enrichment. Survival times of mice vaccinated with PLG vaccines 14 days prior to B16-F10 melanoma tumor challenge.
Figure 13B:
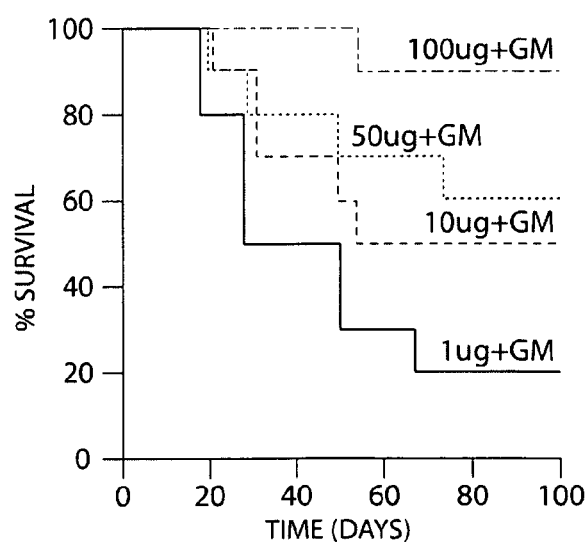
Figure 13C:
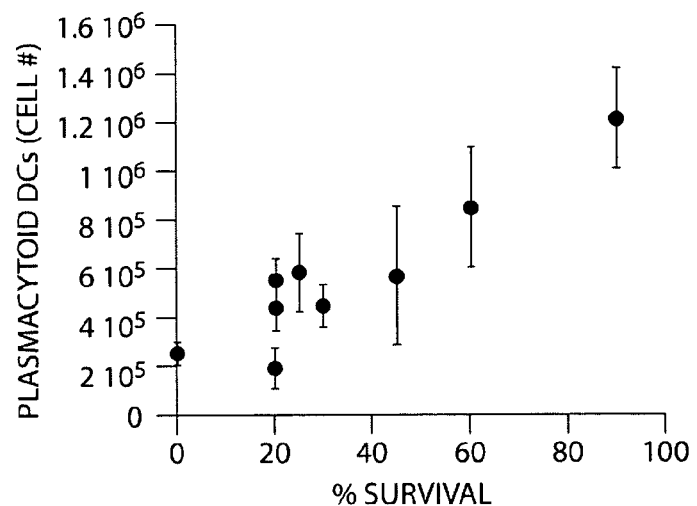
Figure 13D:
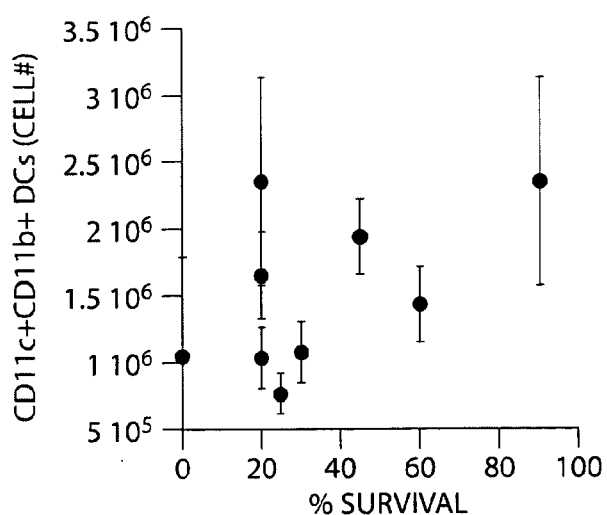
Figure 13E:
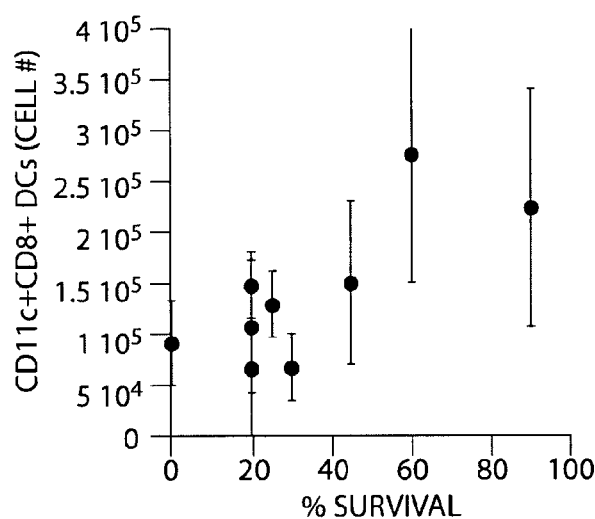

C57BL/6J mice were vaccinated using melanoma antigens (e.g., B16-F10 tumor lysates) presented from PLG-based vaccines that differentially regulated the generation and function of specific DC subsets in situ (varying GM-CSF and CPG-ODN combinations), and challenged with B16-F10 melanoma tumor cells at D14 post-vaccination. PLG vaccines presenting both B16-F10 tumor lysates and either 1, 10, 50 or 100 μg doses of CpG-ODN danger signaling led to approximately 10-30% of the vaccinated mice surviving, tumor-free (FIG. 13A), after an otherwise lethal dose while 100% of unvaccinated mice were euthanized by day 23 due to tumor burden. Surprisingly, GM-CSF mediated DC recruitment combined with antigen and CpG-ODN presentation generated significant tumor protection. CpG-ODN doses of 10, 50, and 100 μg resulted in 50, 60 and 90% survival rates (FIG. 13B). Survival rates correlated strongly with the number of pDCs generated at the PLG vaccine site at day 10, but did not correlate with the total CD11c(+)CD11b(+) DC numbers recruited. Additionally, high survival rates (60% and 90%) were attained with PLG systems that generated relatively high numbers of CD11c(+)CD8(+) DCs ($2 \times 10^5$ cells) (FIG. 13E) and increased IFN-α, IFN-γ, and IL-12 production in situ.

Figure 13F:
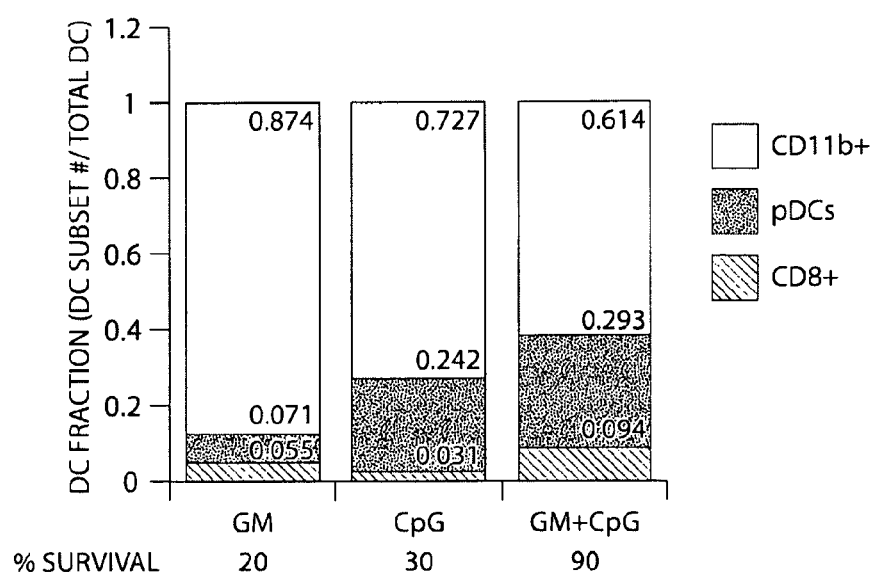

The ability of vaccine systems to recruit a heterogenous DC network also had a profound effect on vaccine efficacy, as the DC population generated by CpG and GM-CSF loaded scaffolds compared to GM-CSF loaded scaffolds resulted in a higher proportion of pDCs (~38% vs. 7%) and CD8+ cDCs (~9.4% vs. 5.5%) (FIG. 13F), leading to a significant enhancement in mouse survival (90% vs. 20%), even though total DC numbers in situ, were statistically similar (3.05±0.55 vs. 2.67±0.64 million DCs). Moreover, tyrosinase-related protein (TRP)-2 is a main antigenic target of the immune response elicited by melanoma vaccines in both mice (including B16 whole cell vaccines) and humans, and staining splenocytes with MHC class I/TRP2 peptide pentamers revealed a significant expansion of TRP2-specific CD8 T cells in mice vaccinated with GM-CSF, antigen and 100 μg of CpG-ODN (0.55% splenocytes, $1.80 \times 10^5 \pm 0.6 \times 10^4$ cells) in comparison to matrices presenting lower CpG doses, either 0 or 50 μg (0.2% and 0.3% splenocytes). The development and expansion of these antigen-specific T cells were induced by the promotion of pDC activation and their corresponding production of type 1 IFNs. These cytotoxic T cells were in turn involved in the killing of tumor cells, which facilitated immune protection after vaccination. These results indicate that devices (PLG matrices) described herein precisely regulate the in situ recruitment and expansion of specialized DC subsets. This preferential recruitment and expansion of pDCs dramatically improves immune responses to cancer antigens, reduces tumor progression, and improves survival of cancer patients compared to previous vaccine approaches.

Figure 14A:
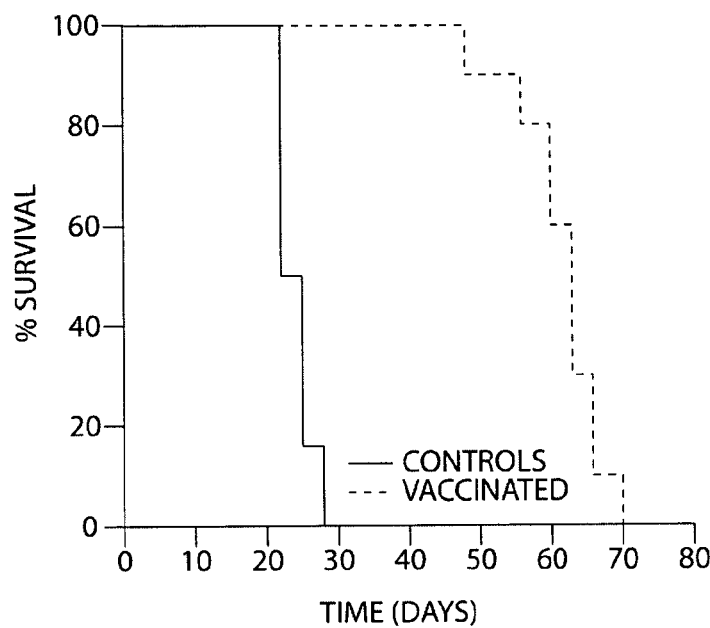
FIGS. 14A-B are line graphs showing PLG vaccine efficacy against established tumors.
Figure 14B:
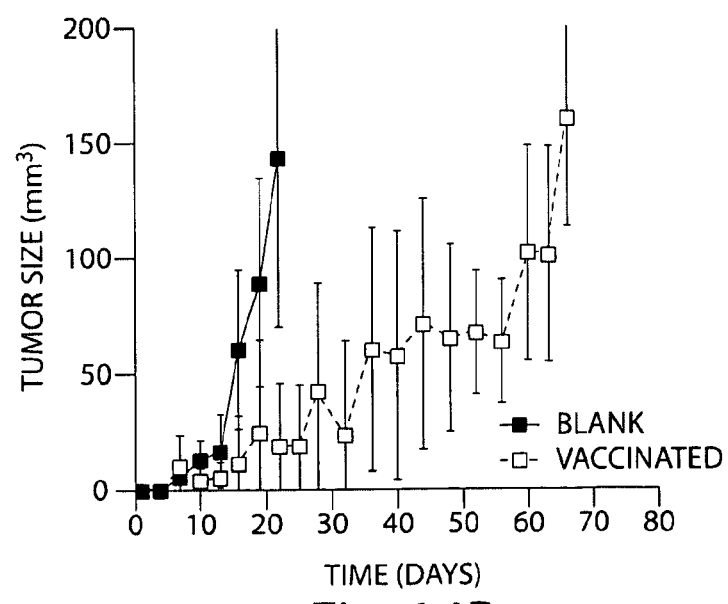

FIGS. 14A-B show survival of mice vaccinated with PLG vaccines versus controls in a therapeutic model. Mice were innoculated with $5 \times 10^5$ tumor cells and tumors were allowed to grow for 7 days in mice until palpable (1-3 mm$^3$). Mice were vaccinated (at Day 7) with PLG scaffolds containing 3 μg GM-CSF, tumor lysates and 100 μg CpG-ODN. Survival data was obtained using mice (n=10) with established tumors (7 days after tumor inoculation). PLG vaccines containing GM-CSF, lysates and CpG-ODN were using for the vaccination.

The macroporous, synthetic ECMs described herein provided control over the presentation of inflammatory and infectious signaling agents creating microenvironments capable of generating distinct DC networks in situ. The total cell number and heterogeneity of these DC networks correlated with the magnitude of immune responses to cancer antigens in B16 melanoma models. GM-CSF was released quickly from PLG-based ECMs to recruit and house host DC precursors and DCs in its macroporous structure. CpG-ODNs were then immobilized within the GM-CSF-secreting matrices to direct pDC development in situ, and, indeed, the CpG signaling not only enhanced CD11c(+)PDCA-1(+) pDC numbers at the implant site, but also enriched the site with pDCs in a dose dependent manner. When tumor antigen was incorporated into PLG matrices, enhancement of activity and enrichment of CD11c+CD8+ cDCs at the vaccine site was observed. The provision of cancer antigens resulted in an enhancement of the total CD8+ cell population, indicating that Cd8+ DCs and Cd8+ T cells responded in situ to the antigen-presenting material and that the immune response had cytotoxic components. Cytokine analysis at the vaccine implant site indicated that DC subsets act in a cooperative fashion to generate an effective immune response. pDC numbers correlated strongly with the presence of type-1 IFNs, which aided the activation of and antigen cross-presentation by CD11c(+)CD11b(+) cDCs (ref) to enhance CTL priming by these cells. Additionally, pDCs and CD8+ cDC numbers correlated with IL-12 production, which promotes antigen expression and cross-presentation by matrix resident DCs and the development and growth of CTLs.

Tumor growth and T-cell analysis indicated that as the heterogeneity of the DC network increased in situ, so did vaccine efficacy. Although total DC numbers remained statistically similar with GM-CSF signaling, provision of CpG-ODN danger signaling increased pDC numbers in a dose dependent manner, which strongly correlated to animal survival after a B16-F10 tumor challenge. CpG-ODN doses of 10, 50 and 100 μg (in GM-CSF secreting matrices) along with melanoma antigen presentation from PLG vaccines resulted in 45%, 60% and 90% survival in mice. Removal of GM-CSF signaling from PLG vaccines sharply reduced the total numbers of DCs generated in situ, which resulted in survival dropping to 10%, whereas removal of CpG-ODN signaling reduce pDC numbers in situ, as a majority of the DCs (87.4%) were CD11b+ CDCs. The minimum number of DCs required to induce protective immunity was determined for each DC subset, as approximately 600,000 pDCs and 200,000 CD8+ cDCs (~30% of total DCs) were required to cooperate with approximately 2,000,0000 CD11b+ cDCs to achieve greater than 50% survival after tumor challenge.

The results are clinically significant as the devices and methods demonstrated the ability to quantitatively target and employ DC subsets in vivo for the generation of immunity, resulting in distinct and protective immune responses.

Other Embodiments

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of continuous in situ dendritic cell programming, comprising administering to a subject a device comprising
   a scaffold polymer selected from the group consisting of poly-lactide-co-glycolide (PLG), alginate, xantham gum, gellan, or emulsan;
   a tumor antigen;
   a recruitment composition comprising a cytokine, which comprises a granulocyte macrophage colony stimulating factor (GM-CSF) that recruits one or more dendritic cells to temporarily reside within said device; and
   a positively charged polyethylenimine (PEI)-condensed toll-like receptor-9 (TLR-9)-activating CpG-ODN which is retained in or on said scaffold polymer,
   wherein said device attracts a dendritic cell and enhances uptake of said CpG-ODN into said dendritic cell, thereby continuously stimulating said dendritic cell to induce an immune response, and wherein said PEI condensed CpG-ODN overcomes the trapping effect of the cytokine on said dendritic cell, thereby inducing said dendritic cell to migrate away from said device.

2. The method of claim 1, wherein said tumor antigen comprises a biopsy tumor cell lysate.

3. The method of claim 1, wherein said device is administered locally at or near a tumor site.

4. The method of claim 1, wherein said dendritic cell comprises a plasmacytoid dendritic cell.

5. The method of claim 1, wherein the scaffold polymer is alginate.

6. The method of claim 1, wherein the scaffold polymer is PLG.

7. The method of claim 1, wherein the CpG-ODN is CpG-ODN 1826.

8. The method of claim 1, wherein the PEI-CpG-ODN is retained in said scaffold polymer.

* * * * *